United States Patent [19]

Morisawa et al.

[11] Patent Number: 5,686,484

[45] Date of Patent: Nov. 11, 1997

[54] MILBEMYCIN DERIVATIVES, THEIR PREPARATION AND THEIR USE

[75] Inventors: Yasuhiro Morisawa; Akio Saito; Satoru Naito; Toshimitsu Toyama; Susumu Kaneko, all of Tokyo, Japan; Louis-Pierre Molleyres, Binningen; Jean-Claude Gehret, Aesch, both of Switzerland

[73] Assignees: Sankyo Co., Ltd., Tokyo, Japan; Ciba-Geigy Corporation, Ardsley, N.Y.

[21] Appl. No.: 396,662

[22] Filed: Mar. 1, 1995

Related U.S. Application Data

[60] Division of Ser. No. 71,765, Jun. 9, 1993, Pat. No. 5,428,034, which is a continuation-in-part of Ser. No. 400,888, Aug. 30, 1989, abandoned, and Ser. No. 951,310, Sep. 24, 1992, abandoned, which is a continuation of Ser. No. 661,856, Feb. 27, 1991, abandoned.

[30] Foreign Application Priority Data

Sep. 2, 1988 [JP] Japan .................... 63-220235
Mar. 1, 1990 [JP] Japan .................... 2-50761

[51] Int. Cl.$^6$ .................... A61K 31/335; C07D 315/00
[52] U.S. Cl. .................... 514/450; 514/212; 514/232.8; 514/253; 514/277; 514/321; 514/338; 514/343; 514/365; 514/444; 549/60; 549/264; 548/206; 548/954; 548/958; 546/197; 546/272.4; 546/276.4; 546/279.4; 544/148; 544/336; 544/405
[58] Field of Search .................... 549/264; 514/450, 514/212, 232.8, 253, 277, 321, 338, 343, 365, 444; 544/148, 336, 405; 548/206, 954, 958; 546/197, 272.4, 276.4, 279.4; 540/596

[56] References Cited

U.S. PATENT DOCUMENTS 3,950,360  4/1976  Aoki et al. .................... 549/264
4,171,314  10/1979  Chabala et al. .................... 549/264

(List continued on next page.)

FOREIGN PATENT DOCUMENTS 0 008 184  7/1979  European Pat. Off. .
0 102 721  7/1983  European Pat. Off. .

(List continued on next page.)

OTHER PUBLICATIONS

Robert W. Burg et al, "Avermectins, New Family of Potential Anthelmintic Agents: Producing Organism and Fermentation", *Antimicrobial Agents & Chemotherapy*, 15 (3), 361–367 (1979).

Primary Examiner—Amelia Owens
Attorney, Agent, or Firm—Frishauf, Holtz, Goodman, Langer & Chick, P.C.

[57]  ABSTRACT

Compounds of formula (I):

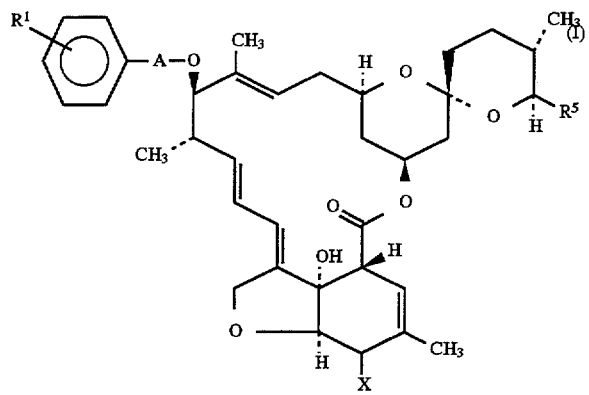

and of formula $(I)_w$:

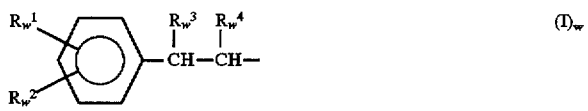

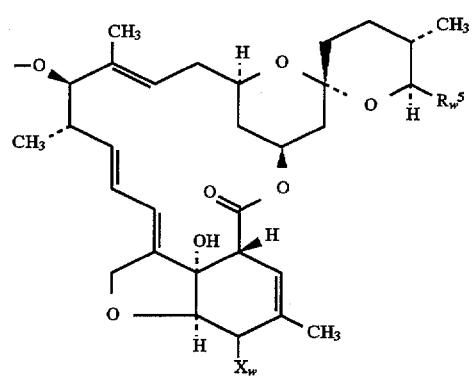

in which: A represents group having one of the following formulae:

$-CHR^2-CHR^3-CHR^4-$
$-CR^2=CR^3-CHR^4-$
or

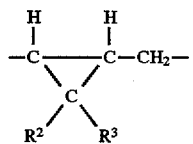

wherein $R^2$, $R^3$ and $R^4$ are independently selected from the group consisting of hydrogen atoms, halogen atoms, alkyl groups having from 1 to 4 carbon atoms, and alkoxy groups having from 1 to 4 carbon atoms;

$R^1$, $R_w^1$ and $R_w^2$ are, for example, hydrogen, halogen, cyano, nitro, optically substituted alkyl, alkoxy or alkoxyalkoxy;

X or $X_w$ is hydroxy, alkanoyloxy, substituted alkanoyloxy or hydroxyimino; $R_w^3$ and $R_w^4$ are each hydrogen, alkyl or alkoxy; $R^5$ and $R_w^5$ are methyl, ethyl, isopropyl or sec-butyl; and salts thereof have valuable anthelmintic, acaricidal and insecticidal activities.

47 Claims, No Drawings

U.S. PATENT DOCUMENTS

| | | | |
|---|---|---|---|
| 4,173,571 | 11/1979 | Chabala et al. | 549/264 |
| 4,199,569 | 4/1980 | Chabala et al. | 549/264 |
| 4,200,581 | 4/1980 | Fisher et al. | 549/264 |
| 4,201,861 | 5/1980 | Mrozik et al. | 549/264 |
| 4,203,976 | 5/1980 | Fisher et al. | 549/264 |
| 4,206,205 | 6/1980 | Mrozik et al. | 549/264 |
| 4,289,760 | 9/1981 | Mrozik et al. | 549/264 |
| 4,346,171 | 8/1982 | Takiguchi et al. | 549/264 |
| 4,423,209 | 12/1983 | Mrozik | 549/264 |
| 4,457,920 | 7/1984 | Mrozik | 549/264 |
| 4,547,491 | 10/1985 | Mrozik et al. | 549/264 |
| 4,547,520 | 10/1985 | Ide et al. | 549/264 |
| 4,579,864 | 4/1986 | Linn et al. | 549/264 |
| 4,696,945 | 9/1987 | Frei et al. | 549/264 |
| 4,959,386 | 9/1990 | Frei et al. | 549/264 |

FOREIGN PATENT DOCUMENTS

| | | |
|---|---|---|
| 0 115 930 | 1/1984 | European Pat. Off. . |
| 0 170 006 | 6/1985 | European Pat. Off. . |
| 0 184 989 | 11/1985 | European Pat. Off. . |
| 0 180 539 | 5/1986 | European Pat. Off. . |
| 0 203 832 | 6/1986 | European Pat. Off. . |
| 0 357 460 | 3/1990 | European Pat. Off. . |
| 57-120589 | 7/1982 | Japan . |
| 59-16894 | 1/1984 | Japan . |
| 669382 | 3/1989 | Switzerland . |
| 2 176 182 | 4/1986 | United Kingdom . |

MILBEMYCIN DERIVATIVES, THEIR PREPARATION AND THEIR USE

CROSS-REFERENCES TO RELATED APPLICATIONS

This is a divisional of application Ser. No. 08/071,765, filed Jun. 9, 1993, now U.S. Pat. No. 5,428,034, which is a CIP of Ser. No. 07/951,310, filed Sep. 24, 1992, now abandoned, which is a continuation of Ser. No. 07/661,856, filed Feb. 27, 1991, now abandoned, and said Ser. No. 8/071,765, filed Jun. 9, 1993 which is a CIP of Ser. No. 07/400,888, filed Aug. 30, 1989, now abandoned.

BACKGROUND OF THE INVENTION

The present invention relates to a series of new macrolide compounds which are chemically related to certain known classes of macrolides including those known as the milbemycins and the avermectins. These compounds have valuable acaricidal, insecticidal and anthelmintic activities. The invention also provides methods of preparing these compounds and compositions and methods for using them.

There are several classes of known compounds with a structure based on a 16-membered macrolide ring, which compounds are obtained by fermentation of various microorganisms or are obtained semi-synthetically by chemical derivatization of such natural fermentation products, and which exhibit acaricidal, insecticidal, anthelmintic and antiparasitic activities. The milbemycins and avermectins are examples of two such classes of known compounds, but various others also exist and are identified in the art by different names or code numbers. The names for these various macrolide compounds have generally been taken from the names or code numbers of the microorganisms which produce the naturally occurring members of each class, and these names have then been extended to cover the chemical derivatives of the same class, with the result that there has been no standardized systematic nomenclature for such compounds generally.

In order to avoid confusion, a standardized system of nomenclature will be used herein, which follows the normal rules for naming derivatives of organic compounds as recommended by the International Union of Pure and Applied Chemistry (IUPAC), Organic Chemistry Division, Commission on Nomenclature of Organic Chemistry, and which is based primarily on the hypothetical parent compound hereby defined as "milbemycin" and represented by the formula (A):

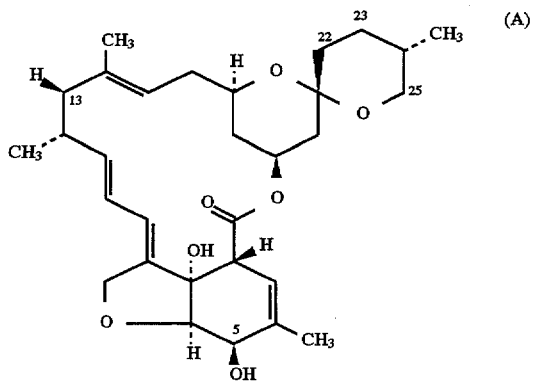

(A)

For the avoidance of doubt, formula (A) also shows the numbering of positions of the macrolide ring system applied to those positions most relevant to the compounds of the present invention and of the prior art.

The naturally produced milbemycins are a series of macrolide compounds known to have anthelmintic, acaricidal and insecticidal activities. Milbemycin D was disclosed in U.S. Pat. No. 4,346,171, where it was referred to as "Compound B-41D", and milbemycins $A_3$ and $A_4$ were disclosed in U.S. Pat. No. 3,950,360. These compounds may be represented by the above formula (A) in which there is a hydrogen atom at position 13 and position 25 is substituted with a methyl group, an ethyl group or an isopropyl group, these compounds being designated as milbemycin $A_3$, milbemycin $A_4$ and milbemycin D, respectively. The milbemycin analog having a hydrogen atom at position 13 and substituted at position 25 with a sec-butyl group was disclosed in U.S. Pat. No. 4,173,571, where it was known as "13-deoxy-22,23-dihydroavermectin $B_{1a}$ aglycone". Certain of the compounds of the present invention are named as derivatives of this and related compounds, the numbering system being as shown above on formula (A).

Subsequently, various derivatives of the original milbemycins and avermectins have been prepared and their activities investigated. For example, 5-esterified milbemycins have been disclosed in U.S. Pat. Nos. 4,201,861, 4,206,205, 4,173,571, 4,171,314, 4,203,976, 4,289,760, 4,457,920, 4,579,864 and 4,547,491, in European Patent Publications No. 8184, No. 102,721, No. 115,930, No. 180,539 and No. 184,989 and in Japanese Patent Applications Kokai (i.e. as laid open to public inspection) No. 57-120589 and 59-16894.

13-Hydroxy-5-ketomilbemycin derivatives have been disclosed in U.S. Pat. No. 4,423,209. Milbemycin 5-oxime derivatives were disclosed in U.S. Pat. No. 4,547,520 and in European Patent Publication No. 203 832.

Milbemycins having an ether linkage at the 13 position are of particular relevance to the present invention and the lower alkyl, phenyl and benzyl ethers are described in general terms in U.S. Pat. No. 4,696,945, but only the methyl and ethyl ethers are specifically described in the Examples. Certain other milbemycin derivatives having a 13-ether group are disclosed in European Patent Publication No. 357 460.

Like the milbemycins, the avermectins are based upon the same 16-membered ring macrolide compound. The avermectins are disclosed, for example in J. Antimicrob. Agents Chemother., 15(3), 361–367 (1979). These compounds may be represented by the above formula (A) but with a carbon-carbon double bond at positions 22 and 23, and having position 13 substituted with a 4'-(α-L-oleandrosyl)-α-L-oleandrosyloxy group. Position 25 may be substituted with an isopropyl group or a sec-butyl group, these compounds being designated as avermectin $B_{1b}$ and avermectin $B_{1a}$, respectively. 22,23-Dihydroavermectins $B_{1a}$ and $B_{1b}$ may be obtained by reduction of the double bond between the 22 and 23 positions and are disclosed in U.S. Pat. No. 4,199,569. The aglycone derivatives of the avermectins, which are milbemycin analogs, have sometimes been referred to in the literature as C-076 compounds, and various derivatives of these are known. For example, U.S. Pat. No. 4,201,861 discloses such derivatives substituted with a lower alkanoyl group at position 13.

European Patent Publication No. 170 006 discloses a family of bioactive compounds produced by fermentation, identified collectively by the code number LL-F28249. Some of these have a 16-membered macrolide structure corresponding to the above formula (A), substituted with a hydroxy group at position 23 and with a 1-methyl-1-propenyl, 1-methyl-1-butenyl or 1,3-dimethyl-1-butenyl group at position 25. In these compounds, the hydroxy group at position 5 may also be replaced by a methoxy group.

British Patent Publication No. 2,176,182 discloses another group of macrolide antibiotics corresponding to the above formula (A) with a hydroxy or substituted hydroxy group at position 5, a hydroxy, substituted hydroxy or keto group at position 23, and an α-branched alkenyl group at position 25.

The various classes of milbemycin-related macrolide compounds described above are all disclosed as having one or more types of activity as antibiotic, anthelmintic, ectoparasiticidal, acaricidal or other pesticidal agents. However, there is still a continuing need to provide such agents with improved activity against one or more classes of pests.

It has now been discovered that the activity of such milbemycin-related derivatives can be improved by appropriately selecting the combination of substituents on the macrolide ring system, especially the substituents at position 13. In particular, it has now been found that the activity of the compounds can be improved upon by appropriate selection of certain highly specific ether groups at the 13 position, which are cinnamyl ether groups or derivatives thereof, as specified below.

BRIEF SUMMARY OF INVENTION

Accordingly, it is an object of the present invention to provide such macrolide compounds having improved activity. It is another object of the invention to provide methods for preparing such compounds. It is a still further object of the invention to provide pesticidal compositions and methods using the said compounds.

In accordance with these objects, the invention provides compounds having the formula (I):

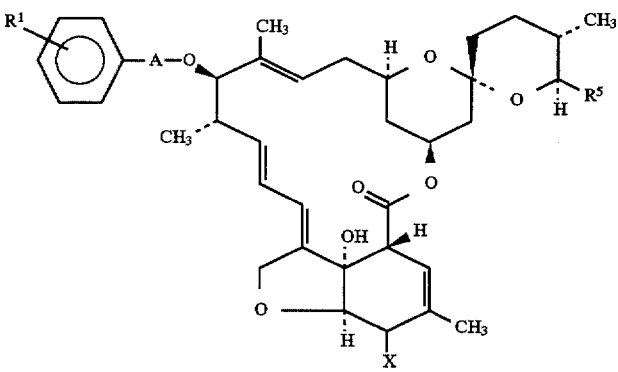

in which:

R$^1$ represents: a hydrogen atom; a halogen atom; a cyano group; a nitro group; an alkyl group which has from 1 to 4 carbon atoms and which is unsubstituted or has at least one substituent selected from the group consisting of substituents (a); an alkoxy group having from 1 to 4 carbon atoms; an alkoxyalkoxy group having a total of from 2 to 6 carbon atoms; or a group having one of the following formulae:

—(CH$_2$)$_n$NHR$^9$

—(CH$_2$)$_n$NR$^9$COR$^6$

—(CH$_2$)$_n$NR$^9$COCOR$^6$

—(CH$_2$)$_n$NR$^9$COCOOR$^7$

—(CH$_2$)$_n$NR$^9$CHR$^6$NHCOR$^6$

—(CH$_2$)$_n$NR$^9$CHR$^6$NHCONHR$^6$

—(CH$_2$)$_n$NR$^9$CHR$^6$NHCOOR$^7$

—(CH$_2$)$_n$NR$^9$C(=Y)YR$^6$

—(CH$_2$)$_n$NR$^9$C(=Y)NR$^6$R$^6$

—(CH$_2$)$_n$NR$^9$C(=Y)NR$^6$NR$^6$R$^6$

—(CH$_2$)$_n$NR$^9$C(=Y)NR$^6$NHZ

—(CH$_2$)$_n$NR$^9$C(=NR$^{11}$)NHR$^{11}$

—(CH$_2$)$_n$NR$^9$C(=NR$^{11}$)R$^6$

—(CH$_2$)$_n$NR$^9$SO$_m$R$^6$

—CONHR$^6$ or

—COOR$^7$ wherein:

m is 1 or 2;

n is 0, 1 or 2;

R$^6$ represents a hydrogen atom; an alkyl group having from 1 to 8 carbon atoms; a substituted alkyl group having from 1 to 8 carbon atoms and having at least one substituent selected from the group consisting of substituents (b); an aliphatic hydrocarbon group having from 2 to 8 carbon atoms and having one or two carbon-carbon double or triple bonds; a cycloalkyl group having from 2 to 8 carbon atoms; a substituted cycloalkyl group having from 2 to 8 carbon atoms and having at least one substituent selected from the group consisting of substituents (c); an aryl group which has from 6 to 14 ring carbon atoms and which is unsubstituted or which has at least one substituent selected from the group consisting of substituents (c); an aryloxy group which has from 6 to 14 ring carbon atoms and which is unsubstituted or which has at least one substituent selected from the group consisting of substituents (c); an arylthio group which has from 6 to 14 ring carbon atoms and which is unsubstituted or which has at least one substituent selected from the group consisting of substituents (c); or a heterocyclic group having from 3 to 6 ring atoms, of which at least one is a hetero-atom selected from the group consisting of nitrogen, oxygen and sulfur hetero-atoms, said heterocyclic group being unsubstituted or having at least one substituent selected from the group consisting of substituents (c) and being a monocyclic ring or being fused to one or two benzene or monocyclic aromatic heterocyclic rings, said monocyclic aromatic heterocyclic ring having 5 or 6 ring atoms of which from 1 to 3 are hetero-atoms selected from the group consisting of nitrogen, oxygen and sulfur hetero-atoms, to form a bicyclic or tricyclic ring system; and, where there are two or more groups or atoms represented by $R^6$ these are the same or different from each other; or, where two groups represented by $R^6$ are attached to a single nitrogen atom, these groups $R^6$, together with a nitrogen atom to which they are attached, may be fused to form a heterocyclic ring having from 3 to 7 ring atoms, which ring additionally contains 0 or 1 further heteroatom selected from the group consisting of oxygen, nitrogen and sulfur atoms, in addition to said nitrogen atom; or, where two groups represented by $R^6$ are attached to adjacent nitrogen atoms, these groups $R^6$ together with a nitrogen atoms to which they are attached, may be fused to form a heterocyclic ring having from 3 to 7 ring atoms, which ring additionally contains 0 or 1 further hetero-atom selected from the group consisting of oxygen, nitrogen and sulfur atoms, in addition to said nitrogen atoms;

$R^7$ represents an alkyl group having from 1 to 4 carbon atoms, a cycloalkyl group having from 3 to 7 carbon atoms, or an aralkyl group in which an alkyl group having from 1 to 4 carbon atoms is substituted by from 1 to 3 aryl groups which have from 6 to 10 ring carbon atoms and which have at least one substituent selected from the group consisting of substituents (c);

$R^9$ represents a hydrogen atom or an alkyl group having from 1 to 4 carbon atoms;

$R^{11}$ represents any of the groups or atoms defined above for $R^6$, or it represents a cyano group, a nitro group, a group of formula —$COOR^7$ (wherein $R^7$ is as defined above), or a group of formula —$COR^6$ (wherein $R^6$ is as defined above);

Y represents an oxygen atom or a sulfur atom; and, where there are two or more groups represented by Y, these are the same or different from each other;

Z represents a group of formula —$COOR^7$ (wherein $R^7$ is as defined above), a group of formula —$COR^6$ (wherein $R^6$ is as defined above) or a group of formula —$SO_2R^6$ (wherein $R^6$ is as defined above);

A represents a group having one of the following formulae:

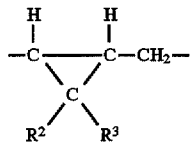

wherein $R^2$, $R^3$ and $R^4$ are independently selected from the group consisting of hydrogen atoms, halogen atoms, alkyl groups having from 1 to 4 carbon atoms, and alkoxy groups having from 1 to 4 carbon atoms;

$R^5$ represents a methyl group, an ethyl group, an isopropyl group or a sec-butyl group; and X represents: a hydroxy group; an alkanoyloxy group which has from 1 to 5 carbon atoms, and which is unsubstituted or has at least one substituent selected from the group consisting of substituents (d); or a hydroxyimino group;

substituents (a):

halogen atoms, alkoxy groups having from 1 to 4 carbon atoms, alkylthio groups having from 1 to 4 carbon atoms, and alkanoyloxy groups having from 1 to 5 carbon atoms;

substituents (b):

cycloalkyl groups having from 3 to 8 carbon atoms; alkoxy groups having from 1 to 4 carbon atoms; alkylthio groups having from 1 to 4 carbon atoms; cyanoalkylthio groups having from 2 to 5 carbon atoms; alkoxycarbonyl groups having from 2 to 5 carbon atoms; halogen atoms; cyano groups; nitro groups; amino groups; aryl groups which have from 6 to 14 ring carbon atoms and which are unsubstituted or have at least one substituent selected from the group consisting of substituents (c); aromatic heterocyclic groups which have 5 or 6 ring atoms and which are unsubstituted or which have at least one substituent selected from the group consisting of substituents (c) and such heterocyclic groups which are fused to one or two benzene or monocyclic aromatic heterocylic rings, said monocyclic aromatic heterocyclic ring having 5 or 6 ring atoms of which from 1 to 3 are hetero-atoms selected from the group consisting of nitrogen, oxygen and sulfur hetero-atoms, to form a bicyclic or tricyclic group; aryloxy groups which have from 6 to 14 ring carbon atoms and which are unsubstituted or have at least one substituent selected from the group consisting of substituents (c); and arylthio groups which have from 6 to 14 ring carbon atoms and which are unsubstituted or have at least one substituent selected from the group consisting of substituents (c);

substituents (c):

alkyl groups having from 1 to 4 carbon atoms, alkoxy groups having from 1 to 4 carbon atoms, alkylthio groups having from 1 to 4 carbon atoms, alkanoyloxy groups having from 1 to 5 carbon atoms, alkoxycarbonyl groups having from 2 to 5 carbon atoms, halogen atoms, cyano groups, nitro groups, amino groups, alkylamino groups in which the alkyl part has from 1 to 4 carbon atoms, dialkylamino groups in which each alkyl part is independently selected from the group consisting of alkyl groups having from 1 to 4 carbon atoms, carbamoyl groups, alkylcarbamoyl groups in which the alkyl part has from 1 to 4 carbon atoms, dialkylcarbamoyl groups in which each alkyl part is independently selected from the group consisting of alkyl groups having from 1 to 4 carbon atoms, and alkanoylamino groups having from 1 to 5 carbon atoms;

substituents (d):

halogen atoms, alkoxy groups having from 1 to 4 carbon atoms, alkoxycarbonyl groups having from 2 to 5 carbon atoms, and carboxy groups;

and salts and esters thereof.

In accordance with the aforementioned objects, the invention also concerns compounds having the formula $(I)_w$:

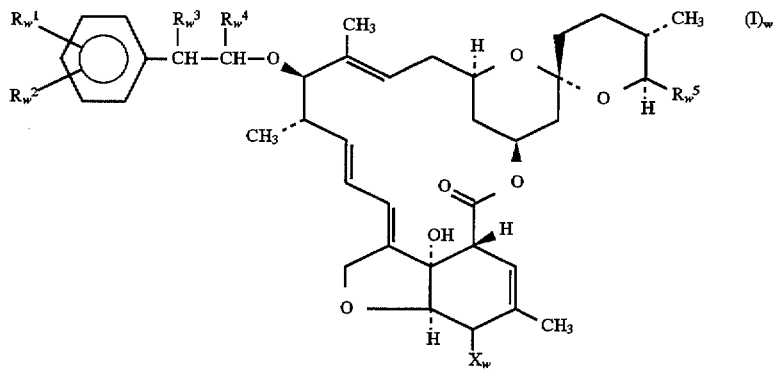

in which:

$R_w^1$ and $R_w^2$ are independently selected from the group consisting of: hydrogen atoms; halogen atoms; cyano groups; nitro groups; $C_1$-$C_4$ alkyl groups; substituted $C_1$-$C_4$ alkyl groups having an least one substituents selected from the group consisting of substituents (a), defined below; $C_1$-$C_4$ alkoxy groups; $C_2$-$C_6$ alkoxy-alkoxy groups; groups of formula —$(CH_2)_{n_w}NHR_w^9$.

in which:

$n_w$ represents 0 or the integer 1 or 2, and $R_w^9$ represents a hydrogen atom or a $C_1$-$C_4$ alkyl group;

groups of formula —$(CH_2)_{n_w}NR_w^9C(=O)R_w^6$.

in which:

$n_w$ and $R_w^9$ are as defined above, and $R_w^6$ represents: a hydrogen atom; a $C_1$-$C_4$ alkyl group: a substituted $C_1$-$C_4$ alkyl group having at least one substituent selected from the group consisting of substituents (b)$_w$, defined below; a $C_2$-$C_8$ aliphatic hydrocarbon group having one or two ethylenically unsaturated carbon-carbon double bonds, said group being unsubstituted or having at least one substituent selected from the group consisting of substituents (b)$_w$, defined below: a $C_2$-$C_8$ alkynyl group; a substituted $C_2$-$C_8$ alkynyl group having at least one substituent selected from the group consisting of substituents (b)$_w$, defined below; a $C_3$-$C_8$ cycloalkyl group: a substituted $C_3$-$C_8$ cycloalkyl group having at least one substituent selected from the group consisting of substituents (c)$_w$, defined below; a carbocyclic aryl group having from 6 to 14 ring carbon atoms and being unsubstituted or having at least one substituent selected from the group consisting of substituents (c)$_w$, defined below; or a heterocyclic group having from 3 to 6 ring atoms of which at least one is a hetero-atom selected from the group consisting of nitrogen, oxygen and sulfur hetero-atoms, said heterocyclic group being monocyclic or fused to one or two benzene rings and being unsubstituted or having at least one substituent selected from the group consisting of substituents (c), defined below;

groups of formula —$(CH_2)_{n_w}NR_w^9COCOR_w^6$ in which $n_w$, $R_w^6$ and $R_w^9$ are as defined above;

groups of formula —$(CH_2)_{n_w}R_w^9COCOOR_w^7$ in which $n_w$ and $R_w^9$ are as defined above and $R_w^7$ represents a $C_1$-$C_4$ alkyl group, a $C_3$-$C_8$ cycloalkyl group or an aralkyl group as defined below;

groups of formula —$(CH_2)_{n_w}NR_w^9CHR_w^6NHCOR_w^6$ in which $n_w$, $R_w^6$ and $R_w^9$ are as defined above;

groups of formula —$(CH_2)_{n_w}NR_w^9CHR_w^6NHCONHR_w^6$ in which $n_w$, $R_w^6$ and $R_w^9$ are as defined above;

groups of formula —$(CH_2)_{n_w}NR_w^9CHR_w^6NHCOOR_w^7$ in which $n_w$, $R_w^6$, $R_w^7$ and $R_w^9$ are as defined above:

groups of formula —$(CH_2)_{n_w}NR_w^9C(=Y_w)_wYR_w^6$ in which $n_w$, $R_w^6$ and $R_w^9$ are as defined above and the two symbols $Y_w$ are independently selected from the group consisting of oxygen and sulfur atoms;

groups of formula —$(CH_2)_{n_w}NR_w^9C(=Y_w)NR_w^{6'}R_w^{6'}$ in which $n_w$, $Y_w$ and $R_w^9$ are as defined above, and the two symbols $R_w^{6'}$ are independently selected from the group consisting of $R_w^6$, or the two, together with the nitrogen atom to which they are attached, form a heterocyclic group having from 3 to 7 ring atoms of which one is said nitrogen atom and 0 or 1 is an additional hetero-atom selected from the group consisting of nitrogen, oxygen and sulfur hetero-atoms;

groups of formula —$(CH_2)_{n_w}NR_w^9C(=Y_w)NR_w^{6''}NR_w^{6''}R_w^{6''}$ in which $n_w$, $Y_w$ and $R_w^9$ are as defined above, and each of the symbols $R_w^{6''}$ is independently selected from the group consisting of $R_w^6$, or any two of the symbols $R_w^{6''}$, together with the nitrogen atom to which each is attached, forms a heterocyclic group having from 3 to 7 ring atoms of which one or two is said nitrogen atom or atoms and 0 or 1 is an additional hetero-atom selected from the group consisting of nitrogen, oxygen and sulfur hetero-atoms;

groups of formula —$(CH_2)_{n_w}NR_w^9C(=Y_w)NR_w^6NHZ_w$ in which $n_w$, $Y_w$, $R_w^6$ and $R_w^9$ are as defined above and $Z_w$ represents a group of formula —$COOR_w^7$ in which $R_w^7$ is as defined above, a group of formula —$COR_w^6$, in which $R_w^6$ is as defined above, or a group of formula —$SO_2R_w^6$, in which $R_w^6$ is as defined above;

groups of formula —$(CH_2)_{n_w}NR_w^9C(=NR_w^{10})NHR_w^{10}$ in which $n_w$ and $R_w^9$ are as defined above and the two symbols $R_w^{10}$ are independently selected from the group consisting of $R_w^6$, cyano groups, nitro groups, groups of formula —$COOR_w^7$, in which $R_w^7$ is as defined above, and groups of formula —$COR_w^6$, in which $R_w^6$ is as defined above;

groups of formula —$(CH_2)_{n_w}NR_w^9C(=NR_w^{10})R_w^6$
in which $n_w$, $R_w^6$, $R_w^9$ and $R_w^{10}$ are as defined above;

groups of formula —$(CH_2)_{n_w}NR_w^9SO_mR_w^6$
in which $n_w$, $R_w^6$ and $R_w^9$ are as defined above and m is 1 or 2;

groups of formula —$CONHR_w^6$
in which $R_w^6$ is as defined above; and groups of formula —$COOR_w^7$
in which $R_w^7$ is as defined above;

$R_w^3$ and $R_w^4$ are independently selected from the group consisting of hydrogen atoms, $C_1$–$C_4$ alkyl groups and $C_1$–$C_4$ alkoxy groups;

$R_w^5$ represents a methyl group, an ethyl group, an isopropyl group or a sec-butyl group; and $X_w$ represents a hydroxy group, a $C_1$–$C_5$ alkanoyloxy group, a substituted $C_1$–$C_5$ alkanoyloxy group having at least one substituent selected from the group consisting of substituents (d)$_w$, defined below, or a hydroxyimino group;

said aralkyl groups have from 1 to 4 carbon atoms in the alkyl part and from 6 to 10 ring atoms in the aryl part, which is a carbocyclic aryl group which is unsubstituted or has at least one substituent selected from the group consisting of substituents (c)$_w$, defined below;

substituents (a)w:

halogen atoms, $C_1$–$C_4$ alkoxy groups, $C_1$–$C_4$ alkylthio groups and $C_1$–$C_5$ alkanoyloxy groups;

substituents (b)w:

$C_3$–$C_8$ cycloalkyl groups: $C_1$–$C_4$ alkoxy groups; $C_1$–$C_4$ alkylthio groups; $C_2$–$C_5$ cyanoalkylthio groups; $C_2$–$C_5$ alkoxycarbonyl groups; halogen atoms; cyano groups; micro groups; amino groups; carbocyclic aryl groups having from carbon atoms and being unsubstituted or having at least one substituent selected from the group consisting of substituents (c)$_w$, defined below; aromatic heterocyclic groups having form 5 to 8 ring atoms of which from 1 to 4 are hetero-atoms selected from the group consisting of nitrogen, oxygen and sulfur heteroatoms, said heterocyclic group being monocyclic or fused either to a benzene ring or to a heterocyclic group which has 5 to 6 ring atoms of which from 1 to 3 are nitrogen hetero-atoms and being unsubstituted or having at least one substituent selected from the group consisting of substituents (c)$_w$, defined below; and aryloxy and arylthio groups in which the aryl part has from 6 to 10 carbon atoms and is unsubstituted or has at least one substituent selected from the group consisting of substituents (c)$_w$, defined below;

substituents (c)w:

$C_1$–$C_4$ alkyl groups, $C_1$–$C_4$ alkoxy groups, $C_1$–$C_4$ alkylthio groups, $C_1$–$C_5$ alkanoyloxy groups, $C_2$–$C_5$ alkoxycarbonyl groups, halogen atoms, cyano groups, nitro groups, amino groups, mono- and di- alkylamino groups in which the or each alkyl part is $C_1$–$C_4$, carbamoyl groups, mono- and di- alkylcarbamoyl groups in which the or each alkyl part is $C_1$–$C_4$, and $C_1$–$C_5$ alkanoylamino groups:

substituents (d)w:

halogen atoms, $C_1$–$C_4$ alkoxy groups, $C_2$–$C_5$ alkoxycarbonyl groups and carboxy-groups:

and salts thereof.

The invention still further provides an anthelmintic, acaricidal and insecticidal composition comprising an anthelmintic, acaricidal and insecticidal compound in admixture with a pharmaceutically, agriculturally, veterinarily or horticulturally acceptable carrier or diluent, wherein said compound is selected from the group consisting of compounds of formula (I) or formula (I)$_w$, and salts and esters thereof.

The invention still further provides a method of treating an animal, which may be human or non-human, parasitized by a parasite selected from the group consisting of helminths, acarids and insects by administering thereto at least one compound selected from the group consisting of compounds of formula (I) and salts and esters thereof or formula (I)$_w$ and salts thereof.

The invention still further provides a method of protecting animals or plants from damage by parasites selected from the group consisting of acarids, helminths and insects, which comprises applying an active compound to said animals, to said plants or to seeds of said plants or to a locus including said animals, plants or seeds, wherein the active compound is selected from the group consisting of at least one compound of formula (I) and salts and esters thereof or formula (I)$_w$ and salts thereof.

DETAILED DESCRIPTION OF INVENTION

In the compounds of the formula (I) in the present invention, where $R^1$ represents a halogen atom, this may be a fluorine, chlorine, bromine or iodine atom, preferably a chlorine or bromine atom.

When $R^1$ represents an alkyl group, this may be a straight or branched chain alkyl group having from 1 to 4 carbon atoms, and examples include the methyl, ethyl, propyl, isopropyl, butyl, isobutyl, sec-butyl and t-butyl groups, of which we prefer the methyl, ethyl, propyl, isopropyl, butyl and sec-butyl groups, most preferably the methyl group or the ethyl group. Such groups may be unsubstituted or they may have at least one substituent selected from the group consisting of substituents (a), defined above and exemplified below. Where the group is substituted, there is no particular restriction on the number of substituents, except such as may be imposed by the number of substitutable positions, and, possibly, by steric constraints. Examples of groups and atoms which may be represented by substituents (a) include:

halogen atoms, such as the fluorine, chlorine, bromine and iodine atoms;

alkoxy groups having from 1 to 4 carbon atoms, which may be straight or branched chain alkoxy groups having from 1 to 4 carbon atoms, and examples include the methoxy, ethoxy, propoxy, isopropoxy, butoxy, isobutoxy, sec-butoxy and t-butoxy groups, of which we prefer the methoxy, ethoxy, propoxy, isopropoxy and butoxy groups, most preferably the methoxy group;

alkylthio groups having from 1 to 4 carbon atoms, which may be straight or branched chain alkylthio groups having from 1 to 4 carbon atoms, and examples include-the methylthio, ethylthio, propylthio, isopropylthio, butylthio, isobutylthio, sec-butylthio and t-butylthio groups, of which we prefer the methylthio, ethylthio, propylthio, isopropylthio, butylthio and isobutylthio groups, most preferably the methylthio group; and alkanoyloxy groups having from 1 to 5 carbon atoms, which may be straight or branched chain groups, such as the formyloxy, acetoxy, propionyloxy, butyryloxy, isobutyryloxy, valeryloxy, isovaleryloxy and pivaloyloxy groups, of which we prefer the formyloxy, propionyloxy, butyryloxy, isovaleryloxy and pivaloyloxy groups.

When $R^1$ represents an alkoxy group, this may be a straight or branched chain alkoxy group having from 1 to 4 carbon atoms, and examples include the methoxy, ethoxy, propoxy, isopropoxy, butoxy, isobutoxy, sec-butoxy and t-butoxy groups, of which we prefer the methoxy, ethoxy, propoxy, isopropoxy, butoxy and sec-butoxy groups, most preferably the methoxy group.

Where $R^1$ represents an alkoxyalkoxy group, this has a tonal of from 2 to 6 carbon atoms, and each alkoxy part may be a straight or branched chain group, although each is preferably straight chain; preferably each alkoxy part has from 1 to 4 carbon atoms, provided that they total no more than 6. Examples of such groups include the methoxymethoxy, ethoxymethoxy, propoxymethoxy, butoxymethoxy, methoxyethoxy, ethoxyethoxy and butoxyethoxy groups.

Where $R^6$ represents an alkyl group this may be a straight or branched chain alkyl group having from 1 to 8, preferably from 1 to 4, carbon atoms, and the group may be unsubstituted or it may be substituted by at least one of substituents (b), defined above and exemplified below. Examples of such alkyl groups include the methyl, ethyl, propyl, isopropyl, butyl, isobutyl, sec-butyl, t-butyl, pentyl, isopentyl, neopentyl, hexyl, isohexyl, sec-hexyl, t-hexyl, heptyl, isoheptyl and octyl groups, preferably the methyl, ethyl, propyl, isopropyl, butyl, sec-butyl, pentyl, isopentyl, hexyl, sec-hexyl and heptyl groups. Examples of the groups and atoms which may be included in substituents (b) include:

cycloalkyl groups having from 3 to 8 carbon atoms, such as the cyclopropyl, cyclobutyl, cyclopentyl, cyclohexyl and cycloheptyl groups;

halogen atoms, alkoxy groups having from 1 to 4 carbon atoms and alkylthio groups having from 1 to 4 carbon atoms, such as those exemplified in relation to substituents (a);

cyanoalkylthio groups having from 2 to 5 carbon atoms, such as the cyanomethylthio, 1-cyanoethylthio, 2-cyanoethylthio, 1-cyanopropylthio, 2-cyanopropylthio and 1-cyanobutylthio groups;

alkoxycarbonyl groups having from 2 to 5 carbon atoms such as the methoxycarbonyl, ethoxycarbonyl, propoxycarbonyl, isopropoxycarbonyl, butoxycarbonyl, isobutoxycarbonyl, sec-butoxycarbonyl and t-butoxycarbonyl groups, preferably the methoxycarbonyl, ethoxycarbonyl, propoxycarbonyl and butoxycarbonyl groups;

cyano groups, nitro groups and amino groups;

carbocyclic aryl groups which have from 6 to 14, preferably from 6 to 10 and more preferably 6 or 10, ring carbon atoms and which are unsubstituted or have at least one substituent selected from the group consisting of substituents (c), defined and exemplified below, such as the phenyl, naphthyl (1- or 2-) and anthryl groups, of which the phenyl and naphthyl groups are preferred and the phenyl group is most preferred; such groups may be unsubstituted or substituted; aromatic heterocyclic groups which have 5 or 6 ring atoms and which are unsubstituted or which have at least one substituent selected from the group consisting of substituents (c); examples of the unsubstituted groups include the pyridyl, thienyl, furyl, pyrrolyl, imidazolyl, triazolyl, tetrazolyl, thiazolyl and oxazolyl groups, and such groups which are fused to at least one benzene ring, such as the indolyl group; any of these groups may be unsubstituted or they may be substituted by at least one of substituents (c), defined above and exemplified below;

aryloxy groups which have from 6 to 14 ring carbon atoms and which are unsubstituted or have at least one substituent selected from the group consisting of substituents (c); and arylthio groups which have from 6 to 14 ring carbon atoms and which are unsubstituted or have at least one substituent selected from the group consisting of substituents (c); in each case, the aryl part of these groups may be as exemplified above in relation to the aryl groups.

Examples of the groups and atoms which may be represented by substituents (c) include:

alkyl groups having from 1 to 4 carbon atoms, alkoxy groups having from 1 to 4 carbon atoms, alkylthio groups having from 1 to 4 carbon atoms, alkanoyloxy groups having from 1 to 5 carbon atoms, alkoxycarbonyl groups having from 2 to 5 carbon atoms and halogen atoms, such as those exemplified above in relation to substituents (a) and/or (b);

cyano groups, nitro groups and amino groups;

alkylamino groups and dialkylamino groups in which the or each alkyl part has from 1 to 4 carbon atoms, such as the methylamino, ethylamino, propylamino, isopropylamino, dimethylamino, diethylamino, N-butyl-N-methylamino, N-t-butyl-N-methylamino, N-methyl-N-propylamino, N-ethyl-N-propylamino, dipropylamino, diisopropylamino, butylamino, isobutylamino, dibutylamino and diisobutylamino groups, especially the methylamino, ethylamino, propylamino, butylamino, dimethylamino and diethylamino groups;

carbamoyl groups, alkylcarbamoyl groups and dialkylcarbamoyl groups in which the or each alkyl part is independently selected from the group consisting of alkyl groups having from 1 to 4 carbon atoms, such as the carbamoyl, methylcarbamoyl, ethylcarbamoyl, propylcarbamoyl, isopropylcarbamoyl, dimethylcarbamoyl, diethylcarbamoyl, N-butyl-N-methylcarbamoyl, N-t-butyl-N-methylcarbamoyl, N-methyl-N-propylcarbamoyl, N-ethyl-N-propylcarbamoyl, dipropylcarbamoyl, diisopropylcarbamoyl, butylcarbamoyl, isobutylcarbamoyl, dibutylcarbamoyl and diisobutylcarbamoyl groups, especially the methylcarbamoyl, ethylcarbamoyl, propylcarbamoyl, butylcarbamoyl, dimethylcarbamoyl and diethylcarbamoyl groups; and alkanoylamino groups having from 1 to 5 carbon atoms, which may be straight or branched chain groups, such as the formamido, acetamido, propionamido, butyramido, isobutyramido, valeramido, isovaleramido and pivaloylamino groups, of which we prefer the formamido, acetamido, propionamido and butyramido groups.

Where $R^6$ represents an aliphatic hydrocarbon group having one or two carbon-carbon double or triple bonds, this is preferably an alkenyl group, an alkadienyl group or an alkynyl group, and may be a straight or branched chain group having from 2 to 8, preferably from 2 to 6, and more preferably 3 or 4, carbon atoms. Examples of the alkenyl groups include the vinyl, allyl, methallyl, 1-propenyl, isopropenyl, 1-butenyl, 2-butenyl, 3-butenyl, 1-pentenyl, 2-pentenyl, 3-pentenyl and 4-pentenyl groups, of which the allyl, methallyl, 1-propenyl, isopropenyl and butenyl groups are preferred, the allyl and 2-butenyl groups being most preferred. Examples of the alkadienyl groups include groups having from 3, preferably from 4, to 8 carbon atoms, such as the butadienyl and hexadienyl groups, more preferably the hexadienyl group. Examples of the alkynyl groups include the ethynyl, propargyl (2-propynyl), 1-propynyl, 1-butynyl, 2-butynyl, 3-butynyl, 1-pentynyl, 2-pentynyl, 3-pentynyl and 4-pentynyl groups, of which the propynyl and butynyl groups are preferred, the propargyl and 2-butynyl groups being most preferred.

Where $R^6$ represents an aryl, aryloxy or arylthio group, this may be as exemplified above in relation substituents (b).

Where $R^6$ represents a heterocyclic group, this may be a saturated or unsaturated group containing from 3 to 6 ring atoms, of which at least one, and preferably from 1 to 3, is a nitrogen, oxygen or sulfur atom. More preferably the group has from 0 to 3 such nitrogen atoms, 0, 1 or 2 such oxygen atoms and 0, 1 or 2 such sulfur atoms, provided that the total number of hetero-atoms is not less than 1 and does not exceed 3. More preferably, where the group has two or three hetero-atoms, at least one of these is a nitrogen atom, and the remaining one or two are selected from nitrogen, oxygen and sulfur hetero-atoms. Where the group is unsaturated, it may be non-aromatic or aromatic in character. The group may be monocyclic or it may be fused to one or two benzene rings to produce a bicyclic or tricyclic group, in which the heterocyclic part may be aromatic or non-aromatic in character. Examples of such groups include the oxiranyl, oxetanyl, aziridinyl, azetidinyl, thiranyl, thietanyl, furyl, thienyl, pyrrolyl, pyridyl, thiazolyl, isothiazolyl, oxazolyl, isoxazolyl, imidazolyl, pyrazolyl, pyranyl, pyrazinyl, pyridazinyl, pyrimidinyl, benzofuranyl, isobenzofuranyl, benzothienyl, isobenzothienyl, indolyl, quinolyl, isoquinolyl, quinazolinyl, quinoxalinyl, naphthyridynyl, xanthenyl, tetrahydrofuranyl, tetrahydrothienyl, pyrrolidinyl, thiazolidinyl, imidazolidinyl, imidazolinyl, oxazolinyl, oxazolidinyl, pyrazolidinyl, piperazyl, tetrahydropyrimidinyl, dihydropyridazinyl, morpholinyl, thiomorpholinyl, indolinyl, tetrahydroquinolyl, pyrrolidonyl, piperidonyl, pyridonyl, thianthrenyl, chromenyl, phenoxathiinyl, 2H-pyrrolyl, isoindolyl, 3H-indolyl, indazolyl, phthalazinyl, quinoxalinyl, quinazolinyl, cinnolinyl, carbazolyl, phenanthridinyl, acridinyl, perimidinyl, phenazinylphenothiazinyl, furazanyl, phenoxazinyl, isochromanyl, chromanyl, pyrazolinyl, indolinyl and isoindolinyl groups. Such groups may be unsubstituted or they may have an least one substituent selected from the group consisting of substituents (c), defined and exemplified above.

Where $R^1$ represents a group of formula

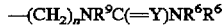

—$(CH_2)_nNR^9C(=Y)NR^6R^6$ the two groups $R^6$ attached to a single nitrogen atom may be the same or different and may be selected from those groups represented by $R^6$ and defined and exemplified above. Alternatively, the two groups $R^6$, together with the nitrogen atom to which they are attached, may form a nitrogen-containing heterocyclic group, which may optionally have an additional nitrogen, oxygen or sulfur hetero-atom; such a group may contain from 3 to 7 atoms in total (i.e. including the afore-mentioned nitrogen atom) and may be saturated or unsaturated. If it is unsaturated the unsaturation may be aromatic or non-aromatic in character, provided that the group has a nitrogen atom which can provide the nitrogen atom of the group —$NR^6R^6$. Examples of such groups include the aziridinyl, azetidinyl, pyrrolyl, imidazolyl, pyrazolyl, pyrrolidinyl, thiazolidinyl, imidazolidinyl, imidazolinyl, oxazolinyl, oxazolidinyl, pyrazolidinyl, piperazyl, tetrahydropyrimidinyl, dihydropyridazinyl, pyrrolidonyl, piperidonyl, pyridonyl, pyrazolinyl, azepinyl, perhydroazepinyl, oxazepinyl and thiazepinyl groups. Such groups may be unsubstituted or they may have at least one substituent selected from the group consisting of substituents (c), defined and exemplified above.

Where $R^1$ represents a group of formula

—$(CH_2)_nNR^9C(=Y)NR^6R^6$ the two groups $R^6$ attached to a single nitrogen atom may be the same or different and may be selected from those groups represented by $R^6$ and defined and exemplified above. Alternatively, the two groups $R^6$, together with the nitrogen atom to which they are attached, may form a nitrogen-containing heterocyclic group, which may optionally have an additional nitrogen, oxygen or sulfur hetero-atom; such a group may contain from 3 to 7 atoms in total (i.e. including the afore-mentioned nitrogen atom) and may be saturated or unsaturated, as defined and exemplified in the preceding paragraph. Alternatively, two of the symbols $R^6$ attached to different nitrogen atoms may form a heterocyclic ring containing at least two nitrogen atoms and optionally another hetero-atom selected from the group consisting of nitrogen, oxygen and sulfur hetero-atoms. Examples of such groups include the divalent groups derived by removal of a hydrogen atom from each of the two adjacent nitrogen atoms of the ring systems: diaziridine, diazete, diazetidine, pyrazolidine, pyrazoline, 1,2-dihydropyridazine, 1,2,3,4-tetrahydropyridazine, 1,2,5,6-tetrahydropyridazine, perhydropyridazine, 1,2-dihydro-1,2-diazepine and perhydro-1,2-diazepine.

Where $R^7$ represents an alkyl group having from 1 to 4 carbon atoms, this may be as defined and exemplified above in relation to the groups which may be represented by $R^1$.

Where $R^7$ represents an aralkyl group, the alkyl part has from 1 to 4 carbon atoms and may be any of the alkyl groups exemplified above. The aryl part or parts has or have from 6 to 10 carbon atoms in its ring and again, may be any of the aryl groups exemplified above. There may be from 1 to 3 such aryl groups. Examples of such aralkyl groups include the benzyl, phenethyl, α-methylbenzyl, 1-phenylpropyl, 2-phenylpropyl, 3-phenylpropyl, 4-phenylbutyl, benzhydryl and trityl groups, of which the benzyl and phenethyl groups are preferred.

Where X represents an alkanoyloxy group, it contains from 1 to 5 carbon atoms and may be a straight or branched chain group. Examples of such groups include the formyloxy, acetoxy, propionyloxy, butyryloxy, isobutyryloxy, valeryloxy, isovaleryloxy and pivaloyloxy groups. Such groups may be unsubstituted, or they may have at least one substituent selected from the group consisting of substituents (d), defined above and exemplified below.

Examples of groups and atoms which may be represented by substituents (d) include:

halogen atoms and alkoxy groups having from 1 to 4 carbon atoms, as exemplified in relation to substituents (a);

alkoxycarbonyl groups having from 2 to 5 carbon atoms, as exemplified in relation to substituents (b); and carboxy groups.

In general, in the discussion herein, where reference is made to a substituted group, there is no particular restriction on the number of substituents, except such as may be imposed by the number of substitutable positions, or possibly by steric constraints, each of which is well recognised by those skilled in the art. However, as a general rule, we normally find it convenient to have no more than 3 such substituents, and sometimes fewer, i.e. 1, 2 or 3. More preferably, the number of the substituents is 1, 2 or 3 where the substituent is a halogen atom, and 1 in other cases.

Where $R^7$ represents a hydrogen atom or substituent (d) is a carboxy group, the compounds can form salts with various sorts of bases. Such salts includes, for example: salts with an alkali metal, such as lithium, sodium or potassium; salts with an alkaline earth metal, such as calcium or barium; salts with another metal, such as magnesium or aluminum; and salts with an organic amine, such as triethylamine or triethanolamine.

Of the compounds of formula (I) of the present invention, representative preferred classes are as follows:

(1) those wherein $R^1$ represents: a hydrogen atom, an alkyl group having from 1 to 3 carbon atoms, such as the methyl, ethyl, propyl and isopropyl groups; an alkoxy group having from 1 to 3 carbon atoms, such as the methoxy, ethoxy, propoxy and isopropoxy groups; the fluorine and chlorine atoms; and the nitro and amino groups;

(2) those wherein $R^1$ represents a group of formula —$NR^{9a}COR^{6a}$ wherein:

$R^{9a}$ represents a hydrogen atom or a methyl group; and $R^{6a}$ represents a hydrogen atom, an alkyl group having from 1 to 4 carbon atoms, such as the methyl, ethyl, propyl, isopropyl and butyl groups; a cycloalkyl group having from 3 to 5 carbon atoms, such as the cyclopropyl, cyclobutyl and cyclopentyl groups; an alkyl group having from 1 to 3 carbon atoms, and substituted with a halogen atom, a cyano group, an alkoxy group having from 1 to 3 carbon atoms, an alkylthio group having from 1 to 3 carbon atoms, a cyanomethylthio group or a phenoxy group, such as the fluoromethyl, bromoethyl, difluoromethyl, cyanomethyl, cyanopropyl, methoxymethyl, ethoxymethyl, methylthiomethyl, cyatomethylthiomethyl and phenoxymethyl groups; an alkenyl group having from 2 to 4 carbon atoms, such as the vinyl and allyl groups; a phenyl group; a phenyl group substituted with an alkyl group having from 1 to 3 carbon atoms, an alkoxy group having from 1 to 3 carbon atoms, a halogen atom or a nitro group, such as the tolyl, methoxyphenyl, fluorophenyl and nitrophenyl groups; a pyridyl group; a pyrimidyl group; a pyrazinyl group; a furyl group; or a thienyl group;

(3) those wherein $R^1$ represents a group of formula —$NR^{9a}COCOR^{6b}$ wherein:

$R^{9a}$ represents a hydrogen atom or a methyl group; and $R^{6b}$ represents a hydrogen atom, an alkyl group having from 1 to 4 carbon atoms, such as the methyl, ethyl, propyl, isopropyl and butyl groups; a cycloalkyl group having from 3 to 5 carbon atoms, such as the cyclopropyl, cyclobutyl and cyclopentyl groups; an alkenyl group having from 2 to 4 carbon atoms, such as the vinyl and allyl groups; a phenyl group; or a phenyl group substituted with an alkyl group having from 1 to 3 carbon atoms, an alkoxy group having from 1 to 3 carbon atoms, a halogen atom or a nitro group, such as the tolyl, methoxyphenyl, fluorophenyl and nitrophenyl groups;

(4) those wherein $R^1$ represents a group of formula —$NR^{9a}C(=Y)YR^{6c}$ wherein:

$R^{9a}$ represents a hydrogen atom or a methyl group;

Y represents an oxygen atom; and $R^{6c}$ represents: an alkyl group having from 1 to 4 carbon atoms, such as the methyl, ethyl, propyl, isopropyl and butyl groups; an alkyl group having from 1 to 4 carbon atoms, and substituted with a halogen atom or an alkoxy group having from 1 to 3 carbon atoms, such as the fluoroethyl, trichloroethyl, methoxyethyl and ethoxyethyl groups; a vinyl group; an allyl group; a benzyl group; a methoxybenzyl group; nitrobenzyl group; a furfuryl group; a thenyl group; or a phenyl group;

(5) those wherein $R^1$ represents a group of formula —$NR^{9a}C(=Y)NR^{6d}R^{6e}$ wherein:

$R^{9a}$ represents a hydrogen atom or a methyl group;

Y represents an oxygen atom or a sulfur atom; and $R^{6d}$ and $R^{6e}$ are independently selected from the group consisting of: hydrogen atoms; alkyl groups having from 1 to 4 carbon atoms, such as the methyl, ethyl, propyl, isopropyl and butyl groups; cycloalkyl groups having from 3 to 6 carbon atoms, such as the cyclopropyl, cyclobutyl, cyclopentyl and cyclohexyl groups; phenyl groups; phenyl groups substituted with an alkyl group having from 1 to 3 carbon atoms, an alkoxy group having from 1 to 3 carbon atoms, a halogen atom or a nitro group, such as the tolyl, methoxyphenyl, fluorophenyl and nitrophenyl groups; or $R^{6d}$ and $R^{6e}$, together with the nitrogen atom to which they are attached, form a piperidine, piperazine, morpholine, pyrrolidine, or aziridine ring;

(6) those wherein $R^1$ represents a group of formula —$NR^{9a}C(=Y)NR^{6f}NR^{6g}R^{6h}$ wherein:

$R^{9a}$ represents a hydrogen atom or a methyl group;

Y represents an oxygen atom or a sulfur atom; and $R^{6f}$, $R^{6g}$ and $R^{6h}$ are independently selected from the group consisting of: hydrogen atoms, alkyl groups having from 1 to 4 carbon atoms, such as the methyl, ethyl, propyl, isopropyl and butyl groups; cycloalkyl groups having from 3 to 6 carbon atoms, such as the cyclopropyl, cyclobutyl, cyclopentyl and cyclohexyl groups; phenyl groups; and phenyl groups substituted with an alkyl group having from 1 to 3 carbon atoms, an alkoxy group having from 1 to 3 carbon atoms, a halogen atom or a nitro group, such as the tolyl, methoxyphenyl, fluorophenyl and nitrophenyl groups; or $R^{6g}$ and $R^{6h}$ together with the nitrogen atom to which they are attached, form a piperidine, piperazine, morpholine, pyrrolidine or aziridine ring; or $R^{6f}$ and $R^{6g}$, together with the nitrogen atoms to which they are attached, form a pyrazolidine or tetrahydropyridazine ring;

(7) those wherein $R^1$ represents a group of formula —$NR^{9a}C(=Y)NR^{6f}NHZ$ wherein:

$R^{9a}$ represents a hydrogen atom or a methyl group;

Y represents an oxygen atom or a sulfur atom;

$R^{6f}$ represents an alkyl group having from 1 to 4 carbon atoms, such as the methyl, ethyl, propyl, isopropyl and butyl groups, or a cycloalkyl group having from 3 to 6 carbon atoms, such as the cyclopropyl, cyclobutyl, cyclopentyl and cyclohexyl groups;

Z represents a group of formula —$COOR^{7a}$ (wherein: R7a represents an alkyl group having from 1 to 4 carbon atoms, such as the methyl, ethyl, propyl, isopropyl and butyl groups, or a cycloalkyl group having from 3 to 6 carbon atoms, such as the cyclopropyl, cyclobutyl, cyclopentyl and cyclohexyl groups; or a benzyl group); a group of formula —COR$^{6k}$ (wherein R$^{6k}$ represents: an alkyl group having from 1 to 4 carbon atoms, such as the methyl, ethyl, propyl, isopropyl and butyl groups; a cycloalkyl group having from 3 to 6 carbon atoms, such as the cyclopropyl, cyclobutyl, cyclopentyl and cyclohexyl groups; a phenyl group; or a phenyl group substituted with an alkyl group having from 1 to 3 carbon atoms, an alkoxy group having from 1 to 3 carbon atoms, a halogen atom or a nitro group, such as the tolyl, methoxyphenyl, fluorophenyl and nitrophenyl groups), or a group of formula —SO$_2$R$^{6m}$ (wherein R$^{6m}$ represents: an alkyl group having from 1 to 4 carbon atoms, such as the methyl, ethyl, propyl, isopropyl and butyl groups; a phenyl group; or a phenyl group substituted with an alkyl group having from 1 to 3 carbon atoms, an alkoxy group having from 1 to 3 carbon atoms, a halogen atom or a nitro group, such as the tolyl, methoxyphenyl, fluorophenyl and nitrophenyl groups);

(8) those wherein R$^1$ represents a group of formula —NR$^{9a}$C(=NR$^{11a}$)NHR$^{11b}$
wherein:

R$^{9a}$ represents a hydrogen atom or a methyl group;

R$^{11a}$ and R$^{11b}$ are independently selected from the group consisting of: hydrogen atoms; alkyl groups having from 1 to 4 carbon atoms, such as the methyl, ethyl, propyl, isopropyl and butyl groups; phenyl groups; and phenyl groups substituted with an alkyl group having from 1 to 3 carbon atoms, an alkoxy group having from 1 to 3 carbon atoms, a halogen atom or a nitro group, such as the tolyl, methoxyphenyl, fluorophenyl and nitrophenyl groups; groups of formula —COOR$^{7b}$ (wherein R$^{7b}$ represents: an alkyl group having from 1 to 4 carbon atoms, such as the methyl, ethyl, propyl, isopropyl and butyl groups; a cycloalkyl group having from 3 to 6 carbon atoms, such as the cyclopropyl, cyclobutyl, cyclopentyl and cyclohexyl groups; or a benzyl group); groups of formula —COR$^{6n}$ (wherein R$^{6n}$ represents: an alkyl group having from 1 to 4 carbon atoms, such as the methyl, ethyl, propyl, isopropyl and butyl groups; a cycloalkyl group having from 3 to 6 carbon atoms, such as the cyclopropyl, cyclobutyl, cyclopentyl and cyclohexyl groups; phenyl groups; and phenyl groups substituted with an alkyl group having from 1 to 3 carbon atoms, an alkoxy group having from 1 to 3 carbon atoms, a halogen atom or a nitro group, such as the tolyl, methoxyphenyl, fluorophenyl and nitrophenyl groups);

(9) those wherein R$^1$ represents a group of formula —NR$^{9a}$C(=NR$^{11c}$)R$^{6p}$
wherein:

R$^{9a}$ represents a hydrogen atom or a methyl group;

R$^{11c}$ represents: a hydrogen atom; an alkyl group having from 1 to 4 carbon atoms, such as the methyl, ethyl, propyl, isopropyl and butyl groups; a phenyl group; a phenyl group substituted with an alkyl group having from 1 to 3 carbon atoms, an alkoxy group having from 1 to 3 carbon atoms, a halogen atom or a nitro group, such as the tolyl, methoxyphenyl, fluorophenyl and nitrophenyl groups; groups of formula —COOR$^{7c}$ (wherein R$^{7c}$ represents: an alkyl group having from 1 to 4 carbon atoms, such as the methyl, ethyl, propyl, isopropyl and butyl groups; a cycloalkyl group having from 3 to 6 carbon atoms, such as the cyclopropyl, cyclobutyl, cyclopentyl and cyclohexyl groups; or a benzyl group); a group of formula —COR$^{6q}$ (wherein R$^{6q}$ represents: an alkyl group having from 1 to 4 carbon atoms, such as the methyl, ethyl, propyl, isopropyl and butyl groups; a cycloalkyl group having from 3 to 6 carbon atoms, such as the cyclopropyl, cyclobutyl, cyclopentyl and cyclohexyl groups; a phenyl group; or a phenyl group substituted with an alkyl group having from 1 to 3 carbon atoms, an alkoxy group having from 1 to 3 carbon atoms, a halogen atom or a nitro group, such as the tolyl, methoxyphenyl, fluorophenyl and nitrophenyl groups);

R$^{6p}$ represents: an alkyl group having from 1 to 4 carbon atoms, such as the methyl, ethyl, propyl, isopropyl and butyl groups; or a cycloalkyl group having from 3 to 6 carbon atoms, such as the cyclopropyl, cyclobutyl, cyclopentyl and cyclohexyl groups; a phenyl group; or a phenyl group substituted with an alkyl group having from 1 to 3 carbon atoms, an alkoxy group having from 1 to 3 carbon atoms, a halogen atom or a nitro group, such as the tolyl, methoxyphenyl, fluorophenyl and nitrophenyl groups);

(10) those wherein R$^1$ represents a group formula —NR$^{9a}$SO$_m$R$^{6r}$
wherein:

R$^{9a}$ represents a hydrogen atom or a methyl group;

R$^{6r}$ represents: an alkyl group having from 1 to 4 carbon atoms, such as the methyl, ethyl, propyl, isopropyl and butyl groups; an alkyl group substituted with a cyano group, such as the cyanomethyl and cyanoethyl groups; a phenyl group; or a phenyl group substituted with an alkyl group having from 1 to 3 carbon atoms, an alkoxy group having from 1 to 3 carbon atoms, a halogen atom or a nitro group, such as the tolyl, methoxyphenyl, fluorophenyl and nitrophenyl groups; and m is 1 or 2;

(11) compounds as defined in any one of (2) to (10) above, wherein A represents a group of formula:

wherein R$^2$, R$^3$ and R$^4$ are independently selected from the group consisting of hydrogen atoms and methyl groups;

(12) compounds as defined in any one of (2) to (10) above, wherein A represents a group of formula:

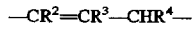

wherein R$^2$, R$^3$ and R$^4$ are independently selected from the group consisting of hydrogen atoms and methyl groups;

(13) compounds as defined in any one of (2) to (10) wherein A represents a group of formula:

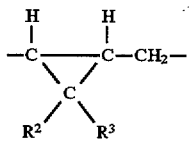

wherein R$^2$ and R$^3$ are independently selected from the group consisting of hydrogen atoms, chlorine atoms and methyl groups;

(14) compounds as defined in (11) above, where the substituent R$^1$ is at the meta or the ortho position;

(15) compounds as defined in (12) above, where the substituent $R^1$ is at the meta or ortho position;

(16) those wherein $R^5$ represents an ethyl group;

(17) mixtures of a compound wherein $R^5$ represents an ethyl group and the corresponding compound wherein $R^5$ represents a methyl group;

(18) those wherein $R^3$ and $R^4$ each represent hydrogen atoms; and

(19) those wherein X represents a hydroxy group.

Typical examples of compounds of formula (I) of the present invention are as follows:

13-(3-Phenylpropoxy)milbemycin $A_4$,
13-(3-Phenylpropoxy)milbemycin $A_3$,
13-(3-Phenylpropoxy)milbemycin D,
13-Deoxy-13-(3-phenylpropoxy)-22,23-dihydroavermectin $B_{1a}$ aglycone,
13-Cinnamyloxymilbemycin $A_4$,
13-Cinnamyloxymilbemycin $A_3$,
13-Cinnamyloxymilbemycin D,
13-Deoxy-13-cinnamyloxy-22,23-dihydroavermectin $B_{1a}$ aglycone,
13-(3-Phenylbutyloxy)milbemycin $A_4$,
13-(3-Bromo-3-phenylpropoxy)milbemycin $A_4$,
13-(3-Methoxy-3-phenylpropoxy)milbemycin $A_4$,
13-(2-Phenylcyclopropylmethoxy)milbemycin $A_4$,
13-(3,3-Dichloro-2-phenylcyclopropylmethoxy) milbemycin $A_4$,
13-(3,3-Dimethyl-2-phenylcyclopropylmethoxy) milbemycin $A_4$,
13-(β-Methylcinnamyloxy)milbemycin $A_4$,
13-(β-Bromocinnamyloxy)milbemycin $A_4$,
13-(γ-Methylcinnamyloxy)milbemycin $A_4$,
13-(γ-Methoxycinnamyloxy)milbemycin $A_4$,
13-[(Z)-3-Phenyl-2-methylpropenyloxy]milbemycin $A_4$,
13-[(Z)-3-Phenyl-3-methylpropenyloxy]milbemycin $A_4$,
13-[3-(4-Nitrophenyl)propoxy]milbemycin $A_4$,
13-[3-(3-Nitrophenyl)propoxy]milbemycin $A_4$,
13-[3-(2-Nitrophenyl)propoxy]milbemycin $A_4$,
13-[3-(4-Aminophenyl)propoxy]milbemycin $A_4$,
13-[3-(3-Aminophenyl)propoxy]milbemycin $A_4$,
13-[3-(2-Aminophenyl)propoxy]milbemycin $A_4$,
13-[3-(4-Acetamidophenyl)propoxy]milbemycin $A_4$,
13-[3-(3-Acetamidophenyl)propoxy]milbemycin $A_4$,
13-[3-(2-Acetamidophenyl)propoxy]milbemycin $A_4$,
13-[3-(3-Cyanoacetamidophenyl)propoxy]milbemycin $A_4$,
13-[3-(2-Cyanoacetamidophenyl)propoxy]milbemycin $A_4$,
13-[3-(4-Ethoxycarbonylaminophenyl)propoxy] milbemycin $A_4$,
13-[3-(3-Ethoxycarbonylaminophenyl)propoxy] milbemycin $A_4$,
13-[3-(2-Ethoxycarbonylaminophenyl)propoxy] milbemycin $A_4$,
13-[3-(4-Isopropoxycarbonylaminophenyl)propoxy] milbemycin $A_4$,
13-[3-(3-Isopropoxycarbonylaminophenyl)propoxy] milbemycin $A_4$,
13-[3-(2-isopropoxycarbonylaminophenyl)propoxy] milbemycin $A_4$,
13-[3-(4-Methanesulfonylaminophenyl)propoxy] milbemycin $A_4$,
13-[3-(3-Methanesulfonylaminophenyl)propoxy] milbemycin $A_4$,
13-[3-(2-Methanesulfonylaminophenyl)propoxy] milbemycin $A_4$,
13-{3-[4-(3-Methylureido)phenyl]propoxy}milbemycin $A_4$,
13-{3-[3-(3-Methylureido)phenyl]propoxy}milbemycin $A_4$,
13-{3-[2-(3-Methylureido)phenyl]propoxy}milbemycin $A_4$,
13-{3-[3-(3-Cyclopropylureido)phenyl] propoxy}milbemycin $A_4$,
13-{3-[4-(3-Thiomethylureido)phenyl] propoxy}milbemycin $A_4$,
13-{3-[3-(3-Methylthioureido)phenyl] propoxy}milbemycin $A_4$,
13-{3-[2-(3-Methylthioureido)phenyl] propoxy}milbemycin $A_4$,
13-{3-[4-(3-Phenylureido)phenyl]propoxy}milbemycin $A_4$,
13-{3-[3-(3-Phenylureido)phenyl]propoxy}milbemycin $A_4$,
13-{3-[2-(3-Phenylureido)phenyl]propoxy}milbemycin $A_4$,
13-{3-[4-(3-p'-Toluylureido)phenyl] propoxy}milbemycin $A_4$,
13-{3-[3-(3-p'-Toluylureido)phenyl] propoxy}milbemycin $A_4$,
13-{3-[2-(3-p'-Toluylureido)phenyl] propoxy}milbemycin $A_4$,
13-(3-Nitrocinnamyloxy)milbemycin $A_4$,
13-(2-Nitrocinnamyloxy)milbemycin $A_4$,
13-(3-Methoxycinnamyloxy)milbemycin $A_4$,
13-(4-Aminocinnamyloxy)milbemycin $A_4$,
13-(3-Aminocinnamyloxy)milbemycin $A_4$,
13-(2-Aminocinnamyloxy)milbemycin $A_4$,
13-(4-Methylaminocinnamyloxy)milbemycin $A_4$,
13-(4-Acetamidocinnamyloxy)milbemycin $A_4$,
13-(3-Acetamidocinnamyloxy)milbemycin $A_4$,
13-(3-Acetamidocinnamyloxy)milbemycin $A_4$ 5-oxime,
13-(2-Acetamidocinnamyloxy)milbemycin $A_4$,
13-[3-(N-Acetyl-N-methylamino)cinnamyloxy] milbemycin $A_4$,
13-(3-Formamidocinnamyloxy)milbemycin $A_4$,
13-(3-Propionamidocinnamyloxy)milbemycin $A_4$,
13-(3-Butyramidocinnamyloxy)milbemycin $A_4$,
13-(3-Chloroacetamidocinnamyloxy)milbemycin $A_4$,
13-(3-Methoxyacetamidocinnamyloxy)milbemycin $A_4$,
13-[3-(N-Methoxyacetyl-N-methylamino)cinnamyloxy] milbemycin $A_4$,
13-(3-Fluoroacetamidocinnamyloxy)milbemycin $A_4$,
13-(3-Difluoroacetamidocinnamyloxy)milbemycin $A_4$,
13-(3-Trifluoroacetamidocinnamyloxy)milbemycin $A_4$,
13-(3-Cyanoacetamidocinnamyloxy)milbemycin $A_4$,
13-[3-(N-Cyanoacetyl-N-methylamino)cinnamyloxy] milbemycin $A_4$,
13-[3-(2-Cyanopropionylamino)cinnamyloxy] milbemycin $A_4$, 13-(3-Methoxalylaminocinnamyloxy)milbemycin $A_4$,
13-(3-Pyruvoylaminocinnamyloxy)milbemycin $A_4$,
13-(3-Methoxycarbonylacetamidocinnamyloxy) milbemycin $A_4$,
13-(3-Phenylacetamidocinnamyloxy)milbemycin $A_4$,
13-(3-Phenoxyacetamidocinnamyloxy)milbemycin $A_4$,
13-(3-(3-Acryloylaminocinnamyloxy)milbemycin $A_4$,
13-(3-Methacryloylaminocinnamyloxy)milbemycin $A_4$,
13-(3-Tetrolylaminocinnamyloxy)milbemycin $A_4$,
13-[3-(Cinnamoylamino)cinnamyloxy]milbemycin $A_4$,
13-(3-Cyclopropylcarbonylaminocinnamyloxy) milbemycin $A_4$,
13-(3-Cyclobutylcarbonylaminocinnamyloxy) milbemycin $A_4$,
13-(3-Cyclopentylcarbonylaminocinnamyloxy) milbemycin $A_4$,
13-(3-Cyclohexanecarbonylaminocinnamyloxy) milbemycin $A_4$,
13-(3-Benzoylaminocinnamyloxy)milbemycin $A_4$,
13-[3-(p-Toluoylamino)cinnamyloxy]milbemycin $A_4$,
13-[3-(p-Anisoylamino)cinnamyloxy]milbemycin $A_4$,
13-[3-(4-Fluorobenzoylamino)cinnamyloxy]milbemycin $A_4$,
13-[3-(4-Chlorobenzoylamino)cinnamyloxy]milbemycin $A_4$,
13-[3-(4-Aminobenzoylamino)cinnamyloxy]milbemycin $A_4$,
13-[3-(4-Acetamidobenzoylamino)cinnamyloxy] milbemycin $A_4$,
13-[3-(4-Cyanobenzoylamino)cinnamyloxy]milbemycin $A_4$,
13-[3-(4-Methoxycarbonylbenzoylamino)cinnamyloxy] milbemycin $A_4$,
13-[3-(2-Furoylamino)cinnamyloxy]milbemycin $A_4$,
13-[3-(2-Thenoylamino)cinnamyloxy]milbemycin $A_4$,
13-[3-(Nicotinoylamino)cinnamyloxy]milbemycin $A_4$,
13-[3-(Isonicotinoylamino)cinnamyloxy]milbemycin $A_4$,
13-[3-(2-Pyridylcarbonylamino)cinnamyloxy] milbemycin $A_4$,
13-[3-(4-Piperidinocarbonylamino)cinnamyloxy] milbemycin $A_4$,
13-[3-(4-Pyrazin-2-ylcarbonylamino)cinnamyloxy] milbemycin $A_4$,
13-[3-(Glycylamino)cinnamyloxy]milbemycin $A_4$,
13-[3-($\underline{N}$-Acetylglycylamino)cinnamyloxy]milbemycin $A_4$,
13-[3-($\underline{N}$-Ethoxycarbonylglycylamino)cinnamyloxy] milbemycin $A_4$,
13-{3-[(3-Methylureido)acetamido] cinnamyloxy}milbemycin $A_4$,
13-[3-(3-Oxo-1,2,4-triazolo[4,3-a]pyridin-2-ylcarbonylamino]cinnamyloxy]milbemycin $A_4$,
13-(3-Methoxycarbonylaminocinnamyloxy)milbemycin $A_4$,
13-{3-[($\underline{N}$-Methoxycarbonyl)methylamino] cinnamyloxy}- milbemycin $A_4$,
13-(3-Methoxycarbonylaminomethylcinnamyloxy) milbemycin $A_4$,
13-(3-Ethoxycarbonylaminocinnamyloxy)milbemycin $A_4$,
13-{3-[($\underline{N}$-Ethoxycarbonyl)methylamino] cinnamyloxy}milbemycin $A_4$,
13-(2-Ethoxycarbonylaminocinnamyloxy)milbemycin $A_4$,
13-(4-Ethoxycarbonylaminocinnamyloxy)milbemycin $A_4$,
13-(3-Ethoxycarbonylaminocinnamyloxy)milbemycin D,
13-Deoxy-13-(3-ethoxycarbonylaminocinnamyloxy)-22,23-dihydroavermectin $B_{1a}$ aglycone
13-(3-Propoxycarbonylaminocinnamyloxy)milbemycin $A_4$,
13-(3-Isopropoxycarbonylaminocinnamyloxy) milbemycin $A_4$,
13-(3-Butoxycarbonylaminocinnamyloxy)milbemycin $A_4$,
13-(3-Cyclopropyloxycarbonylaminocinnamyloxy) milbemycin $A_4$,
13-{3-($\underline{N}$-Cyclopropylcarbonyl-$\underline{N}$-methylamino) cinnamyloxy}milbemycin $A_4$,
13-(3-Cyclobutyloxycarbonylaminocinnamyloxy) milbemycin $A_4$,
13-{3-($\underline{N}$-Cyclobutylcarbonyl-$\underline{N}$-methylamino) cinnamyloxy}milbemycin $A_4$,
13-(3-Cyclopentyloxycarbonylaminocinnamyloxy) milbemycin $A_4$,
13-(3-Cyclohexyloxycarbonylaminocinnamyloxy) milbemycin $A_4$,
13-(3-Vinyloxycarbonylaminocinnamyloxy)milbemycin $A_4$,
13-(3-Allyloxycarbonylaminocinnamyloxy)milbemycin $A_4$,
13-(3-Cyclohexyloxycarbonylaminocinnamyloxy) milbemycin $A_4$,
13-(3-Benzyloxycarbonylaminocinnamyloxy) milbemycin $A_4$,
13-[3-(4-Nitrobenzyloxycarbonylamino)cinnamyloxy] milbemycin $A_4$,
13-[3-(4-Methoxybenzyloxycarbonylamino) cinnamyloxy]milbemycin $A_4$,
13-(3-Methoxycarbonylaminomethylcinnamyloxy) milbemycin $A_4$,
13-(3-Ethoxycarbonylaminomethylcinnamyloxy) milbemycin $A_4$,
13-(3-Ethylthiocarbonylaminocinnamyloxy)milbemycin $A_4$,
13-(3-Ethylthiothiocarbonylaminocinnamyloxy) milbemycin $A_4$,
13-(3-Methanesulfonylaminocinnamyloxy)milbemycin $A_4$,
13-{3-[(N-Methanesulfonyl)methylamino] cinnamyloxy}milbemycin $A_4$,
13-(3-Ethanesulfonylaminocinnamyloxy)milbemycin $A_4$,
13-(3-Propanesulfonylaminocinnamyloxy)milbemycin $A_4$,
13-(3-Cyanomethanesulfonylaminocinnamyloxy) milbemycin $A_4$,
13-(3-Benzenesulfonylaminocinnamyloxy)milbemycin $A_4$,
13-[3-(4-Methylbenzenesulfonylamino)cinnamyloxy] milbemycin $A_4$,
13-[3-(4-Methoxybenzenesulfonylamino)cinnamyloxy] milbemycin $A_4$, 13-(3-Benzenesulfinylaminocinnamyloxy)milbemycin $A_4$,
13-[3-(3-Methylureido)cinnamyloxy]milbemycin $A_4$,
13-[2-(3-Methylureido)cinnamyloxy]milbemycin $A_4$,
13-[4-(3-Methylureido)cinnamyloxy]milbemycin $A_4$,
13-[3-(3-Methylureido)cinnamyloxy]milbemycin $A_4$ 5-oxime,
13-[3-(3-Methylureido)cinnamyloxy]milbemycin D,
13-Deoxy-13-[3-(3-methylureido)cinnamyloxy]-22,23-dihydroavermectin $B_{1a}$ aglycone
13-[3-(3-Chloromethylureido)cinnamyloxy]milbemycin $A_4$,
13-(3-Ureidocinnamyloxy)milbemycin $A_4$,
13-[3-(1,3-Dimethylureido)cinnamyloxy]milbemycin $A_4$,
13-[3-(1,3,3-Trimethylureido)cinnamyloxy]milbemycin $A_4$,
13-[3-(3,3-Dimethylureido)cinnamyloxy]milbemycin $A_4$,
13-[3-(3-Ethylureido)cinnamyloxy]milbemycin $A_4$,
13-[3-(3-Methoxycarbonylmethylureido)cinnamyloxy]milbemycin $A_4$,
13-{3-[3-(2-Chloroethyl)ureido]cinnamyloxy}milbemycin $A_4$,
13-{3-[3-(2-Hydroxyethyl)ureido]cinnamyloxy}milbemycin $A_4$,
13-{3-[3-(2-Mercaptoethyl)ureido]cinnamyloxy}milbemycin $A_4$,
13-[3-(3-Propylureido)cinnamyloxy]milbemycin $A_4$,
13-[3-(3-Isopropylureido)cinnamyloxy]milbemycin $A_4$,
13-[3-(3-Butylureido)cinnamyloxy]milbemycin $A_4$,
13-[3-(3-Cyclopropylureido)cinnamyloxy]milbemycin $A_4$,
13-[3-(3-Cyclopropyl-1-methylureido)cinnamyloxy]milbemycin $A_4$,
13-[3-(3-Cyclobutylureido)cinnamyloxy]milbemycin $A_4$,
13-[3-(3-Cyclobutyl-1-methylureido)cinnamyloxy]milbemycin $A_4$,
13-[3-(3-Cyclohexylureido)cinnamyloxy]milbemycin $A_4$,
13-[3-(3-Allylureido)cinnamyloxy]milbemycin $A_4$,
13-[3-(3-Phenylureido)cinnamyloxy]milbemycin $A_4$,
13-[3-(3-Phenylureido)cinnamyloxy]milbemycin D,
13-Deoxy-13-[3-(3-phenylureido)cinnamyloxy]-22,23-dihydroavermectin $B_{1a}$ aglycone
13-{3-[3-(4-Toluyl)ureido]cinnamyloxy}milbemycin $A_4$,
13-{3-[3-(4-Fluorophenyl)ureido]cinnamyloxy}milbemycin $A_4$,
13-{3-[3-(3-Fluorophenyl)ureido]cinnamyloxy}milbemycin $A_4$,
13-{3-[3-(2-Fluorophenyl)ureido]cinnamyloxy}milbemycin $A_4$,
13-{3-[3-(4-Chlorophenyl)ureido]cinnamyloxy}milbemycin $A_4$,
13-{3-[3-(4-Nitrophenyl)ureido]cinnamyloxy}milbemycin $A_4$,
13-{3-[3-(4-Cyanophenyl)ureido]cinnamyloxy}milbemycin $A_4$,
13-{3-[3-(4-Methoxyphenyl)ureido]cinnamyloxy}milbemycin $A_4$,
13-{3-[3-(4-Aminophenyl)ureido]cinnamyloxy}milbemycin $A_4$,
13-{3-[3-(4-Acetamidophenyl)ureido]cinnamyloxy}milbemycin $A_4$,
13-{3-[3-(1-Naphthyl)ureido]cinnamyloxy}milbemycin $A_4$,
13-{3-[3-(2-Pyridyl)ureido]cinnamyloxy}milbemycin $A_4$,
13-{3-[3-(2-Thiazolinyl)ureido]cinnamyloxy}milbemycin $A_4$,
13-{3-[3-(2-Thiazolyl)ureido]cinnamyloxy}milbemycin $A_4$,
13-[3-(3-Propionylureido)cinnamyloxy]milbemycin $A_4$,
13-[3-(3-Benzoylureido)cinnamyloxy]milbemycin $A_4$,
13-[3-(3-Methanesulfonylureido)cinnamyloxy]milbemycin $A_4$,
13-[3-(Morpholinocarbonylamino)cinnamyloxy]milbemycin $A_4$,
13-[3-(3-Methylureidomethyl)cinnamyloxy]milbemycin $A_4$,
13-[3-(3-Phenylureidomethyl)cinnamyloxy]milbemycin $A_4$,
13-[3-(3-Methylthioureido)cinnamyloxy]milbemycin $A_4$,
13-[3-(3-Methylthioureido)cinnamyloxy]milbemycin D,
13-Deoxy-13-[3-(3-methylthioureido)cinnamyloxy]-22,23-dihydroavermectin $B_{1a}$ aglycone
13-[3-(1,3-Dimethylthioureido)cinnamyloxy]milbemycin $A_4$,
13-[3-(3-Ethylthioureido)cinnamyloxy]milbemycin $A_4$,
13-[3-(3-Propylthioureido)cinnamyloxy]milbemycin $A_4$,
13-[3-(3-Isopropylthioureido)cinnamyloxy]milbemycin $A_4$,
13-[3-(3-Allylthioureido)cinnamyloxy]milbemycin $A_4$,
13-[3-(3-Phenylthioureido)cinnamyloxy]milbemycin $A_4$,
13-[3-(Formimidoylamino)cinnamyloxy]milbemycin $A_4$,
13-[3-(Acetimidoylamino)cinnamyloxy]milbemycin $A_4$,
13-[3-(Benzimidoylamino)cinnamyloxy]milbemycin $A_4$,
13-[3-(Carbazoylamino)cinnamyloxy]milbemycin $A_4$,
13-[3-(3,3-Dimethylcarbazoylamino)cinnamyloxy]milbemycin $A_4$,
13-{3-[N-(3,3-Dimethylcarbazoyl)methylamino]cinnamyloxy}milbemycin $A_4$,
13-[3-(3-Phenylcarbazoylamino)cinnamyloxy]milbemycin $A_4$,
13-{3-[3-(2-Pyridyl)carbazoylamino]cinnamyloxy}milbemycin $A_4$,
13-[3-(3-Acetylcarbazoylamino)cinnamyloxy]milbemycin $A_4$,
13-[3-(3-Benzoylcarbazoylamino)cinnamyloxy]milbemycin $A_4$,
13-[3-(3-Morpholinoureido)cinnamyloxy]milbemycin $A_4$,
13-{3-[3-(Hexahydro-1H-azepin-1-yl)ureido]cinnamyloxy}milbemycin $A_4$,
13-{3-[3-(Methoxycarbonyl)guanidino]cinnamyloxy}milbemycin A4, and
13-{3-[2,3-Bis(methoxycarbonyl)guanidino]cinnamyloxy}milbemycin $A_4$, Of the compounds listed above, the preferred compounds are:

13-(3-Aminocinnamyloxy)milbemycin $A_4$
13-(2-Aminocinnamyloxy)milbemycin $A_4$
13-(3-Acetamidocinnamyloxy)milbemycin $A_4$
13-[3-(3-Methylthioureido)cinnamyloxy]milbemycin $A_4$ 13-(3-Cyanoacetamidocinnamyloxy)milbemycin $A_4$ 13-(3-Methanesulfonylaminocinnamyloxy)milbemycin $A_4$ 13-[3-$\underline{N}$-(Methanesulfonyl)methylaminocinnamyloxy] milbemycin $A_4$ 13-3-(3-Methylaminocinnamyloxy)milbemycin $A_4$ and 13-[3-(3,3-Dimethylcarbazoylamino)cinnamyloxy] milbemycin $A_4$, of which the most preferred compounds are:

13-(3-Cyanoacetamidocinnamyloxy)milbemycin $A_4$ 13-(3-Methanesulfonylaminocinnamyloxy)milbemycin $A_4$ and 13-[3-$\underline{N}$-(Methanesulfonyl)methylaminocinnamyloxy] milbemycin $A_4$.

Also preferred are salts, where available of the above compounds.

The compounds of formula (I) of the present invention may be prepared by a variety of processes known in the art for the preparation of compounds of this type. In general terms a suitable preparative procedure comprises subjecting a compound of formula (II) in either order to steps (a) and (b):

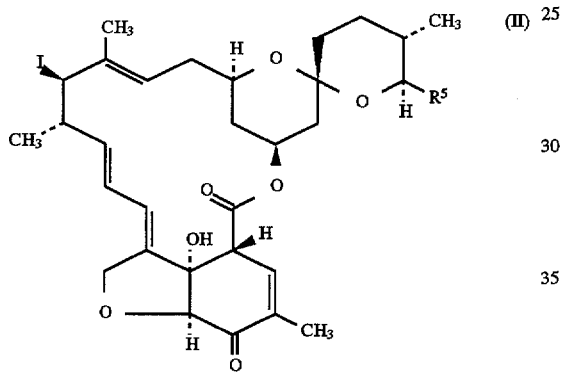

in which $R^5$ is as defined above, (a) reaction with an alcohol of formula (IIa):

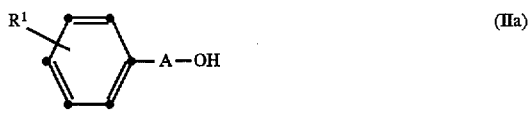

in which $R^1$ is as defined above; and (b) reaction either (b$^i$) with a reducing agent to reduce the oxygen atom at the 5-position to a hydroxy group, followed, if desired by reaction with an acylating agent, to give a compound of formula (I) in which X represents an alkanoyloxy group which has from 1 to 5 carbon atoms, and which is unsubstituted or has at least one substituent selected from the group consisting of substituents (d); or (b$^{ii}$) with hydroxylamine or with a salt thereof, to give a compound of formula (I) in which X represents a hydroxyimino group;

and then, if required, subjecting the product to one or both of steps (c) and (d):

(c) converting a group represented by $R^1$ to any other group so represented; and (d) salifying or esterifying the product.

In the above process, step (a) may be carried out before step (b), or step (b) may be carried out before step (a); we prefer that step (a) should be carried out before step (b).

In more detail, in this preferred embodiment, the compounds of formula (I) of the present invention can be prepared from a 13-iodo-milbemycin of formula (II) as shown in the following Reaction Scheme A:

Reaction Scheme A:

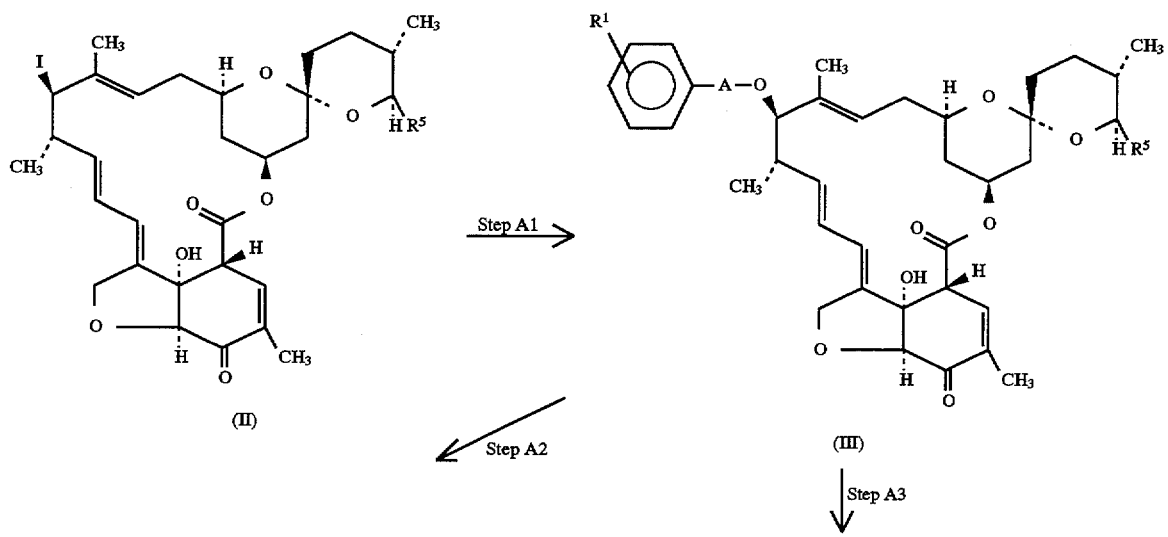

-continued
Reaction Scheme A:

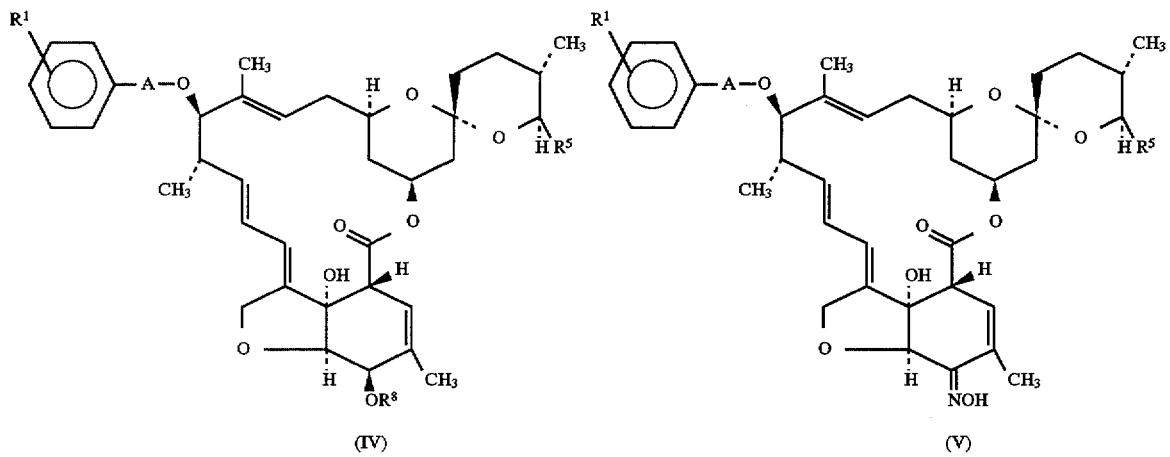

(IV)                                                              (V)

In the above formulae, $R^1$, $R^5$ and A are as defined above and $R^8$ represents a hydrogen atom or a $C_1$–$C_5$ alkanoyl group or substituted $C_1$–$C_5$ alkanoyl group having at least one substituent selected from the group consisting of substituents (d), defined above (i.e. the alkanoyl groups defined above for the alkanoyloxy groups of X).

In Step A1, a compound of formula (III) is prepared by reacting a compound of formula (II) with a cinnamyl alcohol or derivative thereof of formula (IIa) in the presence of a catalyst. Any catalyst capable of catalysing such etherification reactions, as are well known in the art, may equally be employed in this reaction, without any particular restriction. Examples of suitable catalysts include oxides and salts of mercury or silver, preferably a silver compound such as silver oxide, silver perchlorate or silver trifluoromethanesulfonate, or a mercury compound such as mercury oxide, mercury iodide, mercury bromide or mercury trifluoromethanesulfonate.

In certain cases, the reaction may be accelerated by addition of an acid-binding agent. There is no particular limitation on the nature of such an acid-binding agent, provided that it has no adverse effect on the reaction, but 2,6-lutidine and calcium carbonate are preferred examples.

The reaction is normally and preferably effected in the presence of a solvent. There is no particular limitation on the nature of the solvent employed in the reaction, provided that it has no adverse effect on the reaction and that it is capable of solubilizing the starting compound, at least to some extent. Examples of suitable solvents include: aromatic hydrocarbons, such as benzene, toluene or xylene; halogenated hydrocarbons, especially halogenated aliphatic hydrocarbons, such as methylene chloride, 1,2-dichloroethane or chloroform; esters, such as ethyl acetate or propyl acetate; ethers, such as diethyl ether, tetrahydrofuran, dioxane or dimethoxyethane; amides, such as dimethylformamide, dimethylacetamide or hexamethylphosphoric triamide; and sulfoxides, such as dimethyl sulfoxide.

The reaction can take place over a wide range of temperatures, and the precise reaction temperature is not critical to the invention. In general, we find it convenient to carry out the reaction at a temperature from −10° C. to 100° C., preferably from 0° C. to 50° C. The time required for the reaction may also vary widely, depending on many factors, notably the reaction temperature and the nature of the reagents and of the solvent. However, provided that the reaction is effected under the preferred conditions outlined above, a period of from 1 hour to 2 days will usually suffice.

After completion of the reaction, the reaction product may be recovered from the reaction mixture by conventional means. For example, the reaction mixture may be diluted with a water-immiscible organic solvent, after which, if necessary, the insoluble materials are removed by filtration. The filtrate may then be washed, for example successively with an aqueous solution of potassium iodide, an acid and water, and the solvent may be removed by distillation to afford the desired product. The product may, if required, be further purified by such conventional techniques as recrystallization or the various chromatography techniques, notably column chromatography.

In Step A2, a compound of formula (IV) is prepared by reducing the carbonyl group at the 5-position of the compound of formula (III) to a hydroxy group, which, if required, may then be subjected to acylation to give a compound of formula (IV) in which $R^8$ represents an alkanoyl group. There is no particular limitation on the nature of the reducing agent to be used in this reduction, provided than it can reduce the carbonyl group and has no adverse effect on the other functional groups in the compound of formula (III). Such reducing agents include, for example, hydride-producing agents, such as sodium borohydride or diborane, preferably sodium borohydride.

The reaction is normally and preferably effected in the presence of a solvent, and there is equally no particular limitation on the nature of the solvent, provided that it has no adverse effect on the reaction, but a lower alcohol (such as methanol, ethanol or propanol) is preferably used, especially when sodium borohydride is employed as the reducing agent.

The reaction can take place over a wide range of temperatures, and the precise reaction temperature is not critical to the invention. In general, we find it convenient to carry out the reaction at a temperature from 0° C. to 50° C. The time required for the reaction may also vary widely, depending on many factors, notably the reaction temperature and the nature of the reagents. However, provided that the reaction is effected under the preferred conditions outlined above, a period of from 5 minutes to 2 hours will usually suffice.

After completion of the reaction, the reaction product can be recovered easily from the reaction mixture by conventional means. For example, the reaction mixture may be diluted with a water-immiscible organic solvent and washed with water, after which the solvent may be removed by distillation to afford the desired product. The product may, if required, be further purified by such conventional techniques as recrystallization or the various chromatography techniques, notably column chromatography.

The reduction product thus prepared may, if required, be acylated to produce a compound in which $R^8$ is an alkanoyl group. This may take place in an inert solvent, using as the acylating agent an acid corresponding to the alkanoyl group which it is desired to introduce or using a reactive derivative of such an acid. The reaction can be carried out using conventional esterification techniques. Examples of suitable active derivatives of the acid include any of those commonly used for esterification such as acid halides (e.g. an acid chloride or acid bromide), acid anhydrides, mixed acid anhydrides, reactive esters (e.g. the N-hydroxybenztriazole ester) and reactive amides (e.g. the imidazolide).

Where the acid itself is employed, a dehydrating agent (such as dicyclohexylcarbodiimide, p-toluenesulfonic acid or sulfuric acid) is preferably also present. Where a reactive derivative of an acid is employed, an acid-binding agent is preferably also employed. There is no particular limitation on the nature of the acid-binding agent to be used, provided that it has the ability to eliminate an acid, for example, an organic amine such as triethylamine, N,N-diethylaniline, pyridine, 4-dimethylaminopyridine or 1,8-diazabicyclo [5.4.0]undecene-7, may be used.

There is no particular restriction on the nature of the solvent to be employed, provided that it has no adverse effect on the reaction or on the reagents involved and that it is capable of dissolving the reagents, an least to some extent. Examples of suitable solvents include: hydrocarbons, which may be aliphatic, aromatic or cycloaliphatic, such as hexane, benzene, toluene or xylene; halogenated hydrocarbons, especially halogenated aliphatic hydrocarbons, such as methylene chloride, 1,2-dichloroethane or chloroform; esters, such as ethyl acetate or propyl acetate; and ethers, such as diethyl ether, tetrahydrofuran, dioxane or dimethoxyethane.

After completion of the reaction, the reaction product can easily be recovered from the reaction mixture by conventional means. For example, the reaction mixture may be diluted with a water-immiscible organic solvent and washed successively with an acid, an alkali and water, after which the solvent may be removed by distillation to afford the desired product. The product may, if required, be further purified by such conventional techniques as recrystallization or the various chromatography techniques, notably column chromatography.

In Step A3 a compound of formula (V) is prepared by oximation at the 5-position of the compound of formula (III) with hydroxylamine or with a salt thereof (e.g. a salt with a mineral acid such as hydrochloric acid, nitric acid or sulfuric acid).

The reaction is usually carried out in an inert solvent, the nature of which is not critical, provided that it has no adverse effect on the reaction or on the reagents involved and than it is capable of dissolving the reagents, at least to some extent. Examples of suitable solvents include: alcohols, such as methanol or ethanol; ethers, such as tetrahydrofuran or dioxane; aliphatic acids, such as acetic acid; or a mixture of water with any one or more of these solvents.

The reaction can take place over a wide range of temperatures, and the precise reaction temperature is not critical to the invention. In general, we find it convenient to carry out the reaction at a temperature from 10° C. to 80° C. The time required for the reaction may also vary widely, depending on many factors, notably the reaction temperature and the nature of the reagents. However, provided that the reaction is effected under the preferred conditions outlined above, a period of from 1 to 24 hours will usually suffice.

After completion of the reaction, the reaction product can easily be recovered from the reaction mixture by conventional means. For example, the reaction mixture may be diluted with a water-immiscible organic solvent and washed with water, after which the solvent may be removed by distillation to afford the desired product. The product may, if required, be further purified by such conventional techniques as recrystallization or the various chromatography techniques, notably column chromatography.

As an alternative to the above, the reaction of step A2 or A3 may be carried out first, to prepare a compound in which X represents a hydroxy, alkanoyloxy or hydroxyimino group, after which the iodine atom at the 13 position is replaced by the optionally substituted cinnamyloxy group.

The compound of formula (IV) wherein $R^1$ is a substituted amino group can be prepared as illustrated in the following Reaction Scheme B:

Reaction Scheme B:

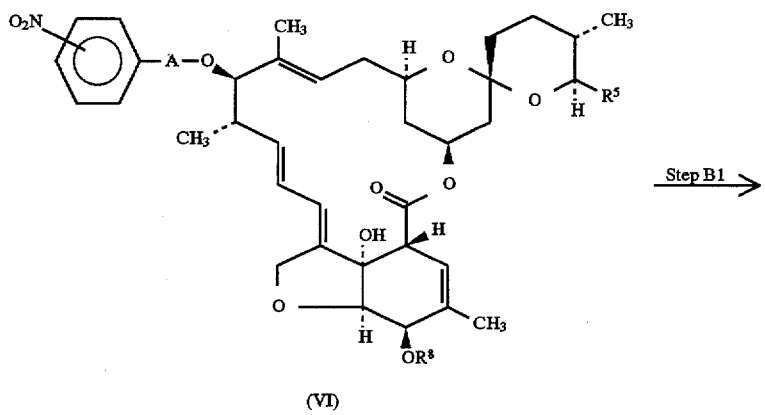

-continued
Reaction Scheme B:

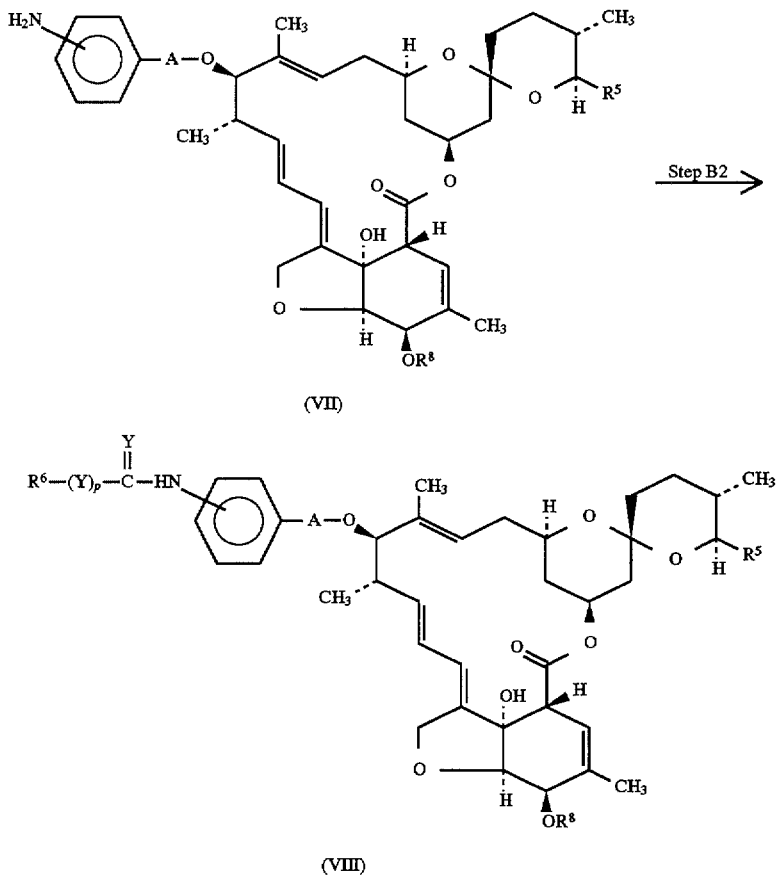

(VII)

(VIII)

In the above formulae, $R^5$, $R^6$ and $R^8$ are as defined above, Y represents an oxygen atom, a sulfur atom or an imino group, and the two symbols Y may be the same or different, and p represents 0 or 1.

In Step B1 a compound of formula (VII) is prepared by reducing the nitro group of a compound of formula (VI) to give an amino group. This may be effected by a conventional reducing method for reducing a nitro group to an amino group. One such method is catalytic reduction using a precious metal catalyst. Examples of catalysts which are preferably employed include palladium-on-carbon, palladium-on-barium sulfate and platinum oxide.

The reaction is normally and preferably effected in the presence of a solvent, and there is no particular restriction on the nature of the solvent to be employed, provided that it has no adverse effect on the reaction or on the reagents involved. Examples of suitable solvents include: alcohols, such as methanol or ethanol; ethers, such as tetrahydrofuran or dioxane; and esters, such as ethyl acetate.

The reaction can take place over a wide range of temperatures, and the precise reaction temperature is not critical to the invention. In general, we find it convenient to carry out the reaction at a temperature from 10° C. to 80° C. The time required for the reaction may also vary widely, depending on many factors, notably the reaction temperature and the nature of the reagents. However, provided that the reaction is effected under the preferred conditions outlined above, a period of from 10 minutes to 5 hours will usually suffice.

An alternative preferred reducing method is reduction with zinc powder in acetic acid. This reaction is preferably carried out at a temperature ranging from 0° C. to room temperature, and the reaction time is usually in the range of from 10 minutes to 2 hours.

After completion of the reaction, the reaction product can easily be recovered from the reaction mixture by conventional means. For example, the reaction mixture may be diluted with a water-immiscible organic solvent, and the insoluble materials, if necessary, removed by filtration. The filtrate may then be washed with water, and the solvent may be removed by distillation to afford the desired product. The product may, if required, be further purified by such conventional techniques as recrystallization or the various chromatography techniques, notably column chromatography.

In Step B2 a compound of formula (VIII) is prepared by reacting the compound of formula (VII) with a reagent that is reactive with the amino group, to introduce the group of formula $R^6-(Y)_p-C(=Y)-NH-$.

The nature of the reagent to be employed will, of course, be dictated by the nature of the group which it is desired to introduce. However, in general, it may be a reactive derivative of a carboxylic acid of the type commonly used as an acylating agent such as an acid halide, an acid anhydride, a mixed acid anhydride, a reactive ester or a reactive amide. Alternatively, it may be: a chloroformate, such as methyl chloroformate or benzyl chloroformate; a thiochloroformate, such as ethyl chlorothioformate; a sulfonyl chloride, such as methanesulfonyl chloride or benzenesulfonyl chloride; an isocyanate; a thioisocyanate; or an imino ether. Alternatively, a carboxylic acid may be used as such, provided that it is activated, for example with dicyclohexylcarbodiimide.

When a halide, such as an acid halide, is employed as the reagent, it is usually preferred to carry out the reaction in the presence of an organic base, such as triethylamine, N,N-diethylaniline, pyridine, 4-dimethylaminopyridine or 1,8-diazabicyclo[5.4.0]undecene, as an acid-binding agent.

The reaction can take place over a wide range of temperatures, and the precise reaction temperature is not critical to the invention. In general, we find it convenient to carry out the reaction at a temperature from 0° C. to 80° C., preferably from 0° C. to room temperature. The time required for the reaction may also vary widely, depending on many factors, notably the reaction temperature and the nature of the reagents. However, provided that the reaction is effected under the preferred conditions outlined above, a period of from 10 minutes to 10 hours will usually suffice.

After completion of the reaction, the reaction product can easily be recovered from the reaction mixture by conventional means. For example, the reaction mixture may be diluted with a water-immiscible organic solvent, and the insoluble materials may then be removed, if required, by filtration and washed with water, after which the solvent may be removed by distillation to afford the desired product. The product may, if required, be further purified by such conventional techniques as recrystallization or the various chromatography techniques, notably column chromatography.

The compound of formula (II), which is used as the starting material in the above sequences of reactions can advantageously be synthesized from 13-hydroxy-5-oxomilbemycin, which is represented by the general formula (IX), as illustrated in the following Reaction Scheme C:

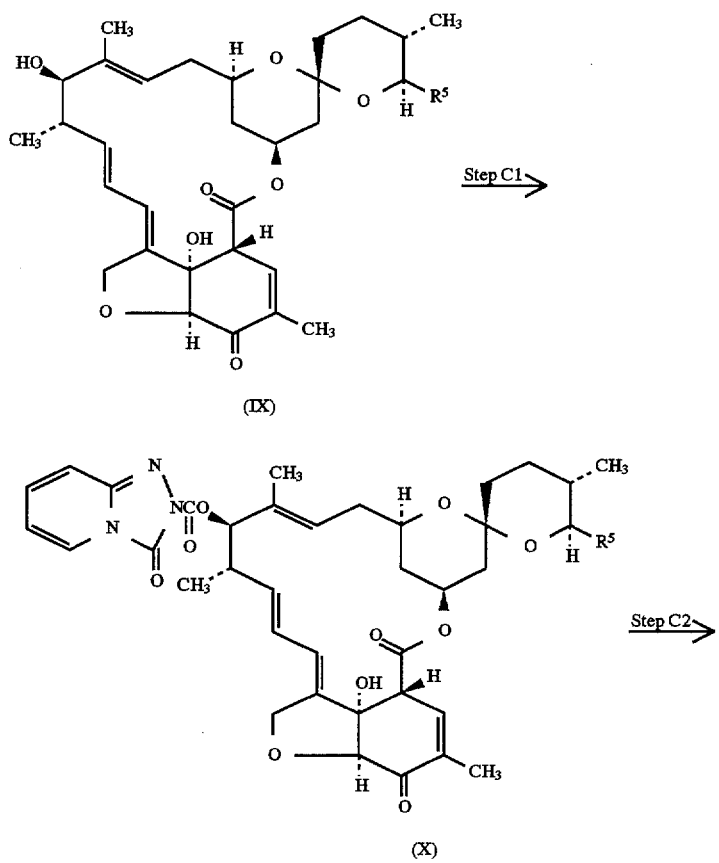

-continued
Reaction Scheme C:

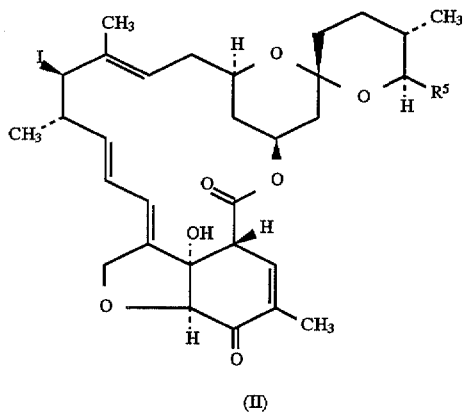

(II)

In the above formulae, $R^5$ is as defined above.

In Step C1 a compound of formula (X) is prepared by reacting the compound of formula (IX) with 2-chloroformyl-1,2,4-triazolo[4.3a]pyridin-3-one in the presence of an acid-binding agent.

There is no particular limitation on the nature of the acid-binding agent to be employed provided that it has the ability to eliminate any acid produced. For example, an organic amine, such as triethylamine, N,N-diethylaniline, pyridine, 4-dimethylaminopyridine or 1,8-diazabicyclo[5.4.0]undecene, may be used.

The reaction is also preferably effected in the presence of an inert solvent, the nature of which is not critical, provided that it has no adverse effect on the reaction or on the reagents involved. Examples of suitable solvents include: hydrocarbons, which may be aliphatic, aromatic or cycloaliphatic, such as hexane, benzene, toluene or xylene; halogenated hydrocarbons, especially halogenated aliphatic hydrocarbons, such as methylene chloride, 1,2-dichloroethane or chloroform; esters, such as ethyl acetate or propyl acetate; and ethers, such as diethyl ether, tetrahydrofuran, dioxane or dimethoxyethane.

The reaction can take place over a wide range of temperatures, and the precise reaction temperature is not critical to the invention. In general, we find it convenient to carry out the reaction at a temperature from 0° C. to 50° C. The time required for the reaction may also vary widely, depending on many factors, notably the reaction temperature and the nature of the reagents. However, provided that the reaction is effected under the preferred conditions outlined above, a period of from 5 minutes to 2 hours will usually suffice.

After completion of the reaction, the reaction product can easily be recovered from the reaction mixture by conventional means. For example, the reaction mixture may be diluted with a water-immiscible organic solvent, the insoluble materials may then be removed, if required, by filtration and washed, for example successively with an aqueous solution of potassium iodide, an acid and water, after which the solvent may be removed by distillation to afford the desired product.

In Step C2 13-iodomilbemycin, which is represented by formula (II), is prepared by reacting the compound of formula (X) with zinc iodide.

This reaction is usually carried out in a solvent. There is no particular restriction on the nature of the solvent to be employed, provided that it has no adverse effect on the reaction or on the reagents involved and that it is capable of dissolving the reagents, at least to some extent. Examples of suitable solvents include: hydrocarbons, which may be aliphatic, aromatic or cycloaliphatic, such as hexane, benzene, toluene or xylene; halogenated hydrocarbons, especially halogenated aliphatic hydrocarbons, such as methylene chloride, 1,2-dichloroethane or chloroform; esters, such as ethyl acetate or propyl acetate; and ethers, such as diethyl ether, tetrahydrofuran, dioxane or dimethoxyethane.

The reaction can take place over a wide range of temperatures, and the precise reaction temperature is non critical to the invention. In general, we find it convenient to carry out the reaction at a temperature from 0° C. to room temperature. The time required for the reaction may also vary widely, depending on many factors, notably the reaction temperature and the nature of the reagents. However, provided that the reaction is effected under the preferred conditions outlined above, a period of from 10 minutes to 2 hours will usually suffice.

After completion of the reaction, the reaction product can easily be recovered from the reaction mixture by conventional means. For example, the insoluble materials may be removed by filtration and the filtrate washed with water, after which the solvent may be removed by distillation to afford the desired product. The product may, if required, be further purified by such conventional techniques as recrystallization or the various chromatography techniques, notably column chromatography.

The compound of formula (IX), which is, therefore, the ultimate starting material for the above sequence of reactions, can be prepared from the natural or semisynthetic milbemycins or avermectins by the method disclosed in Japanese Patent Application Kokai No. Sho 61-103884.

In the compounds of the formula $(I)_w$ of the present invention where $R_w^1$ or $R_w^2$ or substituent $(a)_w$, $(b)_w$, $(c)_w$ or $(d)_w$ represents a halogen atom, this may be a fluorine, chlorine, bromine or iodine atom and is preferably a chlorine or fluorine atom.

Where $R_w^1$, $R_w^2$, $R_w^3$, $R_w^4$, $R_w^6$, $R_w^{6'}$, $R_w^7$, $R_w^9$, $R_w^{10}$ or substituent $(c)_w$ represents an alkyl group, this has from 1 to 4 carbon atoms and may be a straight or branched chain group. Examples of such groups include the methyl, ethyl, propyl, isopropyl, butyl, sec-butyl and t-butyl groups, of which methyl, ethyl, propyl, isopropyl, butyl and sec-butyl groups are preferred and the methyl and ethyl groups are most preferred.

Where $R_w^1$, $R_w^2$, $R_w^6$, $R_w^{6'}$, or $R_w^{10}$ represents a substituted alkyl group, the alkyl part may be any of the alkyl groups exemplified above and: in the case of $R^1$ or $R^2$ the substituent is selected from the group consisting of substituents $(a)_w$; and, in the case of $R_w^6$, $R_w^{6'}$, or $R_w^{10}$, the substituent is selected from the group consisting of substituents $(b)_w$: the substituents being defined above and exemplified elsewhere herein.

Where $R_w^1$, $R_w^2$, $R_w^3$ or $R_w^4$ or substituent $(a)_w$, $(b)_w$, $(c)_w$ or $(d)_w$ represents an alkoxy group, this has from 1 to 4 carbon atoms and may be a straight or branched chain group. Examples of such groups include the methoxy, ethoxy, propoxy, isopropoxy, butoxy, isobutoxy, sec-butoxy and t-butoxy groups, especially the methoxy, ethoxy, propoxy, isopropoxy and butoxy groups.

Where $R_w^1$ or $R_w^2$ represents a $C_2$–$C_6$ alkoxy-alkoxy group, each of the alkoxy parts may gave from 1 to 5, preferably from 1 to 4, carbon atoms, provided that the total number of carbon atoms in the two alkoxy groups does not exceed 6, and preferred examples of such alkoxy groups are as given above. Examples of the alkoxyalkoxy groups include the methoxymethoxy, ethoxymethoxy, propoxymethoxy, butoxymethoxy, 1- and 2-methoxyethoxy, 1- and 2- ethoxymethoxy, 1- and 2- butoxyethoxy and 1-, 2- and 3- methoxypropoxy groups, of which the methoxymethoxy, ethoxymethoxy, propoxymethoxy, butoxymethoxy, methoxymethoxy, ethoxymethoxy and butoxyethoxy groups are preferred.

Where $R_w^6$ represents a $C_2$–$C_8$ alkenyl or alkynyl group, it may be, for example, a vinyl, 1-propenyl, allyl, 1-butenyl, 2-butenyl, 3-butenyl, butadienyl, 1-pentenyl, 2-pentenyl, 3-pentenyl, 4-pentenyl, 1,3-dimethylbutenyl, 1-hexenyl, 2-hexenyl, 3-hexenyl, 4-hexenyl, 5-hexenyl, 1,3-, 1,4-, 1,5-, 2,4-, 2,5- and 3,5- hexadienyl, 1-, 2-, 3-, 4-, 5- and 6-heptenyl, 1-, 2-, 3-, 4-, 5-, 6- and 7-octenyl, ethynyl, 1-propynyl, 1-, 2- and 3-butynyl, 1-, 2-, 3- and 4-pentynyl, 1-, 2-, 3-, 4- and 5-hexynyl, 1-, 2-, 3-, 4-, 5- and 6-heptynyl, 1-, 2-, 3-, 4-, 5-, 6- and 7-octynyl and propargyl groups, of which the 1-propenyl, allyl, 1-butenyl, 2-butenyl, 2-butenyl, 1,3-dimethylbutenyl, hexadienyl and propargyl groups are preferred. Such groups may be unsubstituted or they may be substituted by at least one of substituents $(b)_w$, defined above and exemplified generally herein. However, they are preferably unsubstituted.

Where $R_w^6$, $R_w^7$ or substituent $(b)_w$ represents a cycloalkyl group, this may contain from 3 to 8 ring atoms, and examples are the cyclopropyl, cyclobutyl, cyclopentyl, cyclohexyl cycloheptyl and cyclooctyl groups, of which the cyclopentyl and cyclohexyl groups are more preferred. Such groups may be unsubstituted or they may be substituted by at least one of substituents $(c)_w$, defined above and exemplified generally herein. However, they are preferably unsubstituted.

Where $R_w^6$ represents a heterocyclic group, this may be a saturated or unsaturated group containing from 3 to 6 ring atoms, of which at least one, and preferably from 1 to 3, is a nitrogen, oxygen or sulfur atom. More preferably the group has from 0 to 3 such nitrogen atoms, 0, 1 or 2 such oxygen atoms and 0, 1 or 2 such sulfur atoms, provided that the total number of hetero-atoms is not less than 1 and does not exceed 3. Where the group is unsaturated, it may be non-aromatic or aromatic in character. The group may be monocyclic or it may be fused to one or two benzene rings to produce a bicyclic or tricyclic group, in which the heterocyclic part may be aromatic or non-aromatic character. Examples of such groups include the oxiranyl, oxetanyl, aziridinyl, azetidinyl, thiranyl, thietanyl, furyl, thienyl, pyrrolyl, pyridyl, thiazolyl, isothiazolyl, xazolyl, isoxazolyl, imidazolyl, pyrazolyl, pyranyl, pyrazinyl, pyridazinyl, pyrimidinyl, benzofuranyl, isobenzofuranyl, benzothienyl, isobenzothienyl, indolyl, quinolyl, isoquinolyl, quinazolinyl, quinoxalinyl, napnthyridynyl, xantphenyl, tetrahydrofuranyl, tetrahydrothienyl, pyrrolidinyl, thiazolidinyl, imidazolidinyl, imidazolinyl, oxazolinyl, oxazolidinyl, pyrazolidinyl, piperazyl, tetrahydropyrimidinyl, dihydropyridazinyl, morpholinyl, thiomorpholinyl, indolinyl, tetrahydroquinolyl, pyrrolidonyl, piperidonyl, pyridonyl, thianthrenyl, chromenyl, phenoxathiinyl, 2H-pyrrolyl, isoindolyl, 3 H-indolyl, indazolyl, phthalazinyl, quinoxalinyl, quinazolinyl, cinnolinyl, carbazolyl, phenanthridinyl, acridinyl, perimidinyl, phenazinylphenothiazinyl, furazanyl, phenoxazinyl, isochromanyl, chromanyl, pyrazolinyl, indolinyl and isoindolinyl groups. Such groups may be unsubstituted or they may have at least one substituent selected from the group consisting of substituents $(c)_w$, defined above and exemplified elsewhere herein.

Where $R_w^1$ or $R_w^2$ represents a group of formula $-(CH_2)_{n_w}NR_w^9C(=Y_w)NR_w^{6'}R_w^{6'}$, the two groups represented by $R_w^{6'}$ may be the same or different and may be selected from those groups represented by $R_w^6$, and defined and exemplified above. Alternatively, the two groups $R_w^{6'}$, together with the nitrogen atom to which they are attached, may form a nitrogen-containing heterocyclic group, which may optionally have an additional nitrogen, oxygen or sulfur heteroatom: such a group may contain from 3 to 7 atoms in total (i.e. including the afore-mentioned nitrogen atom) and may be saturated or unsaturated. If it is unsaturated the unsaturation may be aromatic or non-aromatic in character, provided that the group has a nitrogen atom which can provide the nitrogen atom of the group $-NR_w^{6'}R_w^{6'}$. Examples of such groups include the aziridinyl, azetidinyl, pyrrolyl, imidazolyl, pyrazolyl, pyrrolidinyl, thiazolidinyl, imidazolidinyl, imidazolinyl, oxazolinyl, oxazolidinyl, pyrazolidinyl, piperazyl, tetrahydropyrimidinyl, dihydropyridazinyl, pyrrolidonyl, piperidonyl, pyridonyl, pyrazolinyl, azepinyl, perhydroazepinyl, oxazepinyl and thiazepinyl groups. Such groups may be unsubstituted or they may have at least one substituent selected from the group consisting of substituents $(c)$, defined above and exemplified elsewhere herein.

Where $R_w^1$ or $R_w^2$ represents a group of formula $-(CH_2)_{n_w}NR_w^9C(=Y_w)NR_w^{6''}R_w^{6''}$, the group $-NR_w^{6''}R_w^{6''}$ may be a group of formula $-NR_w^6R_w^6$, in which each $R_w^6$ is as defined above, or it may be a group of formula $-NR_w^{6'}R_w^{6'}$, which forms a heterocyclic group as exemplified in the preceding paragraph. Alternatively, two of the symbols $R_w^{6''}$ attached to different nitrogen atoms may form a heterocyclic ring containing at least two nitrogen atoms and optionally another hetero-atom selected from the group consisting of nitrogen, oxygen and sulfur hetero-atoms. Examples of such groups include the divalent groups derived by removal of a hydrogen atom from each of the two adjacent nitrogen atoms of the ring systems: diaziridine, diazete, diazetidine, pyrazolidine, pyrazoline, 1,2-dihydropyridazine, 1,2,3,4-tetrahydropyridazine, 1,2,5,6-tetrahydropyridazine, perhydropyridazine, 1,2-dihydro-1,2-diazepine and perhydro-1,2-diazepine.

Where $X_w$ or substituent $(a)_w$ or $(c)_w$ represents an alkanoyloxy group, it contains from 1 to 5 carbon atoms and may be a straight or branched chain group. Examples of such groups include the formyloxy, acetoxy, propionyloxy, butyryloxy, isobutyryloxy, valeryloxy, isovaleryloxy and pivaloyloxy groups. Such groups may be unsubstituted, or they may have at least one substituent selected from the group consisting of substituents $(d)_w$, defined above and exemplified elsewhere herein.

Where substituent $(a)_w$, $(b)_w$ or $(c)_w$ is an alkylthio group, this contains from 1 to 4 carbon atoms and may be a straight or branched chain group. Examples of such groups include the methylthio, ethylthio, propylthio, isopropylthio, butylthio, isobutylthio, sec-butylthio and t-butylthio groups.

Where substituent $(b)_w$, $(c)_w$ or $(d)_w$ is an alkoxycarbonyl group, this has a total of from 2 to 5 carbon atoms, i.e. the alkoxy part has from 1 to 4 carbon atoms, and this alkoxy part may be any of those alkoxy groups exemplified above. Examples of such alkoxycarbonyl groups include the methoxycarbonyl, ethoxycarbonyl, propoxycarbonyl, butoxycarbonyl, sec-butoxycarbonyl and t-butoxycarbonyl groups.

Where substituent $(b)_w$ is a cyanoalkylthio group, this may be a straight or branched chain group having from 2 to 5 carbon atoms in total, i.e. the alkyl part has from 1 to 4 carbon atoms and may be any of those alkyl groups exemplified above. Examples of such cyanoalkylthio groups include the cyanomethylthio, 1-cyanoethylthio, 2-cyanoethylthio, 1-cyanopropylthio, 2-cyanopropylthio, 3-cyanopropylthio, 1-cyanobutylthio, 2-cyanobutylthio, 3-cyanobutylthio, 4-cyanobutylthio, 3-cyano-2-methylpropylthio, 2-cyano-2-methylpropylthio and 2-cyano-1-methylethylthio groups.

Where substituent $(b)_w$ is an aryl group, this has from 6 to 14 ring carbon atoms and is a carbocyclic group. Examples of such groups include the phenyl, naphthyl (1- or 2-) and anthryl groups, of which the phenyl and naphthyl groups are preferred and the phenyl group is most preferred.

Where substituent $(b)_w$ is an aromatic heterocyclic group, this has from 5 to 8 ring atoms of which from 1 to 4 are hetero-atoms selected from the group consisting of nitrogen, oxygen and sulfur hetero-atoms and which has at least two conjugated double bonds to give an aromatic character to the ring. More preferably the group has from 0 to 4 such nitrogen atoms, 0, 1 or 2 such oxygen atoms and 0, 1 or 2 such sulfur atoms, provided that the total number of hetero-atoms is not less than 1 and does not exceed 4. The group may be monocyclic or it may be fused to a benzene ring so form a bicyclic ring system. Such groups may be substituted or unsubstituted and, if substituted, have at least one substituent selected from the group consisting of substituents $(c)_w$, defined above and exemplified elsewhere herein. Examples of such aromatic heterocyclic groups include the pyridyl, thienyl, furyl, pyrrolyl, imidazolyl, triazolyl, tetrazolyl, thiazolyl, oxazolyl, indolyl benzofuryl, isobenzofuryl, chromenyl. 2H-pyrrolyl, pyrazolyl, isothiazolyl, isoxazolyl, pyrazinyl, pyrimidinyl, pyridazinyl, isoindolyl, 3H-indolyl, 1H-indazolyl, isoquinolyl, quinolyl, phthalazinyl, quinoxalinyl, quinazolinyl and cinnolinyl groups.

Where substituent $(b)_w$ is an aryloxy or arylthio group, the aryl part has from 6 to 10 carbon atoms and is a carbocyclic aryl group. Examples include the phenoxy, phenylthio, 1-naphthyloxy, 2-naphthyloxy, 1-naphthylthio and 2-naphthylthio groups, of which the phenoxy and phenylthio groups are preferred. Such groups may be substituted or unsubstituted and, if substituted, the substituent is selected from the group consisting of substituents $(c)_w$, defined above and exemplified elsewhere herein.

Where substituent $(c)_w$ is a mono- or di- alkylamino group, the or each alkyl group may have from 1 to 4 carbon atoms and may be a straight or branched chain group. Examples of alkyl groups are given above. Examples of such mono- and di-alkylamino groups include the methylamino, ethylamino, propylamino, isopropylamino, butylamino, dimethylamino, diethylamino, N-methyl-N-ethylamino, N-methyl-N-propylamino and N-ethyl-N-butylamino groups.

Where substituent $(c)_w$ is a mono- or di-alkylcarbamoyl group, the or each alkyl group may have from 1 to 4 carbon atoms and may be a straight or branched chain group. Examples of alkyl groups are given above. Examples of such mono- and di- alkylcarbamoyl groups include the methylcarbamoyl, ethylcarbamoyl, propylcarbamoyl, isopropylcarbamoyl, butylcarbamoyl, dimethylcarbamoyl, diethylcarbamoyl, N-methyl-N-ethylcarbamoyl, N-methyl-N-propylcarbamoyl and N-ethyl-N-butylcarbamoyl groups.

Where substituent $(c)_w$ is a $C_1$–$C_5$ alkanoylamino group, the alkanoyl part may be a straight or branched chain group and examples include the formylamino, acetylamino, propionylamino, butyrylamino, isobutyrylamino, valerylamino, isovalerylamino and pivaloylamino groups.

Where $R^7$ represents an aralkyl group, the alkyl part has from 1 to 4 carbon atoms and may be any of the alkyl groups exemplified above. The aryl part has from 6 to 10 carbon atoms in its ring and again, may be any of the aryl groups exemplified above. Examples of such aralkyl groups include the benzyl, phenethyl, α-methylbenzyl, 1-phenylpropyl, 2-phenylpropyl, 3-phenylpropyl and 4-phenylbutyl groups, of which the benzyl and phenethyl groups are preferred.

Where substituent $(d)_w$ is a carboxy group, the compounds can form salts with various sorts of bases. Such salts includes, for example: salts with an alkali metal, such as lithium, sodium or potassium: salts with an alkaline earth metal, such as calcium or barium; salts with another metal, such as magnesium or aluminum; and salts with an organic amine, such as triethylamine or triethanolamine.

Of the compounds of formula (I) of the present invention, representative preferred classes are as follows:

(1) those wherein:

$R_w^1$ represents a hydrogen atom; and $R_w^2$ represents a hydrogen atom, a $C_1$–$C_3$ alkyl group (such as a methyl, ethyl, propyl or isopropyl group), a $C_1$–$C_3$ alkoxy group (such as a methoxy, ethoxy, propoxy or isopropoxy group), a fluorine or chlorine atom, a nitro group or an amino group;

(2) those wherein:

$R_w^1$ represents a hydrogen atom; and $R_w^2$ represents a group of formula $-(CH_2)_{n_w}NR_w^{9a}COR_w^{6a}$ [in which $n_w$ is 0, $R_w^{9a}$ represents a hydrogen atom or a methyl group, and $R_w^{6a}$ represents a $C_1$–$C_4$ alkyl group (such as a methyl, ethyl, propyl, isopropyl or butyl group), a $C_3$–$C_5$ cycloalkyl group (such as a cyclopropyl, cyclobutyl or cyclopentyl group), a $C_1$–$C_3$ alkyl group substituted with a halogen, cyano, $C_1$–$C_3$ alkoxy, $C_1$–$C_3$ alkylthio, cyanomethylthio or phenoxy substituent (such as a fluoromethyl, bromoethyl, difluoromethyl, cyanomethyl, cyanopropyl, methoxymethyl, ethoxymethyl, methylthiomethyl, cyanomethylthiomethyl or phenoxymethyl group); an alkenyl group (such as a vinyl or allyl group), an unsubstituted phenyl group, a phenyl group substituted wish a $C_1$–$C_3$ alkyl, $C_1$–$C_3$ alkoxy, halogen or nitro substituent (such as a tolyl, methoxyphenyl, fluorophenyl or nitrophenyl group), a pyridyl group, a pyrimidyl group, a pyrazyl group, a furyl group or a thienyl group], (3) those wherein:

$R_w^1$ represents a hydrogen atom; and $R_w^2$ represents a group of formula —$(CH_2)_{n_w}NR_w^{9a}COCOR_w^{6b}$ [in which $n_w$ is 0, $R_w^{9a}$ represents a hydrogen atom or a methyl group, and $R_w^{6b}$ represents a hydrogen atom, a $C_1$–$C_4$ alkyl group (such as a methyl, ethyl, propyl, isopropyl or butyl group), a $C_3$–$C_5$ cycloalkyl group (such as a cyclopropyl, cyclobutyl or cyclopentyl group), an alkenyl group (such as a vinyl or allyl group), an unsubstituted phenyl group, a phenyl group substituted with a $C_1$–$C_3$ alkyl, $C_1$–$C_3$ alkoxy, halogen or nitro substituent (such as a tolyl, methoxyphenyl, fluorophenyl or nitrophenyl group)];

(4) those wherein:
$R_w^1$ represents a hydrogen atom; and
$R_w^2$ represents a group of formula —$(CH_2)_{n_w}NR_w^{9a}C(=Y_w)YR_w^{6c}$ [in which $n_w$ is 0, $R_w^{9a}$ represents a hydrogen atom or a methyl group, both $Y_w$ are oxygen atoms and $R_w^{6c}$ represents a $C_1$–$C_4$ alkyl group (such as a methyl, ethyl, propyl, isopropyl or butyl group), a $C_1$–$C_4$ alkyl group substituted with a halogen or $C_1$–$C_3$ alkoxy substituent (such as a fluoroethyl, trichloroethyl, methoxyethyl or ethoxyethyl group), an alkenyl group (such as a vinyl or allyl group), a benzyl group, a methoxybenzyl group, a nitrobenzyl group, a furfuryl group, a thenyl group or a phenyl group], (5) those wherein:
$R_w^1$ represents a hydrogen atom; and
$R_w^2$ represents a group of formula —$(CH_2)_{n_w}NR_w^{9a}C(=Y_w)NR_w^{6d}R_w^{6e}$

[in which $n_w$ is 0, $R_w^{9a}$ represents a hydrogen atom or a methyl group, $Y_w$ represents an oxygen atom or a sulfur atom, and $R_w^{6d}$ and $R_w^{6e}$ are the same or different and each represents a $C_1$–$C_4$ alkyl group (such as a methyl, ethyl, propyl, isopropyl or butyl group), a $C_3$–$C_6$ cycloalkyl group (such as a cyclopropyl, cyclobutyl, cyclopentyl or cyclohexyl group), an unsubstituted phenyl group, a phenyl group substituted with a $C_1$–$C_3$ alkyl, $C_1$–$C_3$ alkoxy, halogen or nitro substituent (such as a tolyl, methoxyphenyl, fluorophenyl or nitrophenyl group), or $R_w^{6d}$ and $R_w^{6e}$, together with the nitrogen atom to which they are attached, represent a piperidino, piperazino, morpholino, pyrrolidino or aziridino group];

(5) those wherein:
$R_w^1$ represents a hydrogen atom; and
$R_w^2$ represents a group of formula —$(CH_2)_{n_w}NR_w^{9a}C(=Y_w)NR_w^{6f}NR_w^{6g}R_w^{6h}$

[in which $n_w$ is 0, $R_w^{9a}$ represents a hydrogen atom or a methyl group, $Y_w$ represents an oxygen atom or a sulfur atom, and $R_w^{6f}$, $R_w^{6g}$ and $R_w^{6h}$ are the same or different and each represents a hydrogen atom, a $C_1$–$C_4$ alkyl group (such as a methyl, ethyl, propyl, isopropyl or butyl group), a $C_3$–$C_6$ cycloalkyl group (such as a cyclopropyl, cyclobutyl, cyclopentyl or cyclohexyl group), an unsubstituted phenyl group; a phenyl group substituted with a $C_1$–$C_3$ alkyl, $C_1$–$C_3$ alkoxy, halogen or nitro substituent (such as a tolyl, methoxyphenyl, fluorophenyl or nitrophenyl group), or $R_w^{6g}$ and $R_w^{6h}$, together with the nitrogen atom to which they are attached, represent a piperidino, piperazino, morpholino, pyrrolidino or aziridino group, or $R_w^{6f}$ and $R_w^{6g}$, together with the nitrogen atoms to which they are attached, represent a pyrazolidinyl or tetrahydropyridazinyl group];

(7) those wherein:
$R_w^1$ represents a hydrogen atom; and
$R_w^2$ represents a group of formula —$(CH_2)_{n_w}NR_w^{9a}C(=Y_w)NR_w^{6j}NHZ_w$ {in which $n_w$ is 0, $R_w^{9a}$ represents a hydrogen atom or a methyl group, Y represents an oxygen atom or a sulfur atom, $R_w^{6j}$ represents a hydrogen atom, a $C_1$–$C_4$ alkyl group (such as a methyl, ethyl, propyl, isopropyl or butyl group) or a $C_3$–$C_a$ cycloalkyl group (such as a cyclopropyl, cyclobutyl, cyclopentyl or cyclohexyl group): $Z_w$ represents a group of formula —$COOR_w^{7a}$

[wherein $R_w^{7a}$ represents a $C_1$–$C_4$ alkyl group (such as a methyl, ethyl, propyl, isopropyl or butyl group), a $C_3$–$C_6$ cycloalkyl group (such as a cyclopropyl, cyclobutyl, cyclopentyl or cyclohexyl group) or a benzyl group].

a group of formula —$COR_w^{6k}$

[wherein $R_w^{6k}$ represents a $C_1$–$C_4$ alkyl group (such as a methyl, ethyl, propyl, isopropyl or butyl group), a $C_3$–$C_6$ cycloalkyl group (such as a cyclopropyl, cyclobutyl, cyclopentyl or cyclohexyl group), an unsubstituted phenyl group, a phenyl group substituted with a $C_1$–$C_3$ alkyl, $C_1$–$C_3$ alkoxy, halogen or nitro substituent (such as a tolyl, methoxyphenyl, fluorophenyl or nitrophenyl group)] or a group of formula —$SO_2R_w^{6m}$

[wherein $R_w^{6m}$ represents a $C_1$–$C_4$ alkyl group (such as a methyl, ethyl, propyl, isopropyl or butyl group), an unsubstituted phenyl group or a phenyl group substituted with a $C_1$–$C_3$ alkyl, $C_1$–$C_3$ alkoxy, halogen or nitro substituent (such as a tolyl, methoxyphenyl, fluorophenyl or nitrophenyl group)]};

(8) those wherein:
$R_w^1$ represents a hydrogen atom; and
$R_w^2$ represents a group of formula —$(CH_2)_{n_w}NR_w^{9a}C(=NR_w^{10a})NHR_w^{10b}$ {in which $n_w$ is 0, $R_w^{9a}$ represents a hydrogen atom or a methyl group, and $R_w^{10a}$ and $R_w^{10b}$ are the same or different and each represents a hydrogen atom, a $C_1$–$C_4$ alkyl group (such as a methyl, ethyl, propyl, isopropyl or butyl group), an unsubstituted phenyl group, a phenyl group substituted with a $C_1$–$C_3$ alkyl, $C_1$–$C_3$ alkoxy, halogen or nitro substituent (such as a tolyl, methoxyphenyl, fluorophenyl or nitrophenyl group), a group of formula —$COOR_w^{7b}$

[wherein $R_w^{7b}$ represents a $C_1$–$C_4$ alkyl group (such as a methyl, ethyl, propyl, isopropyl or butyl group), a $C_3$–$C_6$ cycloalkyl group (such as a cyclopropyl, cyclobutyl, cyclopentyl or cyclohexyl group) or a benzyl group] or a group of formula —$COR_w^{6n}$

[wherein $R_w^{6n}$ represents a $C_1$–$C_4$ alkyl group (such as a methyl, ethyl, propyl, isopropyl or butyl group), a $C_3$–$C_6$ cycloalkyl group (such as a cyclopropyl, cyclobutyl, cyclopentyl or cyclohexyl group), an unsubstituted phenyl group or a phenyl group substituted with a $C_1$–$C_3$ alkyl, $C_1$–$C_3$ alkoxy, halogen or nitro substituent (such as a tolyl, methoxyphenyl, fluorophenyl or nitrophenyl group)]};

(9) those wherein:
$R_w^1$ represents a hydrogen atom; and
$R_w^2$ represents a group of formula —$(CH_2)_{n_w}NR_w^{9a}C(NR_w^{10c})R_w^{6p}$ {in which $n_w$ is 0; $R_w^{9a}$ represents a hydrogen atom or a methyl group; $R_w^{10c}$ represents a hydrogen atom, a $C_1$–$C_4$ alkyl group (such as a methyl, ethyl, propyl, isopropyl or butyl group), an unsubstituted phenyl group, a phenyl group substituted with a $C_1$–$C_3$ alkyl, $C_1$–$C_3$ alkoxy, halogen or nitro substituent (such as a tolyl, methoxyphenyl, fluorophenyl or nitrophenyl group),
a proud of formula —$COOR_w^{7c}$
[wherein $R_w^{7c}$ represents a $C_1$–$C_4$ alkyl group (such as a methyl, ethyl, propyl, isopropyl or butyl group), a $C_3$–$C_6$ cycloalkyl group (such as a cyclopropyl, cyclobutyl, cyclopentyl or cyclohexyl group) or a benzyl group]:
or a group of formula —$COR_w^{6q}$
[wherein $R_w^{6q}$ represents a $C_1$–$C_4$ alkyl group (such as a methyl, ethyl, propyl, isopropyl or butyl group), a $C_3$–$C_6$ cycloalkyl group (such as a cyclopropyl, cyclobutyl, cyclopentyl or cyclohexyl group), an unsubstituted phenyl group: or a phenyl group substituted with a $C_1$–$C_3$ alkyl, $C_1$–$C_3$ alkoxy, halogen or nitro substituent (such as a tolyl, methoxyphenyl, fluorophenyl or nitrophenyl group)] and
$R_w^{6p}$ represents a $C_1$–$C_4$ alkyl group (such as a methyl, ethyl, propyl, isopropyl or butyl group), a $C_3$–$C_6$ cycloalkyl group (such as a cyclopropyl, cyclobutyl, cyclopentyl or cyclohexyl group), an unsubstituted phenyl group or a phenyl group substituted with a $C_1$–$C_3$ alkyl, $C_1$–$C_3$ alkoxy, halogen or nitro substituent (such as a tolyl, methoxyphenyl, fluorophenyl or nitrophenyl group)]};

(10) those wherein:
$R_w^1$ represents a hydrogen atom; and
$R_w^2$ represents a group of formula —$(CH_2)_{n_w}NR_w^{9a}SO_{m_w}R_w^{6r}$
[in which $n_w$ is 0, $R_w^{9a}$ represents a hydrogen atom or a methyl group, $m_w$ is 1 or 2 and $R_w^{6r}$ represents a $C_1$–$C_4$ alkyl group (such as a methyl, ethyl, propyl, isopropyl or butyl group), a $C_2$–$C_4$ cyanoalkyl group (such as a cyanomethyl or cyanobutyl group), an unsubstituted phenyl group, a phenyl group substituted with a $C_1$–$C_3$ alkyl, $C_1$–$C_3$ alkoxy, halogen or nitro substituent (such as a tolyl, methoxyphenyl, fluorophenyl or nitrophenyl group)];

(11) those wherein:
$R_w^1$ represents a hydrogen atom, and
$R_w^2$ represents a group of formula —$CONHR_w^{6s}$
[in which $R_w^{6s}$ represents a $C_1$–$C_4$ alkyl group (such as a methyl, ethyl, propyl, isopropyl or butyl group), a $C_3$–$C_6$ cycloalkyl group (such as a cyclopropyl, cyclobutyl, cyclopentyl or cyclohexyl group), an unsubstituted phenyl group, a phenyl group substituted with a $C_1$–$C_3$ alkyl, $C_1$–$C_3$ alkoxy, halogen or nitro substituent (such as tolyl, methoxyphenyl, fluorophenyl or nitrophenyl group)];

(12) those wherein $R_w^2$ as defined in (2) to (11) above is attached at the p-position of the benzene ring.

(13) those wherein:
$R_w^1$ represents a hydrogen atom, and
$R_w^2$ represents a group of formula —$COOR_w^{7d}$ (in which $R_w^{7d}$ represents a methyl, ethyl or benzyl group);

(14) those wherein:
$R_w^1$ represents a methoxy group, and
$R_w^2$ represents a $C_1$–$C_3$ alkoxy group (such as methoxy, ethoxy or propoxy group) or a $C_2$–$C_4$ alkoxyalkoxy group (such as a methoxymethoxy, ethoxymethoxy or propoxymethoxy group);

(15) those wherein $R_w^5$ represents an ethyl group;

(16) those wherein $R_w^5$ represents a mixture of an ethyl group and methyl group;

(17) those wherein $R_w^3$ and $R_w^4$ are hydrogen atoms; and

(18) those wherein $X_w$ represents a hydroxy group.

Many of the compounds of the present invention will contain one or more basic nitrogen atoms and will, therefore, be capable of forming acid addition salts. There is no particular restriction on the nature of the acid employed to form the salt, provided only that, where the compound is intended to be used in human or animal therapy, the salt should be pharmaceutically acceptable, which, as is well known in the art, means that it should not have increased (or unacceptably increased) toxicity or reduced (or unacceptably reduced) activity compared with the parent compound. Where the compound is to be used for other purposes, e.g. as an intermediate in the preparation of other compounds or as an insecticidal, acaricidal or anthelmintic agent for application to non-living or non-animal matter, even this restriction does not apply. Examples of suitable acids include: inorganic acids, such as hydrochloric acid, hydrobromic acid, hydroiodic acid, phosphoric acid, sulfuric acid or nitric acid; organic sulfonic acids, such as methanesulfonic acid, ethanesulfonic acid, benzenesulfonic acid or p-toluenesulfonic acid; and organic carboxylic acids, such as oxalic acid, tartaric acid, citric acid, maleic acid, malonic acid, succinic acid, acetic acid, benzoic acid, mandelic acid, ascorbic acid, lactic acid, gluconic acid and malic acid.

Representative examples of the compounds of the formula $(I)_w$ of the present invention are as follows:

13-Phenethyloxymilbemycin $A_4$,

13-Phenethyloxymilbemycin $A_3$,

13-Phenethyloxymilbemycin D,

13-Deoxy-13-phenethyloxy-22,23-dihydroavermectin $B_{1a}$-aglycone, 13-(2-Phenylpropoxy)milbemycin $A_4$, 13-(1-Phenyl-1-methylethoxy)milbemycin $A_4$, 13-(2-Methoxy-2-phenylethoxy)milbemycin $A_4$, 13-[2-(4-Methylphenyl)ethoxy]milbemycin $A_4$, 13-[2-(4-Chlorophenyl)ethoxy]milbemycin $A_4$, 13-[2-(4-Fluorophenyl)ethoxy]milbemycin $A_4$, 13-[2-(4-Methoxyphenyl)ethoxy]milbemycin $A_4$, 13-[2-(4-Cyanophenyl)ethoxy]milbemycin $A_4$, 13-[2-(4-Carbamoylphenyl)ethoxy]milbemycin $A_4$, 13-[2-(4-Methoxycarbonylphenyl)ethoxy]milbemycin $A_4$, 13-[2-(2,5-Dimethylphenyl)ethoxy]milbemycin $A_4$, 13-[2-(2,6-Difluorophenyl)ethoxy]milbemycin $A_4$, 13-[2-(3,4-Dichlorophenyl)ethoxy]milbemycin $A_4$, 13-[2-(2,5-Dimethoxyphenyl)ethoxy]milbemycin $A_4$, 13-[2-(3,4-Dimethoxyphenyl)ethoxy]milbemycin $A_4$,
13-[2-(3,4-Dimethoxyphenyl)propoxy]milbemycin $A_4$,
13-[2-(3,4-Dimethoxyphenyl)ethoxy]milbemycin D,
13-Deoxy-13-[2-(3,4-dimethoxyphenyl)ethoxy]-22,23-di-hydroavermectin $B_{1a}$-aglycone,
13-[2-(4-Ethoxy-3-methoxyphenyl)ethoxy]milbemycin $A_4$,
13-[2-(4-Methoxy-3-nitrophenyl)ethoxy]milbemycin $A_4$,
13-[2-(3-Methoxy-4-nitrophenyl)ethoxy]milbemycin $A_4$,
13-[2-(4-Nitrophenyl)ethoxy]milbemycin $A_4$
13-[2-(4-Aminophenyl)ethoxy]milbemycin $A_4$,
13-[2-(4-Amino-3-methoxyphenyl)ethoxy]milbemycin $A_4$,
13-[2-(3-Amino-4-methoxyphenyl)ethoxy]milbemycin $A_4$,
13-[2-(4-Formylaminophenyl)ethoxy]milbemycin $A_4$,
13-[2-(4-Acetamidophenyl)ethoxy]milbemycin $A_4$,
13-[2-(4-Acetamidophenyl)ethoxy]milbemycin $A_4$ 5-oxime,
13-[2-(4-Acetamidophenyl)ethoxy]milbemycin D,
13-[2-(4-Chloroacetamidophenyl)ethoxy]milbemycin $A_4$
13-[2-(4-Phenylacetamidophenyl)ethoxy]milbemycin $A_4$,
13-[2-(4-Phenoxyacetamidophenyl)ethoxy]milbemycin $A_4$,
13-[2-(4-Propionamidophenyl)ethoxy]milbemycin $A_4$,
13-[2-(4-Butyramidophenyl)ethoxy]milbemycin $A_4$,
13-[2-(4-Acryloylaminophenyl)ethoxy]milbemycin $A_4$,
13-[2-(4-Cyanoacetamidophenyl)ethoxy]milbemycin $A_4$,
13-[2-(4-Trifluoroacetamidophenyl)ethoxy]milbemycin $A_4$,
13-[2-(4-Cyclohexanecarbonylaminophenyl)ethoxy]milbemycin $A_4$,
13-[2-(4-Benzamidophenyl)ethoxy]milbemycin $A_4$,
13-[2-(4-Benzamidophenyl)ethoxy]milbemycin D,
13-Deoxy-13-[2-(4-benzamidophenyl)ethoxy]-22,23dihydroavermectin $B_{1a}$-aglycone,
13-[2-(4-Benzamido-3-methoxyphenyl)ethoxy]milbemycin $A_4$,
13-{2-[4-(p-Toluoylamino)phenyl]ethoxy milbemycin $A_4$,
13-{2-[4-(p-Anisoylamino)phenyl]ethoxy milbemycin $A_4$,
13-{2-[4-(4-Fluorobenzamido)phenyl]ethoxy milbemycin $A_4$,
13-{2-[4-(4-Chlorobenzamido)phenyl]ethoxy milbemycin $A_4$,
13-{2-[4-(4-Aminobenzamido)phenyl]ethoxy milbemycin A4,
13-{2-[4-(4-Acetamidobenzamido)phenyl]ethoxy milbemycin $A_4$,
13-{2-[4-(4-Cyanobenzamido)phenyl]ethoxy milbemycin $A_4$,
13-{2-[4-(2-Methoxycarbonylbenzamido)phenyl]ethoxymilbemycin $A_4$,
13-{2-[4-(2-Furoylamino)phenyl]ethoxy milbemycin $A_4$,
13-{2-[4-(2-Thenoylamino)phenyl]ethoxy milbemycin $A_4$,
13-{2-[4-(2-Pyridylcarbonylamino)phenyl]ethoxy milbemycin $A_4$,
13-{2-[4-(Nicotinoylamino)phenyl]ethoxy milbemycin $A_4$,
13-[2-(4-Piperidinocarbonylaminophenyl)ethoxy]milbemycin $A_4$,
13-[2-(4-Acetamidomethylphenyl)ethoxy]milbemycin $A_4$,
13-[2-(4-Phenylacetamidomethylphenyl)ethoxy]milbemycin $A_4$,
13-[2-(4-Benzamidomethylphenyl)ethoxy]milbemycin $A_4$,
13-[2-(4-Methoxycarbonylaminophenyl)ethoxy]milbemycin $A_4$,
13-[2-(4-Methoxycarbonylaminophenyl)ethoxy]milbemycin $A_4$ 5-oxime,
13-[2-(4-Ethoxycarbonylaminophenyl)ethoxy]milbemycin $A_4$,
13-[2-(4-Ethoxycarbonylaminophenyl)ethoxy]milbemycin D,
13-Deoxy-13-[2-(4-ethoxycarbonylaminophenyl)ethoxy]-22,23-dihydroavermectin $B_{1a}$-aglycone.
13-[2-(4-Ethoxycarbonylamino-3-methoxyphenyl)ethoxy]milbemycin $A_4$,
13-[2-(3-Ethoxycarbonylaminophenyl)ethoxy]milbemycin $A_4$,
13-[2-(2-Ethoxycarbonylaminophenyl)ethoxy]milbemycin $A_4$,
13-[2-(4-Propoxycarbonylaminophenyl)ethoxy]milbemycin $A_4$,
13-[2-(4-Isopropoxycarbonylaminophenyl)ethoxy]milbemycin $A_4$,
13-[2-(4-Butoxycarbonylaminophenyl)ethoxy)milbemycin $A_4$,
13-[2-(4-Vinyloxycarbonylaminophenyl)ethoxy]milbemycin $A_4$,
13-[2-(4-Allyloxycarbonylaminophenyl)ethoxy]milbemycin $A_4$,
13-[2-(4-Cyclohexyloxycarbonylaminophenyl)ethoxy]milbemycin $A_4$,
13-[2-(4-Benzyloxycarbonylaminophenyl)ethoxy]milbemycin $A_4$,
13-{2-[4-(4-Nitrobenzyloxycarbonylamino)phenyl]ethoxy milbemycin $A_4$,
13-{2-[4-(4-Methoxybenzyloxycarbonylamino)phenyl]ethoxy milbemycin $A_4$,
13-[2-(4-Methoxycarbonylaminomethylphenyl)ethoxy milbemycin $A_4$,
13-[2-(4-Ethoxycarbonylaminophenyl)ethoxy]milbemycin $A_4$,
13-[2-(4-Ethoxycarbonylaminomethylphenyl)ethoxy]milbemycin $A_4$
13-[2-(4-Ethylthiothiocarbonylaminophenyl)ethoxy]milbemycin $A_4$
13-{2-(4-Methanesulfonylaminophenyl)ethoxy]milbemycin $A_4$,
13-[2-(4-Ethanesulfonylaminophenyl)ethoxy]milbemycin $A_4$,
13-[2-(4-Benzenesulfonylaminophenyl)ethoxy]milbemycin $A_4$,
13-{2-[4-(p-Tosylamino)phenyl]ethoxy milbemycin $A_4$,
13-{2-[4-(3-Methylureido)phenyl]ethoxy milbemycin $A_4$,
13-{2-[4-(3-Chloromethylureido)phenyl]ethoxy milbemycin $A_4$, 13-{2-[4-(3-Methylureido)phenyl]ethoxy milbemycin D,
13-Deoxy-13-{2-[4-(3-methylureido)phenyl]ethoxy-22,23-dihydroavermectin $B_{1a}$-aglycone,
13-{2-[4-(3-Ethylureido)phenyl]ethoxy milbemycin $A_4$,
13-{2-[4-(3-Ethylureido)-3-methoxyphenyl]ethoxy milbemycin $A_4$,
13-{2-[4-(3-Ethylureido)-3-fluorophenyl]ethoxy milbemycin $A_4$,
13-{2-[4-(3-Propylureido)phenyl]ethoxy milbemycin $A_4$,
13-{2-[4-(3-Isopropylureido)phenyl]ethoxy milbemycin $A_4$,
13-{2-[4-(3-Butylureido)phenyl]ethoxy milbemycin $A_4$,
13-{2-[4-(3-Benzylureido)phenyl]ethoxy milbemycin $A_4$,
13-{2-[4-(3-Methoxycarbonylmethylureido)phenyl]ethoxy milbemycin $A_4$,
13-{2-[4-(3-Cyclohexylureido)phenyl]ethoxy milbemycin $A_4$,
13-{2-[4-(3-Allylureido)phenyl]ethoxy milbemycin $A_4$,
13-{2-[4-(3-Phenylureido)phenyl]ethoxy milbemycin $A_4$,
13-{2-[4-(3-Phenylureido)-3-methoxyphenyl]ethoxy milbemycin $A_4$,
13-{2-[4-(3-p-Fluorophenylureido)phenyl]ethoxy milbemycin $A_4$,
13-{2-[4-(3-p-Fluorophenylureido)phenyl]ethoxy milbemycin $A_4$,
13-{2-[4-(3-p-Nitrophenylureido)phenyl]ethoxy milbemycin $A_4$,
13-{2-[4-(3-p-Methoxyphenylureido)phenyl]ethoxy milbemycin $A_4$,
13-{2-[4-(3-p-Aminophenylureido)phenyl]ethoxy milbemycin $A_4$,
13-{2-[4-(3-p-Acetamidophenylureido)phenyl]ethoxy milbemycin $A_4$,
13-{2-[4-(3-Methylureidomethyl)phenyl]ethoxy milbemycin $A_4$
13-{2-[4-(3-Phenylureidomethyl)phenyl]ethoxy milbemycin $A_4$,
13-{2-[4-(3-Methylthioureido)phenyl]ethoxy milbemycin $A_4$,
13-{2-[4-(3-Ethylthioureido)phenyl]ethoxy milbemycin $A_4$,
13-{2-[4-(3-Phenylthioureido)phenyl]ethoxy milbemycin $A_4$,
13-[2-(4-Acetimidoylaminophenyl)ethoxy]milbemycin $A_4$,
13-{2-[4-(Propanesulfonylamino)phenyl]ethoxy milbemycin $A_4$,
13-{2-[4-(Isopropanesulfonylamino)phenyl]ethoxy milbemycin $A_4$,
13-{2-[4-(Isonicotinoylamino)phenyl]ethoxy milbemycin $A_4$,
13-{2-[4-(Methoxyacetamido)phenyl]ethoxy milbemycin $A_4$,
13-{2-[4-(Fluoroacetamido)phenyl]ethoxy milbemycin $A_4$,
13-{2-[4-(Difluoroacetamido)phenyl]ethoxy milbemycin $A_4$,
13-{2-[4-(2-Cyanopropionamido)phenyl]ethoxy milbemycin $A_4$,
13-{2-[4-(Methoxalylamino)phenyl]ethoxy milbemycin $A_4$,
13-{2-[4-(Pyruvoylamino)phenyl]ethoxy milbemycin $A_4$,
13-{2-[4-(Methoxycarbonylacetamido)phenyl]ethoxy milbemycin $A_4$,
13-{2-[4-(Ethoxycarbonylacetamido)phenyl]ethoxy milbemycin $A_4$,
13-{2-[4-(Cyclopropylcarbonylamino)phenyl]ethoxy milbemycin $A_4$,
13-{2-[4-(Cyclobutylcarbonylamino)phenyl]ethoxy milbemycin $A_4$,
13-{2-[4-(Cinnamoylamino)phenyl]ethoxy milbemycin $A_4$,
13-{2-[4-(Methacryloylamino)phenyl]ethoxy milbemycin $A_4$,
13-{2-[4-(Tetroloylamino)phenyl]ethoxy milbemycin $A_4$,
13-{2-[4-(Pyrazin-2-ylcarbonylamino)phenyl]ethoxymilbemycin $A_4$,
13-{2-[4-(3,4-Dihydro-2H-pyran-2-ylcarbonylamino)phenyl]ethoxymilbemycin $A_4$,
13-{2-[4-(4-Methoxycarbonylbenzoylamino)phenyl]ethoxy milbemycin $A_4$,
13-{2-[4-(1-t-Butoxycarbonylpiperidin-4-ylcarbonylamino)phenyl]ethoxy milbemycin $A_4$,
13-{2-[4-(Glycylamino)phenyl]ethoxy milbemycin $A_4$,
13-{2-[4-(N-Acetylglycylamino)phenyl]ethoxy milbemycin $A_4$,
13-{2-[4-(Ethoxycarbonylglycylamino)phenyl]ethoxy milbemycin $A_4$,
13-{2- {4-[(3-Methylureido)acetamido]phenyl ethoxy milbemycin $A_4$,
13-{2-{4-[(3-Phenylureido)acetamido]phenyl ethoxy milbemycin $A_4$,
13-[2-(4-Ethoxycarbonylamino-3-methoxyphenyl)ethoxy]milbemycin $A_4$,
13-[2-(4-Butanesulfonylaminophenyl)ethoxy] milbemycin $A_4$,
13-[2-(4-Cyanomethanesulfonylaminophenyl)ethoxy] milbemycin $A_4$,
13-{2-[4-(4-Methoxybenzenesulfonylamino)phenyl]ethoxy milbemycin $A_4$,
13-{2-[4-(1,2,4-triazolo[4.3-a]pyridin-3-on-2-ylcarbonylamino)phenyl]ethoxy milbemycin $A_4$,
13-{2-{4-[3-(2-Chloroethyl)ureido]phenyl ethoxy milbemycin $A_4$,
13-{2-[p-3-(2-Hydroxyethyl)ureidophenyl]ethoxy milbemycin $A_4$,
13-[2-(4-Ureidophenyl)ethoxy]milbemycin $A_4$,
13-{2-[4-(3,3-Dimethylureido)phenyl]ethoxy milbemycin $A_4$,
13-{2-[p-3-(2-Mercaptoethyl)ureidophenyl]ethoxy milbemycin $A_4$,
13-{2-[4-(3-Cyclopropylureido)phenyl]ethoxy milbemycin $A_4$,
13-{2-[p-3-(2-Pyridyl)ureidophenyl]ethoxy milbemycin $A_4$,
13-{2-[p-3-(2-Thiazolinyl)ureidophenyl]ethoxy milbemycin $A_4$,
13-{2-[p-3-(2-Thiazolyl)ureidophenyl]ethoxy milbemycin $A_4$,
13-{2-[4-(3-Propionylureido)phenyl]ethoxy milbemycin $A_4$, 13-{2-[4-(3-Benzoylureido)phenyl]ethoxy milbemycin $A_4$, 13-{2-[4-(3-Methanesulfonylureido)phenyl]ethoxy milbemycin $A_4$, 13-[2-(4-Morpholinocarbonylaminophenyl)ethoxy] milbemycin $A_4$, 13-[2-(4-Carbazoylaminophenyl)ethoxy]milbemycin $A_4$, 13-{2-[4-(2-Methylcarbazoylamino)phenyl]ethoxy milbemycin $A_4$, 13-{2-[4-(3,3-Dimethylcarbazoylamino)phenyl]ethoxy milbemycin $A_4$, 13-{2-[4-(3-Phenylcarbazoylamino)phenyl]ethoxy milbemycin $A_4$, 13-{2-[p-3-(2-Pyridyl)carbazoylaminophenyl]ethoxy milbemycin $A_4$, 13-{2-[4-(3-Acetylcarbazoylamino)phenyl]ethoxy milbemycin $A_4$, 13-{2-[4-(3-Benzoylcarbazoylamino)phenyl]ethoxy milbemycin $A_4$, 13-{2-[4-(3-Morpholinoureido)phenyl]ethoxy milbemycin $A_4$, 13-{2-[p-3-(Hexahydro-1$\underline{H}$-azepin-1-yl)ureidophenyl] ethoxy milbemycin $A_4$, 13-[2-(4-Formimidoylaminophenyl)ethoxy]milbemycin $A_4$, 13-[2-(4-Benzimidoylaminophenyl)ethoxy]milbemycin $A_4$, 13-{2-[p-3-(Methoxycarbonyl)guanidinophenyl]ethoxy milbemycin $A_4$, 13-{2-[p-2,3-Bis(methoxycarbonyl)guanidinophenyl] ethoxy milbemycin $A_4$, 13-[2-(4-Benzenesulfinylaminophenyl)ethoxy] milbemycin $A_4$, 13-{2-[p-($\underline{N}$-Ethoxycarbonyl)methylaminophenyl]ethoxy milbemycin $A_4$, 13-{2-[p-$\underline{N}$-(4-Methylphenyl)carbamoylphenyl]ethoxy milbemycin $A_4$, Of these, the preferred compounds are as follows:

13-[2-(4-Acetamidophenyl)ethoxy]milbemycin $A_4$

13-[2-(4-Cyanoacetamidophenyl)ethoxy]milbemycin $A_4$

13-{2-[4-(2-Cyanopropionamido)phenyl] ethoxy}milbemycin $A_4$

13-[2-(4-Methoxyacetamidophenyl)ethoxy]milbemycin $A_4$

13-{2-[4-(Cyclopropylcarbonylamino)phenyl] ethoxy}milbemycin $A_4$

13-{2-[4-(Cyclobutylcarbonylamino)phenyl] ethoxy}milbemycin $A_4$

13-{2-[4-(4-Cyanobenzamido)phenyl] ethoxy}milbemycin $A_4$

13-[2-(4-Methoxycarbonylaminophenyl)ethoxy] milbemycin $A_4$

13-[2-(4-Vinyloxycarbonylaminophenyl)ethoxy] milbemycin $A_4$

13-{2-[4-(3-Methylureido)phenyl]ethoxy}milbemycin $A_4$

13-{2-[4-(3-Phenylureido)phenyl]ethoxy}milbemycin $A_4$

13-{2-[4-(3-Cyclohexylureido)phenyl] ethoxy}milbemycin $A_4$

13-[2-(4-Methanesulfonylaminophenyl)ethoxy] milbemycin $A_4$

13-[2-(4-Ethanesulfonylaminophenyl)ethoxy] milbemycin $A_4$

13-{2-[4-(3,3-Dimethylcarbazoylamino)phenyl] ethoxy}milbemycin $A_4$

13-[2-[4-(3-o-Fluorophenylureido)phenyl] ethoxy}milbemycin $A_4$

13-{2-[4-(3-p-Fluorophenylureido)phenyl] ethoxy}milbemycin $A_4$

13-{2-[4-(3-p-Methoxyphenylureido)phenyl] ethoxy}milbemycin $A_4$

Also preferred are salts, where available of the above compounds.

The compounds of the formula $(I)_w$ of the present invention may be prepared by a variety of processes known in the art for the preparation of compounds of this type. In general terms a suitable preparative procedure comprises reacting a compound of formula $(IV)_w$:

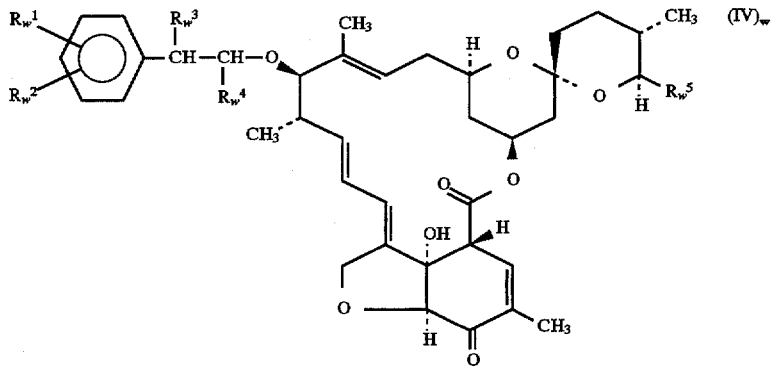

(in which $R_w^1$, $R_w^2$, $R_w^3$, $R_w^4$ and $R_w^5$ are as defined above) with a reducing agent to prepare a compound of formula $(I)_w$ in which $X_w$ represents a hydroxy group and, if required, acylating said compound to prepare a compound of formula $(I)_w$ in which $X_w$ represents said alkanoyloxy group, or by reacting said compound of formula $(IV)_w$ with hydroxylamine or a salt thereof to prepare a compound of formula $(I)_w$ in which X represents a hydroxyimino group.

The compound of formula $(IV)_w$, which is the starting material referred to above, may be prepared by reacting a compound of formula $(III)_w$:

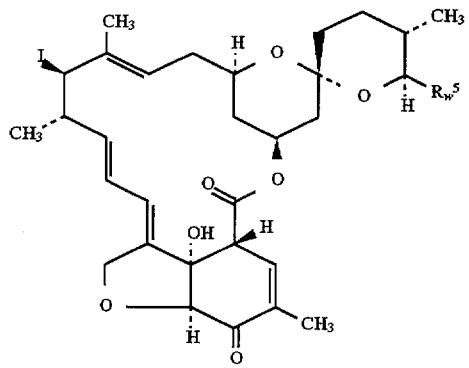 (III)$_w$
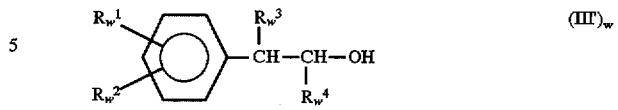 (III')$_w$
(in which $R_w^5$ is as defined above) with a compound of formula (III')$_w$:
(in which $R_w^1$, $R_w^2$, $R_w^3$ and $R_w^4$ are as defined above).
In more detail, the compounds of formula (I)$_w$ of the present invention can be prepared from a 13-iodomilbemycin of formula (III)$_w$ as shown in the following Reaction Scheme A$_w$:

Reaction Scheme A:
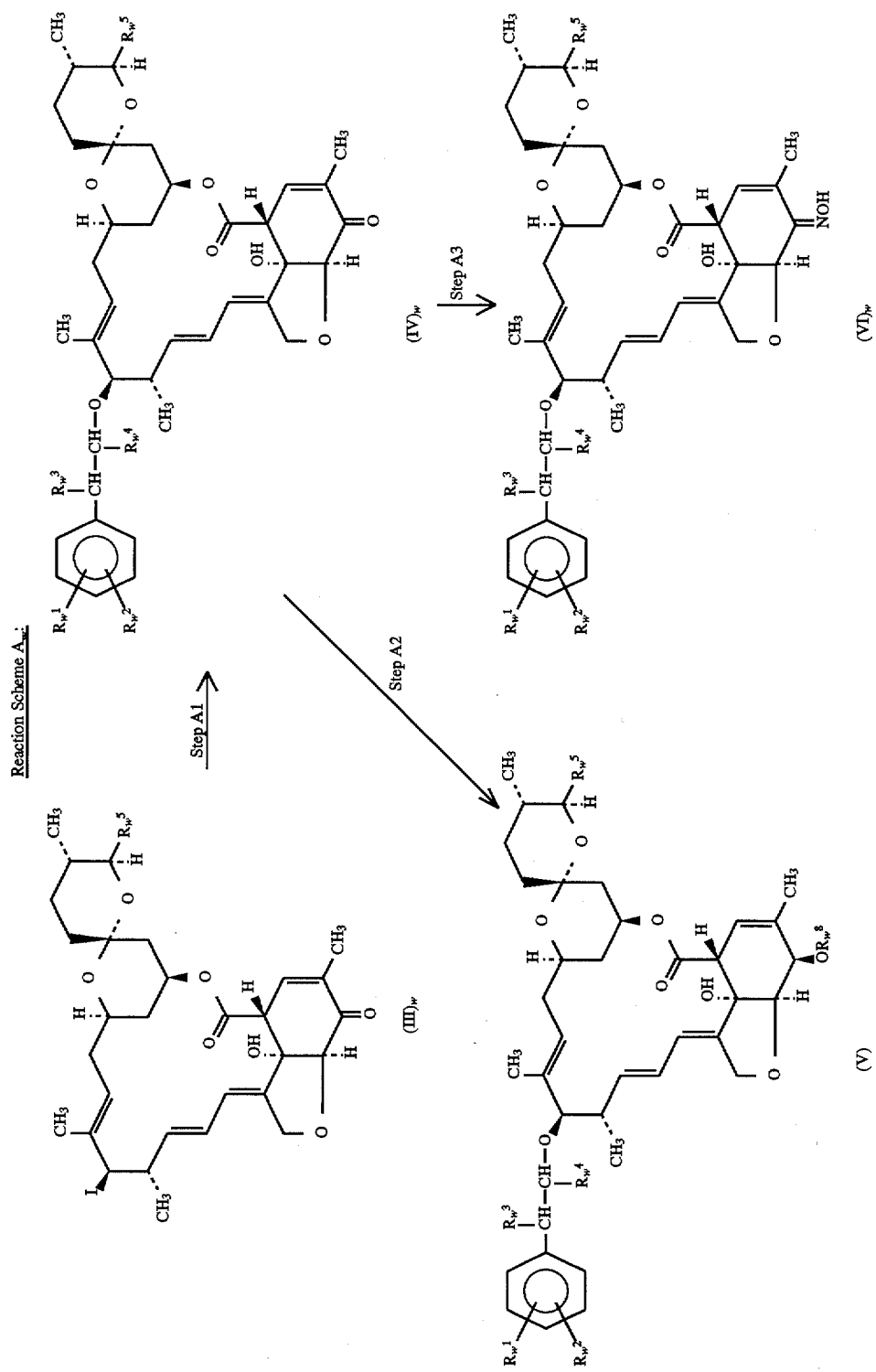

In the above formulae, $R_w^1$, $R_w^2$, $R_w^3$, $R_w^4$ and $R_w^5$ are as defined above and $R_w^8$ represents a hydrogen atom or a $C_1$–$C_5$ alkanoyl group or substituted $C_1$–$C_5$ alkanoyl group having at least one substituent selected from the group consisting of substituents $(d)_w$, defined above (i.e. the alkanoyl groups defined above for the alkanoyloxy groups of $X_w$).

In Step A1, a compound of formula $(IV)_w$ is prepared by reacting a compound of formula $(III)_w$ with a phenethyl alcohol of formula $(III')_w$ in the presence of a catalyst. Any catalyst capable of catalysing such etherification reactions, as are well known in the art, may equally be employed in this reaction, without any particular restriction. Examples of suitable catalysts include oxides and salts of mercury or silver, preferably a silver compound such as silver oxide, silver perchlorate or silver trifluoromethanesulfonate, or a mercury compound such as mercury oxide, mercury iodide, mercury bromide or mercury trifluoromethanesulfonate.

In certain cases, the reaction may be accelerated by addition of an acid-binding agent. There is no particular limitation on the nature of such an acid-binding agent, provided that it has no adverse effect on the reaction, but 2,6-lutidine and calcium carbonate are preferred examples.

There is no particular limitation on the nature of the solvent employed in the reaction, provided that it has no adverse effect on the reaction and that it is capable of solubilizing the starting compound, at least to some extent. Phenethyl alcohol itself can be employed as the solvent, but preferred solvents include: aromatic hydrocarbons, such as benzene, toluene or xylene; halogenated hydrocarbons, especially halogenated aliphatic hydrocarbons, such as methylene chloride, 1,2-dichloroethane or chloroform; esters, such as ethyl acetate or propyl acetate; ethers, such as diethyl ether, tetrahydrofuran, dioxane or dimethoxyethane; amides, such as dimethylformamide, dimethylacetamide or hexamethylphosphoric triamide; and sulfoxides, such as dimethyl sulfoxide.

The reaction can take place over a wide range of temperatures, and the precise reaction temperature is not critical to the invention. In general, we find it convenient to carry out the reaction at a temperature from –10° C. to 100° C., preferably from 0° C. to 50° C. The time required for the reaction may also vary widely, depending on many factors, notably the reaction temperature and the nature of the reagents and of the solvent. However, provided that the reaction is effected under the preferred conditions outlined above, a period of from 1 hour to 2 days will usually suffice.

After completion of the reaction, the reaction product may be recovered from the reaction mixture by conventional means. For example, the reaction mixture may be diluted with a water-immiscible organic solvent, after which the insoluble materials are removed by filtration, if necessary. The filtrate may then be washed successively with an aqueous solution of potassium iodide, an acid and water, and the solvent may be removed by distillation to afford the desired product. The product may, if required, be further purified by such conventional techniques as recrystallization or the various chromatography techniques, notably column chromatography.

In Step A2, a compound of formula $(V)_w$ is prepared by reducing the carbonyl group at the 5-position of the compound of formula $(IV)_w$ to a hydroxy group, which, if required, may then be subjected to acylation to give a compound of formula $(V)_w$ in which $R_w^8$ represents an alkanoyl group. There is no particular limitation on the nature of the reducing agent to be used in this reduction, provided that it can reduce the carbonyl group and has no adverse effect on the other functional groups in the compound of formula $(IV)_w$. Such reducing agents include, for example, hydride agents, such as sodium borohydride or diborane, preferably sodium borohydride.

There is equally no particular limitation on the nature of the solvent, provided that it has no adverse effect on the reaction, but a lower alcohol (such as methanol, ethanol or propanol) is preferably used when sodium borohydride is employed as the reducing agent.

The reaction can take place over a wide range of temperatures, and the precise reaction temperature is not critical to the invention. In general, we find it convenient to carry out the reaction at a temperature from 0° C. to 50° C. The time required for the reaction may also vary widely, depending on many factors, notably the reaction temperature and the nature of the reagents. However, provided that the reaction is effected under the preferred conditions outlined above, a period of from 5 minutes to 2 hours will usually suffice.

After completion of the reaction, the reaction product can be recovered easily from the reaction mixture by conventional means. For example, the reaction mixture may be diluted with a water-immiscible organic solvent and washed with water, after which the solvent may be removed by distillation to afford desired product. The product may, if required, be further purified by such conventional techniques as recrystallization or the various chromatography techniques, notably column chromatography.

The reduction product thus prepared may, if required, be acylated in an inert solvent using as the acylating agent an acid corresponding to the alkanoyl group which it is desired to introduce or using a reactive derivative of such an acid. The reaction can be carried out using conventional esterification techniques. Examples of suitable active derivatives of the acid include any of those commonly used for esterification such as acid halides (e.g. an acid chloride or acid bromide), acid anhydrides, mixed acid anhydrides, reactive esters (e.g. the N-hydroxybenztriazole ester) and reactive amides (e.g. the imidazolide).

Where the acid itself is employed, a dehydrating agent (such as dicyclohexylcarbodiimide, p-toluenesulfonic acid or sulfuric acid) is preferably also used. Where a reactive derivative of an acid is employed, an acid-binding agent is preferably also employed. There is no particular limitation on nature of the acid-binding agent to be used, provided that it has the ability to eliminate an acid, for example, an organic amine such as triethylamine, N,N-diethylaniline, pyridine, 4-dimethylaminopyridine or 1,8-diazabicyclo[5.4.0]undecene-7.

There is no particular restriction on the nature of the solvent to be employed, provided that it has no adverse effect on the reaction or on the reagents involved. Examples of suitable solvents include: hydrocarbons, which may be aliphatic, aromatic or cycloaliphatic, such as hexane, benzene, toluene or xylene; halogenated hydrocarbons, especially halogenated aliphatic hydrocarbons, such as methylene chloride, 1,2-dichloroethane or chloroform; esters, such as ethyl acetate or propyl acetate; and ethers, such as diethyl ether, tetrahydrofuran, dioxane or dimethoxyethane.

After completion of the reaction, the reaction product can easily be recovered from the reaction mixture by conventional means. For example, the reaction mixture may be diluted with a water-immiscible organic solvent and washed successively with an acid, an alkali and water, after which the solvent may be removed by distillation to afford the desired product. The product may, if required, be further purified by such conventional techniques as recrystallization or the various chromatography techniques, notably column chromatography.

In Step A3 a compound of formula $(VI)_w$ is prepared by oximation at the 5-position of the compound of formula $(IV)_w$ with hydroxylamine or with a salt thereof (e.g. a salt with a mineral acid such as hydrochloric acid, nitric acid or sulfuric acid).

The reaction is usually carried out in an inert solvent, the nature of which is not critical, provided that it has no adverse effect on the reaction or on the reagents involved. Examples of suitable solvents include: alcohols, such as methanol or ethanol; ethers, such as tetrahydrofuran or dioxane; aliphatic acids, such as acetic acid; or a mixture of water with any one or more of these solvents.

The reaction can take place over a wide range of temperatures, and the precise reaction temperature is not critical to the invention. In general, we find it convenient no carry out the reaction at a temperature from 10° C. to 80° C. The time required for the reaction may also vary widely, depending on many factors, notably the reaction temperature and the nature of the reagents. However, provided that the reaction is effected under the preferred conditions outlined above, a period of from 1 to 24 hours will usually suffice.

After completion of the reaction, the reaction product can easily be recovered from the reaction mixture by conventional means. For example, the reaction mixture may be diluted with a water-immiscible organic solvent and washed with water, after which the solvent may be removed by distillation to afford the desired product. The product may, if required, be further, purified by such conventional techniques as recrystallization or the various chromatography, techniques, notably column chromatography.

The compound of formula $(V)_w$ wherein $R_w^1$ is a substituted amino group can be prepared as illustrated in the following Reaction Scheme $B_w$:

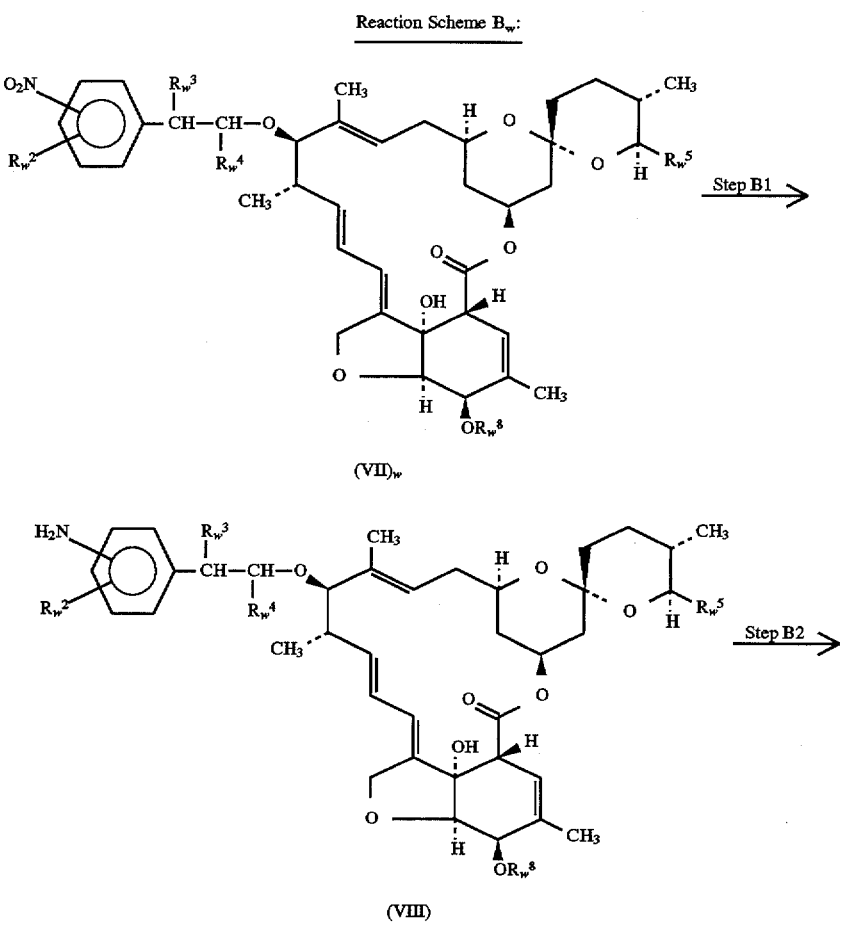

-continued
Reaction Scheme $B_w$:

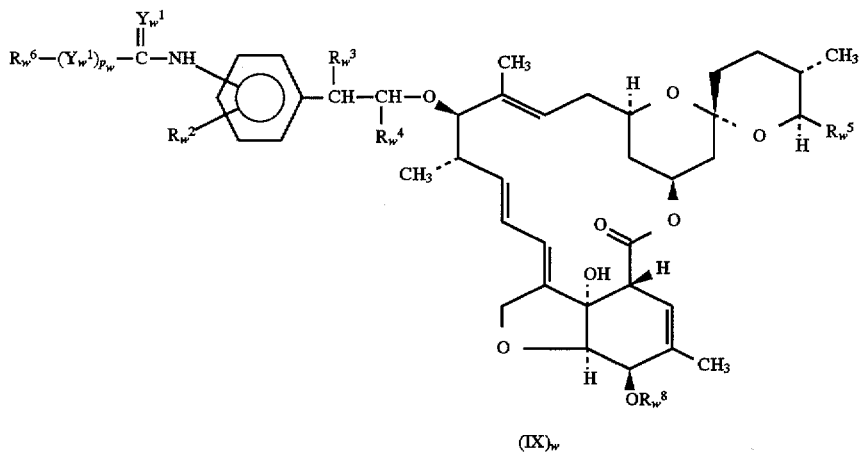

(IX)$_w$

In the above formulae, $R_w^2$, $R_w^3$, $R_w^4$, $R_w^5$, $R_w^6$ and $R_w^8$ are as defined above $Y_w$, represents an oxygen atom, a sulfur atom or an imino group, and $p_w$ represents 0 or 1.

In Step B1 a compound of formula (VIII)$_w$ is prepared by reducing the nitro group of a compound of formula (VII)$_w$ to give an amino group. This may by effected by a conventional reducing method for reducing a nitro group to an amino group. One such method is catalytic reduction using a precious metal catalyst. Examples of catalysts which are preferably employed include palladium-on-carbon, palladium-on-barium sulfate and platinum oxide.

The reaction is normally and preferably effected in the presence of a solvent, and there is no particular restriction on the nature of the solvent to be employed, provided that it has no adverse effect on the reaction or on the reagents involved. Examples of suitable solvents include: alcohols, such as methanol or ethanol; ethers, such as tetrahydrofuran or dioxane; and esters, such as ethyl acetate.

The reaction can take place over a wide range of temperatures, and the precise reaction temperature is not critical to the invention. In general, we find it convenient to carry out the reaction at a temperature from 10° C. to 80° C. The time required for the reaction may also vary widely, depending on many factors, notably the reaction temperature and the nature of the reagents. However, provided that the reaction is effected under the preferred conditions outlined above, a period of from 10 minutes to 5 hours will usually suffice.

An alternative preferred reducing method is reduction with zinc powder in acetic acid. This reaction is preferably carried out at a temperature ranging from 0° C. to room temperature, and the reaction time is usually in the range of from 10 minutes to 2 hours.

After completion of the reaction, the reaction product can easily be recovered from the reaction mixture by conventional means. For example, the reaction mixture may be diluted with a water-immiscible organic solvent, and the insoluble materials, if necessary, removed by filtration. The filtrate may then be washed with water, and the solvent may be removed by distillation to afford the desired product. The product may, if required, be further purified by such conventional techniques as recrystallization or the various chromatography techniques, notably column chromatography.

In Step B2 a compound of formula (IX)$_w$ is prepared by reacting the compound of formula (VIII)$_w$ with a reagent that is reactive with the amino group, to introduce the group of formula $R^6$—$(Y_w')_{n_w}$—$C(=Y_w')$—NH—.

The nature of the reagent to be employed will, of course, be dictated by the nature of the group which it is desired to introduce. However, in general, it may be a reactive derivative of a carboxylic acid of the type commonly used as an acylating agent such as an acid halide, an acid anhydride, a mixed acid anhydride, a reactive ester or a reactive amide. Alternatively, it may be: a chloroformate, such as methyl chloroformate or benzyl chloroformate: a thiochloroformate, such as ethyl chlorothioformate: a sulfonyl chloride, such as methanesulfonyl chloride or benzenesulfonyl chloride; an isocyanate; a thioisocyanate; or an imino ether. Alternatively, a carboxylic acid may be used as such, provided that it is activated, for example with dicyclohexylcarbodiimide.

When a halide, such as an acid halide, is employed as the reagent, it is usually preferred to carry out the reaction in the presence of an organic base, such as triethylamine, N,N-diethylaniline, pyridine, 4-dimethylaminopyridine or 1,8-diazabicyclo[5.4.0]undecene, as an acid-binding agent.

The reaction can take place over a wide range of temperatures, and the precise reaction temperature is not critical to the invention. In general, we find it convenient to carry out the reaction at a temperature from 0° C. to 80° C., preferably from 0° C. to room temperature. The time required for the reaction may also vary widely, depending on many factors, notably the reaction temperature and the nature of the reagents. However, provided that the reaction is effected under the preferred conditions outlined above, a period of from 10 minutes to 10 hours will usually suffice.

After completion of the reaction, the reaction product can easily be recovered from the reaction mixture by conventional means. For example, the reaction mixture may be diluted with a water-immiscible organic solvent, and the insoluble materials may then be removed, if required, by filtration and washed with water, after which the solvent may be removed by distillation to afford the desired product. The product may, if required, be further purified by such conventional techniques as recrystallization or the various chromatography techniques, notably column chromatography.

The compound of formula (III)$_w$, which is used as the starting material can advantageously be synthesized from 13-hydroxy-5-oxomilbemycin, which is represented by the general formula (X)$_w$, as illustrated in the following Reaction Scheme $C_w$:

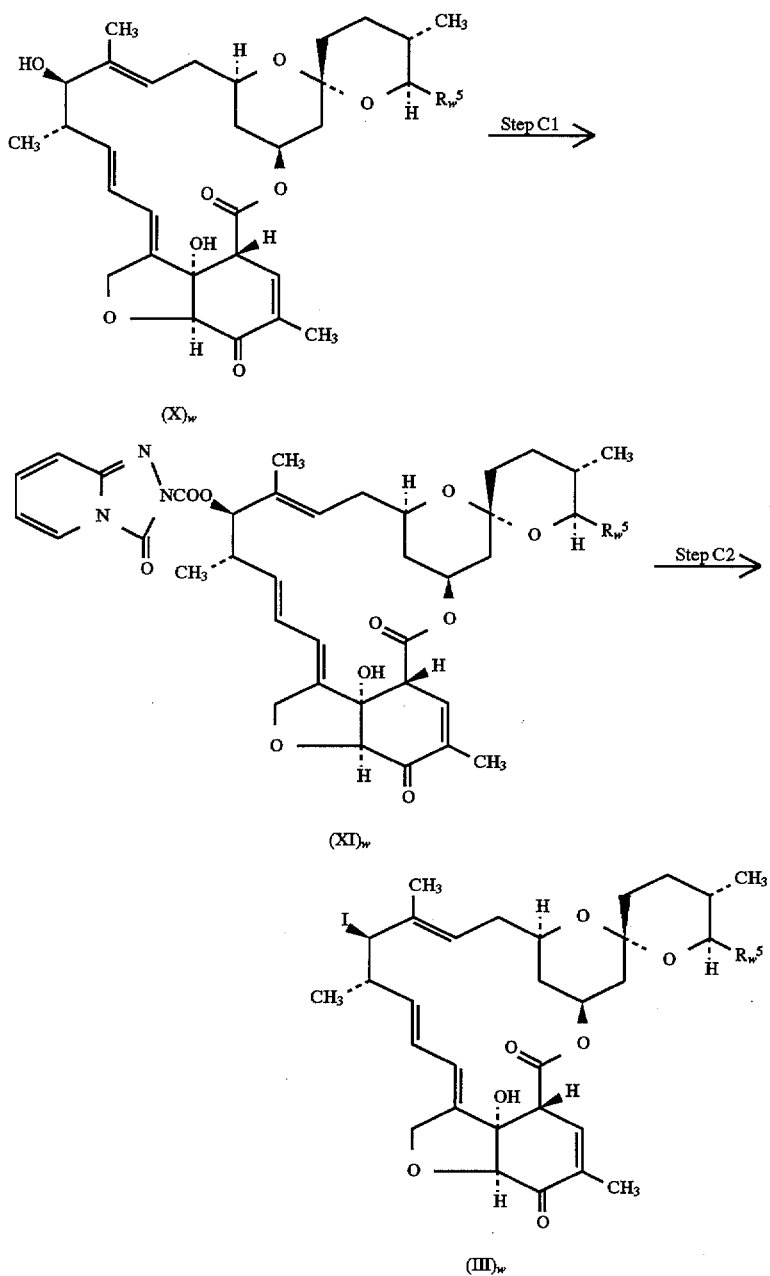

In the above formulae, $R_w^5$, is as defined above.

In Step C1 a compound of formula $(XI)_w$ is prepared by reacting the compound of formula $(X)_w$ with 2-chloroformyl-1,2,4-triazolo[4.3a]pyridin-3-one in the presence of an acid-binding agent.

There is no particular limitation on the nature of the acid-binding agent to be employed provided that it has the ability to eliminate any acid produced. For example, an organic amine, such as triethylamine, N,N-diethylaniline, pyridine, 4-dimethylaminopyridine or 1,8-diazabicyclo[5.4.0]undecene, may be used.

The reaction is also preferably effected in the presence of an inert solvent, the nature of which is not critical, provided that it has no adverse effect on the reaction or on the reagents involved. Examples of suitable solvents include: hydrocarbons, which may be aliphatic, aromatic or cycloaliphatic, such as hexane, benzene, toluene or xylene; halogenated hydrocarbons, especially halogenated aliphatic hydrocarbons, such as methylene chloride, 1,2-dichloroethane or chloroform; esters, such as ethyl acetate or propyl acetate; and ethers, such as diethyl ether, tetrahydrofuran, dioxane or dimethoxyethane.

The reaction can take place over a wide range of temperatures, and the precise reaction temperature is not critical to the invention. In general, we find it convenient to carry out the reaction at a temperature from 0° C. to 50° C. The time required for the reaction may also vary widely, depending on many factors, notably the reaction temperature and the nature of the reagents. However, provided that the reaction is effected under the preferred conditions outlined above, a period of from 5 minutes to 2 hours will usually suffice.

After completion of the reaction, the reaction product can easily be recovered from the reaction mixture by conventional means. For example, the reaction mixture may be diluted with a water-immiscible organic solvent, the insoluble materials may then be removed, if required, by filtration and washed successively with an aqueous solution of potassium iodide, an acid and water, after which the solvent may be removed by distillation to afford the desired product.

In Step C2 13-iodomilbemycin, which is represented by formula $(III)_w$, is prepared by reacting the compound of formula $(XI)_w$ with zinc iodide.

This reaction is usually carried out in a solvent, There is no particular restriction on the nature of the solvent to be employed, provided that it has no adverse effect on the reaction or on the reagents involved. Examples of suitable solvents include: hydrocarbons, which may be aliphatic, aromatic or cycloaliphatic, such as hexane, benzene, toluene or xylene; halogenated hydrocarbons, especially halogenated aliphatic hydrocarbons, such as methylene chloride, 1,2-dichloroethane or chloroform; esters, such as ethyl acetate or propyl acetate; and ethers, such as diethyl ether, tetrahydrofuran, dioxane or dimethoxyethane.

The reaction can take place over a wide range of temperatures, and the precise critical temperature is not critical to the invention. In general, we find it convenient to carry out the reaction at a temperature from 0° C. to room temperature. The time required for the reaction may also vary widely, depending on many factors, notably the reaction temperature and the nature of the reagents. However, provided that the reaction is effected under the preferred conditions outlined above, a period of from 10 minutes to 2 hours will usually suffice.

After completion of the reaction, the reaction product can easily be recovered from the reaction mixture by conventional means. For example, the insoluble materials may be removed by filtration and the filtrate washed with water, after which the solvent may be removed by distillation to afford the desired product. The product may, if required, be further purified by such conventional techniques as recrystallization or the various chromatography techniques, notably column chromatography.

The compound of formula $(X)_w$, which is, therefore, the ultimate starting material for the above sequence reactions, can be prepared from the natural or semisynthetic milbemycins or avermectins by the method disclosed in Japanese Patent Application Kokai No. Sho 61-103884.

The milbemycins and analogous natural products are generally obtained as mixtures at various ratios of related compounds, and they may be reacted after being separated into the various fractions or they may be used in the above reactions as mixtures, whether the natural mixture or an artificially produced mixture. Therefore, the compound used in each step of the above reactions may be either a single compound or a mixture of compounds. Accordingly, the compound of formula (I) or formula $(I)_w$ may be prepared as a single compound or as a mixture of compounds, and, if prepared as a mixture of compounds, may be used as such or may be separated into the individual compounds prior to use.

The compounds of the invention have a strong acaricidal activity against, for example, adults, imagos and eggs of Tetranychus, Panonychus (e.g. *Panonychus ulmi* and *Panonychus citri*), *Aculopa pelekassi* and rust mites, which are parasitic to fruit trees, vegetables and flowers. They are also active against Ixodidae, Dermanyssidae and Sarcoptidae, which are parasitic to animals. Surprisingly, they have a strong activity even against acarids which are resistant to the known acaricides, which have recently started to become a great problem. Further, they are active against: ectoparasites, such as Oestrus, Lucilia, Hypoderma, Gautrophilus, lice and fleas, which are parasitic to animals and birds, particularly livestock and poultry; domestic insects, such as cockroaches and houseflies; and various harmful insects in agricultural and horticultural areas, such as aphids and larval Lepidoptera. They are also effective against Meloidogyne, Bursaphelenchus and Rhizoglyphus in the soil, and against insects of the orders Coleoptera, Homoptera, Heteroptera, Diptera, Thysanoptera, Orthoptera, Anoplura, Siphonaptera, Mallophage, Thysanura, Isoptera, Psocoptera, and Hymenoptera.

The compounds of the invention equally can be used to control other plant-damaging insects, particularly insects that damage plants by eating them. The compounds can be used to protect both ornamental plants and productive plants, particularly cotton (e.g. against *Spodoptera littoralis* and *Heliothis virescens*), as well as vegetable crops (e.g. against *Leptinotarsa decemlineata* and *Myzus persicae*) and rice crops (e.g. against *Chilo suppressalis* and Laodelphax).

Accordingly, the compounds of the invention can be used to treat all manner of plants (as well as the seeds from which such plants are grown and the environment, whether for growth or storage, containing such plants) to protect them from insects such as those exemplified above. Such plants include cereals (e.g. maize or rice), vegetables (e.g. potatoes or soybeans), fruits and other plants (e.g. cotton).

The compounds of the invention can similarly be used to protect animals from a variety of ectoparasites, by applying the compounds to the animals or to the animals' environment, e.g. livestock housing, animal boxes, abattoirs, pasture land and other grasslands, as well as to any other places liable to be infested. The compounds may also be applied to external parts of the animals, preferably before they are infested.

Moreover, the compounds of the invention are effective against various parasitical helminths. These parasites can attack livestock, poultry and pet animals (such as pigs, sheep, goats, cows, horses, dogs, cats and fowl) and can cause grave economic damage. Among the helminths, the nematodes in particular often cause serious infection. Typical genera of nematodes which are parasitic on these animals and against which the compounds of the invention are effective include:

Haemonchus, Trichostrongylus, Ostertagia, Nematodirus, Cooperia, Ascaris, Bunostomum, Oesophagostomum, Chabertia, Trichuris, Strongylus, Trichonema, Dictyocaulus, Capillaria, Heterakis, Toxocara, Ascaridia, Oxyuris, Ancylostoma, Uncinaria, Toxascaris and Parascaris.

Certain parasitical species of the genera Nematodirus, Cooperia and Oesophagostomum attack the intestines, while certain species of the genera Haemonchus and Ostertagia parasitize the stomach, and parasites belonging to the genus Dictyocaulus are found in the lungs. Parasites belonging to the families Filariidae and Setariidae are found in internal tissues and organs, for example, the heart, the blood vessels, the subcutaneous tissues and the lymphatic vessels. The compounds of the invention are active against all of these parasites.

The compounds of the invention are also effective against parasites which infect humans. Typical of the parasites which may most commonly be found in the digestive tracts of human beings are parasites of the genera:

Ancylostoma, Necator, Ascaris, Strongyloides, Trichinella, Capillaria, Trichuris and Enterobius.

The compounds are also active against parasites of the genera Wuchereria, Brugia, Onchocerca and Loa of the family Filariidae (which are found in blood, tissues and organs other than the digestive tract and are medically important), parasites of the genus Dracunculus of the family Dracunculidae and parasites of the genera Strongyloides and Trichinella, which in a particular state may parasitize outside the intestinal tract, although they are essentially intestinal parasites.

The form of the compositions of the invention and the nature of the carriers or diluents employed in them will vary depending upon the intended use of the composition. For example, where the compounds of the invention are to be employed as anthelmintics, they are preferably administered orally, parenterally or topically and the form of composition chosen will be appropriate to the intended route of administration.

For oral administration, the composition of the invention is preferably in the form of a liquid drink comprising a non-toxic solution, suspension or dispersion of the active compound in admixture with a suspending agent (such as bentonite), a wetting agent or other diluents, preferably in water or another non-toxic solvent. The drink, in general, also contains an anti-foaming agent. The active compound would normally be present in the drink in an amount of from 0.01 to 0.5% by weight, more preferably from 0.01 to 0.1% by weight.

Compositions for oral administration may also be in the form of dry solids, preferably in unit dosage form, such as capsules, pills or tablets containing the desired amount of the active compound. These compositions may be prepared by mixing the active compound uniformly with suitable diluents, fillers, disintegrators and/or binding agents, for example starch, lactose, talc, magnesium stearate and vegetable gum. The weight and contents of the preparation will vary widely, depending upon the nature of the animal to be treated, the degree of infection, the nature of the parasite and the body weight of the animal to be treated.

The compounds may also be administered as an additive to animal feedstuffs, in which case they may be dispersed uniformly in the foodstuffs, used as a top dressing or used in the form of pellets. The content of active compound in the foodstuff is preferably from 0.0001 to 0.02%, in order to achieve the desired anthelmintic activity.

For parenteral administration, the compound of the invention is preferably dissolved or suspended in a liquid vehicle, preferably a vegetable oil, such as peanut oil or cottonseed oil. Where the compound is a salt of a compound of formula (I) or formula (I)w, the liquid vehicle may be water or another aqueous medium. Depending upon the animal to be treated, the injection may be subcutaneous or into the proventriculus, a muscle or the trachea. Such preparations would normally contain the active compound at a concentration of from 0.05 to 50% by weight.

The compounds of the invention may also be administered topically in admixture with a suitable carrier, such as dimethyl sulfoxide or a hydrocarbon solvent. Such preparations would be applied directly to the outside of the animal by spraying (e.g. by a hand spray or in spray races), by dipping (e.g. in a plunge dip), by a pour-on solution or by manual methods (e.g. hand-dressing).

The dose of active compound may be varied, depending upon the nature of the animal to be treated, and the nature and degree of parasitic infection. However, best results for oral administration are achieved when the dose is from 0.01 to 100 mg, more preferably from 0.5 to 50 mg, per 1 kg body weight. The compound may be administered in a single dose or in divided doses for a relatively short period, such as from 1 to 5 days.

Where the composition of the invention is intended for agricultural or horticultural use, a variety of forms and formulations is possible. For example, the composition may be formulated as dusts, coarse dusts, soluble powders, microgranules, fine microgranules, wettable powders, dilute emulsions, emulsifiable concentrates, aqueous or oily suspensions, dispersions or solutions (which may be directly sprayable or for dilution), aerosols or capsules in, for example, polymeric substances. The carrier employed may be natural or synthetic and organic or inorganic; it is generally employed to assist the active compound to reach the substrate to be treated, and to make it easier to store, transport or handle the active compound. Solid, liquid and gaseous carriers may be employed, chosen from carriers well known in the art for use with compositions of this type.

Such formulations may be prepared by conventional means, e.g. by intimate mixing and/or grinding of the active ingredient(s) with the carrier or diluent, e.g. solvent, solid carrier or, optionally, surface-active agent.

Suitable solvents include: aromatic hydrocarbons, preferably the $C_8$ to $C_{12}$ fractions from petroleum distillation, such as xylene mixtures or substituted naphthalenes; esters of phthalic acid, such as dibutyl or dioctyl phthalate; aliphatic hydrocarbons, such as cyclohexane or the paraffins; alcohols and glycols or esters thereof, such as ethanol, ethylene glycol, ethylene glycol monomethyl ether or ethylene glycol monoethyl ether; ketones, such as cyclohexanone; strongly polar solvents, such as $\underline{N}$-methyl-2-pyrrolidone, dimethyl sulfoxide or $\underline{N},\underline{N}$-dimethylformamide; optionally epoxidized vegetable oils, such as epoxidized coconut oil or soybean oil; and water.

Solid carriers, which may be used, for example, in dusts and dispersible powders, include natural mineral fillers, such as calcite, talc, kaolin, montmorillonite or attapulgite. In order to improve the physical properties of the composition, it is also possible to add highly dispersed silicic acid or highly dispersed absorbent polymers. Suitable granulated adsorptive carriers may be porous (such as pumice, ground brick, sepiolite or bentonite) or non-porous (such as calcite or sand). A wide variety of pregranulated materials, organic or inorganic, may also be used; examples include dolomite and ground plant residues.

Surface-active agents which may be used are well known in the art and may be non-ionic, cationic or anionic agents having good emulsifying, dispersing and wetting properties. Mixtures of such agents may also be used.

Compositions may also contain stabilizers, anti-foaming agents, viscosity regulators, binders or adhesives or any combination thereof, as well as fertilizers or other active substances to achieve special effects.

Pesticidal compositions will generally contain: from 0.01 to 99%, more preferably from 0.1 to 95%, by weight of the active compound; from 1 to 99.99% of a solid or liquid additive; and from 0 to 25%, more preferably from 0.1 to 25%, of a surface-active agent. Whereas commercial products are generally sold as concentrated compositions, they are generally diluted by the end-user to a concentration of from 0,001 to 0.0001% by weight (from 10 to 1 ppm).

The invention is further illustrated by the following Examples, which illustrate the preparation of the compounds of the present invention, and the subsequent Test Examples, which illustrate the biological activity of the compounds of the invention. In the following Examples, all Nuclear Magnetic Resonance Spectra were measured at 270 MHz, unless otherwise stated.

EXAMPLE 1

13-Cinnamyloxymilbemycin $A_4$

1(a) 13-Cinnamyloxy-5-oxomilbemycin $A_4$ 0.333 g of 13-iodo-5-oxomilbemycin $A_4$ was dissolved in 2.50 ml of 1,2-dichloroethane, and 0.671 g of cinnamyl alcohol and 1.000 g of silver oxide were added to the resulting solution, after which the mixture was stirred at room temperature for 30 minutes. 30 ml of ethyl acetate were added to the reaction mixture, and the insoluble materials were removed by filtration using a Celite (trade mark) filter aid. The filtrate was then washed with a 10% w/v aqueous solution of sodium thiosulfate and with water, in that order, after which it was dried over anhydrous sodium sulfate. The solvent was then removed by evaporation under reduced pressure. The resulting residue was purified by column chromatography through silica gel, eluted with a 3:7 by volume mixture of ethyl acetate and cyclohexane, to afford 0.239 g of the title compound.

1(b) 13-Cinnamyloxymilbemycin $A_4$ 0.119 g of 13-cinnamyloxy-5-oxomilbemycin $A_4$ [prepared as described in step (a) above] was dissolved in 4.2 ml of methanol, and 0.007 g of sodium borohydride was added to the resulting solution, whilst ice-cooling. The mixture was then stirred for 30 minutes, after which 25 ml of ethyl acetate were added the reaction mixture, and the mixture was washed twice with water. It was then dried over anhydrous sodium sulfate and the solvent was removed by evaporation under reduced pressure. The residue was purified by column chromatography through silica gel, eluted with a 3:7 by volume mixture of ethyl acetate and cyclohexane. The isomer substituted at the 15-position was then separated by reverse phase chromatography (through ODS; eluted with 85% v/v aqueous acetonitrile) to afford 0.040 g of the title compound. "ODS" is octadecylsilane.

Mass Spectrum m/z: 672 ($M^+$–2).

Nuclear Magnetic Resonance Spectrum ($CDCl_3$), δ ppm: 1.89 (3H, singlet); 3.37 (1H, doublet, J=9.9 Hz); 4.05 (1H, doublet, J=6.2 Hz); 6.27 (1H, multiplet); 6.57 (1H, doublet, J=14.6 Hz).

EXAMPLE 2

13-Cinnamyloxymilbemycin $A_4$ 5-oxime 0.119 g of 13-cinnamyloxy-5-oxomilbemycin $A_4$ [prepared as described in Example 1(a)] was dissolved in 1.5 ml of methanol, and 0.75 ml of water, 1.5 ml of dioxan and 0.12 g of hydroxylamine hydrochloride were added to the resulting solution, after which the mixture was stirred at 40° C. for 3 hours. 20 ml of ethyl acetate were added to the reaction mixture, and the mixture was washed twice with water, and then dried over anhydrous sodium sulfate. The solvent was then removed by evaporation under reduced pressure. The resulting residue was purified by column chromatography through silica gel, eluted with a 3:7 by volume mixture of ethyl acetate and cyclohexane. The isomer substituted at the 15-position was then separated by reverse phase chromatography (through ODS; eluted with 85% v/v aqueous acetonitrile), to afford 0.04 g of the title compound.

Mass Spectrum m/z: 687 ($M^+$, $C_{41}H_{53}NO_8$).

Nuclear Magnetic Resonance Spectrum ($CDCl_3$), δ ppm: 1.94 (3H, singlet); 3.36 (1H, doublet, J=9.5 Hz); 4.67 (1H, singlet); 6.28 (1H, multiplet); 6.56 (1H, doublet, J=15.8 Hz).

EXAMPLE 3

13-[3-(3-Aminophenyl)propoxy]milbemycin $A_4$

3(a) 13-[3-(3-Nitrophenyl)propionyloxy]-5-oxomilbemycin $A_4$ 0.33 g of 13-iodo-5-oxomilbemycin $A_4$ was dissolved in 2.0 ml of 1,2-dichloroethane, and 0.45 g of 3-(3-nitrophenyl) propanol and 0.34 g of mercuric iodide were added to the resulting solution, after which the mixture was stirred at room temperature for 5 hours. At the end of this time, 10 ml of ethyl acetate were added to the reaction mixture, and insolubles were removed by filtration. The filtrate was washed with a 20% w/v aqueous solution of potassium iodide (twice), with a 10% w/v aqueous solution of sodium thiosulfate and with water, in that order, after which it was dried over anhydrous sodium sulfate. The solvent was then removed by evaporation under reduced pressure. The resulting residue was purified by column chromatography through silica gel, eluted with a 25:75 by volume mixture of ethyl acetate and hexane, to afford 0.29 g of the title compound.

3(b) 13-[3-(3-Nitrophenyl)propoxy]milbemycin $A_4$ 0.29 g of 13-[3-(3-nitrophenyl)propionyloxy]-5-oxomilbemycin $A_4$ [prepared as described in step (a) above] was dissolved in 2 ml of methanol, and 0.015 g of sodium borohydride was added to the resulting solution, whilst ice-cooling, after which the mixture was stirred for 20 minutes. At the end of this time, 10 ml of ethyl acetate were added to the reaction mixture, and the mixture was washed twice with water and then dried over anhydrous sodium sulfate. The solvent was then removed by evaporation under reduced pressure. The residue was purified by column chromatography through silica gel, eluted with a 1:1 by volume mixture of ethyl acetate and hexane to afford 0.27 g of the title compound.

3(c) 13-[3-(3-Aminophenyl)propoxy]milbemycin $A_4$ 0.27 g of 13-[3-(3-nitrophenyl)propoxy]milbemycin $A_4$ [prepared as described in step (b) above] was dissolved in 5 ml of 90% v/v aqueous acetic acid, and 0.12 g of zinc powder was added to the resulting solution, whilst ice-cooling, after which the mixture was stirred for 20 minutes. At the end of this time, 20 ml of ethyl acetate were added to the reaction mixture, and insolubles were removed by filtration. The filtrate was washed with water three times and then dried over anhydrous sodium sulfate. The solvent was then removed by evaporation under reduced pressure. The resulting residue was purified by column chromatography (through ODS; eluted with 75% v/v aqueous acetonitrile), to afford 0.17 g of the title compound.

Nuclear Magnetic Resonance Spectrum ($CDCl_3$), δ ppm: 1.87 (3H, singlet); 3.20 (1H, doublet, J=9.8 Hz); 3.96 (1H, doublet, J=6.3 Hz).

EXAMPLES 4 TO 11

The compounds of Examples 4 to 11 were prepared using the same procedures as described in Example 3.

EXAMPLE 4

13-[3-(2-Aminophenyl]propoxy]milbemycin $A_4$

Nuclear Magnetic Resonance Spectrum ($CDCl_3$), δ ppm: 1.87 (3H, singlet); 3.25 (1H, doublet, J=10.3 Hz); 3.96 (1H, doublet, J=6.3 Hz).

EXAMPLE 5

13-4-Aminophenyl)propoxy]milbemycin $A_4$

Nuclear Magnetic Resonance Spectrum ($CDCl_3$), δ ppm: 1.87 (3H, singlet); 3.19 (1H, doublet, J=9.7 Hz); 3.96 (1H, doublet, J=6.3 Hz).

EXAMPLE 6

13-[3-(4-Aminophenyl)cinnamyloxy]milbemycin $A_4$

Nuclear Magnetic Resonance Spectrum ($CDCl_3$), δ ppm:
1.87 (3H, singlet); 3.34 (1H, doublet, J=10.2 Hz); 3.95 (1H, doublet, J=6.3 Hz); 6.06 (1H, doublet of triplets, J=15.6 and 5.9 Hz); 6.45 (1H, doublet, J=15.6 Hz).

EXAMPLE 7

13-(3-Aminocinnamyloxy)milbemycin $A_4$

Nuclear Magnetic Resonance Spectrum ($CDCl_3$), δ ppm:
1.87 (3H, singlet); 3.34 (1H, doublet, J=9.8 Hz); 3.96 (1H, doublet, J=6.3 Hz); 6.19 (1H, doublet of triplets, J=16.1 and 5.9 Hz); 6.47 (1H, doublet, J=16.1 Hz).

EXAMPLE 8

13-(2-Aminocinnamyloxy)milbemycin $A_4$

Nuclear Magnetic Resonance Spectrum ($CDCl_3$), δ ppm:
1.87 (3H, singlet); 3.36 (1H, doublet, J=9.7 Hz); 3.96 (1H, doublet, J=5.9 Hz); 6.13 (1H, doublet of triplets, J=16.1 and 5.4 Hz); 6.61 (1H, doublet, J=16.1 Hz).

EXAMPLE 9

13-[3-(3-Aminophenyl)-2-methylprop-2(E)-enyloxy] milbemycin $A_4$

Nuclear Magnetic Resonance Spectrum ($CDCl_3$), δ ppm:
1.88 (3H, singlet); 1.88 (3H, singlet); 3.34 (1H, doublet, J=9.7 Hz); 3.96 (1H, doublet, J=6.3 Hz); 6.36 (1H, multiplet).

EXAMPLE 10

13-[3-(3-Aminophenyl)-3-methylprop-2(E)-enyloxy]-milbemycin $A_4$

Nuclear Magnetic Resonance Spectrum ($CDCl_3$), δ ppm:
1.87 (3H, singlet); 1.99 (3H, singlet); 3.33 (1H, doublet, J=9.8 Hz); 3.96 (1H, doublet, J=5.9 Hz); 5.86 (1H, multiplet).

EXAMPLE 11

13-[3-(3-Aminophenyl)-3-methylprop-2(Z)-enyloxy] milbemycin $A_4$

Nuclear Magnetic Resonance Spectrum ($CDCl_3$), δ ppm:
1.87 (3H, singlet); 2.05 (3H, singlet); 3.16 (1H, doublet, J=10.3 Hz); 3.95 (1H, doublet, J=6.4 Hz); 5.60 (1H, multiplet).

EXAMPLE 12

13-[3-(4-Acetamidophenyl)propoxy]milbemycin $A_4$ 0.035 g of 13-[3-(4-aminophenyl)propoxy]milbemycin $A_4$ (prepared as described in Example 5) was dissolved in 2.0 ml of methylene chloride, and 0.005 g of pyridine and 0.006 g of acetic anhydride were added to the resulting solution, after which the mixture was stirred at room temperature for 12 hours. At the end of this time, 10 ml of ethyl acetate were added to the reaction mixture, and the resulting mixture was washed with 0.1N aqueous hydrochloric acid, with water, with a 4% w/v aqueous solution of sodium hydrogencarbonate and with water, in that order, after which it was dried over anhydrous sodium sulfate. The solvent was then removed by evaporation under reduced pressure. The resulting residue was purified by column chromatography (through ODS; eluted with 80% v/v aqueous acetonitrile), to afford 0.035 g of the title compound.

Nuclear Magnetic Resonance Spectrum ($CDCl_3$), δ ppm:
1.87 (3H, singlet); 2.17 (3H, singlet); 3.19 (1H, doublet, J=9.7 Hz); 3.96 (1H, doublet, J=6.3 Hz).

EXAMPLES 13 TO 15

The compounds of Examples 13 to 15 were prepared by treating the amines prepared as described in Examples 6 to 8, respectively, by the same procedures as described in Example 12.

EXAMPLE 13

13-(4-Acetamidocinnamyloxy)milbemycin $A_4$

Nuclear Magnetic Resonance Spectrum ($CDCl_3$), δ ppm:
1.88 (3H, singlet); 2.18 (3H, singlet); 3.34 (1H, doublet, J=9.7 Hz); 3.96 (1H, doublet, J=5.9 Hz); 6.19 (1H, doublet of triplets, J=16.1 and 5.9 Hz); 6.52 (1H, doublet, J=16.1 Hz).

EXAMPLE 14

13-(3-Acetamidocinnamyloxy)milbemycin $A_4$

Nuclear Magnetic Resonance Spectrum ($CDCl_3$), δ ppm:
1.87 (3H, singlet); 2.18 (3H, singlet); 3.34 (1H, doublet, J=9.7 Hz); 3.96 (1H, doublet, J=6.3 Hz); 6.26 (1H, doublet of triplets, J=16.1 and 5.9 Hz); 6.53 (1H, doublet, J=16.1 Hz).

EXAMPLE 15

13-(2-Acetamidocinnamyloxy)milbemycin $A_4$

Nuclear Magnetic Resonance Spectrum ($CDCl_3$), δ ppm:
1.88 (3H, singlet); 2.20 (3H, singlet); 3.37 (1H, doublet, J=9.7 Hz); 3.96 (1H, doublet, J=6.3 Hz); 6.17 (1H, doublet of triplets, J=15.6 and 5.4 Hz); 6.66 (1H, doublet, J=15.6 Hz).

EXAMPLE 16

13-{3-[3-(3-Methylureido)phenyl]propoxy}milbemycin $A_4$ 0.069 g of 13-[3-(3-aminophenyl )propoxy]milbemycin $A_4$ (prepared as described in Example 3) was dissolved in 2.0 ml of tetrahydrofuran, and 0.009 g of methyl isocyanate was added to the resulting solution, after which the mixture was stirred for 4 days. At the end of this time, the reaction mixture was diluted with 20 ml of ethyl acetate, washed with water, and dried over anhydrous sodium sulfate. The solvent was then removed by evaporation under reduced pressure. The resulting residue was purified by column chromatography (through ODS; eluted with 80% v/v aqueous acetonitrile), to afford 0.051 g of the title compound.

Nuclear Magnetic Resonance Spectrum ($CDCl_3$), δ ppm:
1.87 (3H, singlet); 2.84 (3H, singlet); 3.20 (1H, doublet, J=10.3 Hz); 3.96 (1H, doublet, J=6.3 Hz).

EXAMPLES 17 TO 20

The compounds of Examples 17 to 20 were prepared by the same procedures as described in Example 16 above.

EXAMPLE 17

13-{3-[2-(3-Methylureido)phenyl]propoxy}milbemycin $A_4$

Nuclear Magnetic Resonance Spectrum ($CDCl_3$), δ ppm:
1.88 (3H, singlet); 2.82 (3H, singlet); 3.25 (1H, doublet, J=9.7 Hz); 3.97 (1H, doublet, J=6.3 Hz).

EXAMPLE 18

13-[3-(3-Methylureido)cinnamyloxy]milbemycin $A_4$

Nuclear Magnetic Resonance Spectrum (CDCl$_3$), δ ppm: 1.88 (3H, singlet); 3.34 (1H, doublet, J=9.8 Hz); 3.96 (1H, doublet, J=6.4 Hz); 6.26 (1H, doublet of triplets, J=15.6 and 5.4 Hz); 6.54 (1H, doublet, J=15.6 Hz).

EXAMPLE 19

13-[3-(3-Phenylureido)cinnamyloxy]milbemycin $A_4$

Mass Spectrum m/z: 689 (M$^+$–119).

Nuclear Magnetic Resonance Spectrum (CDCl$_3$), δ ppm: 1.87 (3H, singlet); 3.33 (1H, doublet, J=9.8 Hz); 3.96 (1H, doublet, J=6.4 Hz); 6.25 (1H, doublet of triplets, J=15.6 and 5.9 Hz); 6.53 (1H, doublet, J=15.6 Hz).

EXAMPLE 20

13-[3-(3-Methylthioureido)cinnamyloxy]milbemycin $A_4$

Nuclear Magnetic Resonance Spectrum (CDCl$_3$), δ ppm: 1.88 (3H, singlet); 3.15 (3H, singlet); 3.34 (1H, doublet, J=9.8 Hz); 3.96 (1H, doublet, J=6.2 Hz); 6.00 (1H, broad singlet); 6.29 (1H, doublet of triplets, J=16.1 and 5.4 Hz); 6.56 (1H, doublet, J=16.1Hz).

EXAMPLE 21

13-(3-Ethoxycarbonylaminocinnamyloxy)milbemycin $A_4$ 0.120 g of 13-(3-aminocinnamyloxy)milbemycin $A_4$ (prepared as described in Example 7) was dissolved in 1.0 ml of methylene chloride, and 0.014 ml of pyridine and 0.016 ml of ethyl chloroformate were added to the resulting solution, after which the mixture was stirred at room temperature for 25 minutes. At the end of this time, 10 ml of ethyl acetate was added to the reaction mixture, and the resulting mixture was washed with 0.1N aqueous hydrochloric acid, with water, with a 4% w/v aqueous solution of sodium hydrogencarbonate and with water, in that order, after which it was dried over anhydrous sodium sulfate. The solvent was then removed by evaporation under reduced pressure. The resulting residue was purified by column chromatography (through ODS; eluted with 80% v/v aqueous acetonitrile), to afford 0.035 g of the title compound.

Nuclear Magnetic Resonance Spectrum (CDCl$_3$), δ ppm: 1.87 (3H, singlet); 3.34 (1H, doublet, J=9.8 Hz); 3.96 (1H, doublet, J=6.8 Hz); 4.23 (2H, singlet); 6.26 (1H, doublet of triplets, J=16.1 and 5.4 Hz); 6.26 (1H, doublet, J=16.1 Hz).

EXAMPLES 22 TO 26

The compounds of Examples 22 to 26 were prepared by the same procedures as described in Example 21, above.

EXAMPLE 22

13-(3-Cyanoacetamidocinnamyloxy)milbemycin $A_4$

Nuclear Magnetic Resonance Spectrum (CDCl$_3$), δ ppm: 1.87 (3H, singlet); 3.34 (1H, doublet, J=9.8 Hz); 3.56 (2H, singlet); 3.96 (1H, doublet, J=5.9 Hz); 6.28 (1H, doublet of triplets, J=16.1 and 5.9 Hz); 6.56 (1H, doublet, J=16.1 Hz).

EXAMPLE 23

13-(3-Methoxalylaminocinnamyloxy)milbemycin $A_4$

Nuclear Magnetic Resonance Spectra (CDCl$_3$), δ ppm: 1.88 (3H, singlet); 3.35 (1H, doublet, J=9.8 Hz); 3.97 (1H, doublet, J=7.8 Hz); 3.98 (2H, singlet); 6.29 (1H, doublet of triplets, J=15.6 and 5.9 Hz); 6.57 (1H, doublet, J=15.6 Hz).

EXAMPLE 24

13-[3-(4-Cyanobenzoylamino)cinnamyloxy]milbemycin $A_4$

Nuclear Magnetic Resonance Spectrum (CDCl$_3$), δ ppm: 1.87 (3H, singlet); 3.35 (1H, doublet, J=9.8 Hz); 3.96 (1H, doublet, J=5.9 Hz); 6.28 (1H, doublet of triplets, J=16.1 and 5.9 Hz); 6.58 (1H, doublet, J=16.1 Hz).

EXAMPLE 25

13-(3-Methanesulfonylaminocinnamyloxy)milbemycin $A_4$

Nuclear Magnetic Resonance Spectrum (CDCl$_3$), δ ppm: 1.88 (3H, singlet); 3.01 (3H, singlet); 3.34 (1H, doublet, J=9.8 Hz); 3.96 (1H, doublet, J=6.4 Hz); 6.29 (1H, doublet of triplets, J=15.6 and 5.9 Hz); 6.56 (1H, doublet, J=15.6 Hz).

EXAMPLE 26

13-[3-N-(Methanesulfonyl)methylaminocinnamyloxy] milbemycin $A_4$

Nuclear Magnetic Resonance Spectrum (CDCl$_3$), δ ppm: 1.88 (3H, singlet); 2.85 (3H, singlet); 3.33 (3H, singlet); 3.96 (1H, doublet, J=6.4 Hz); 6.29 (1H, doublet of triplets, J=16.1 and 5.9 Hz); 6.57 (1H, doublet, J=16.1 Hz).

EXAMPLE 27

13-(3-Methylaminocinnamyloxy)milbemycin $A_4$ 250 mg of 13-(3-aminocinnamyloxy)milbemycin $A_4$ (obtained by substantially the same method as that described in Example 7) were dissolved in 0.5 ml of methanol. 15.0 mg of paraformaldehyde and 28.5 mg of sodium cyanoborohydride were then added to the resulting solution, and then the mixture was stirred at room temperature for 8 hours. At the end of this time, the reaction mixture was dissolved in 30 ml of ethyl acetate and washed with water, with a 4% w/v aqueous solution of sodium hydrogencarbonate and with water, in that order. The solution was then dried over anhydrous sodium sulfate, after which it was evaporated to dryness. The residue was purified by reverse phase chromatography (through ODS; 90% v/v aqueous acetonitrile), to afford 80 mg of the title compound.

Mass Spectrum m/z: 703 (M$^+$, $C_{42}H_{57}NO_8$).

Nuclear Magnetic Resonance Spectrum (CDCl$_3$), δ ppm: 1.87 (3H, singlet); 2.84 (3H, singlet); 3.25 (1H, doublet, J=9.8 Hz); 3.96 (1H, doublet, J=5.9 Hz); 6.15–6.27 (1H, multiplet); 6.75 (1H, doublet, J=7.8 Hz).

EXAMPLE 28

13-[3-(3,3-Dimethylcarbazoylamino)cinnamyloxy] milbemycin $A_4$ 119 mg of 13-(3-aminocinnamyloxy)milbemycin $A_4$ (obtained by substantially the same method as that described in Example 7) were dissolved in 0.9 ml of methylene chloride. 44.4 mg of 2-chloroformyl-1,2,4-triazolo[4.3-a] pyridin-2-one and 0.019 ml of pyridine were then added to the resulting solution, and then the mixture was stirred at room temperature for 1 hour. At the end of this time, 0.010 ml of 1,1-dimethylhydrazine was added, and then the whole mixture was stirred at room temperature for a further 1 hour. The reaction mixture was allowed to stand overnight at room temperature, after which it was diluted with 30 ml of ethyl acetate. The solution was then washed with water, with a 4% w/v aqueous solution of sodium hydrogen-carbonate, and with water, in that order. The solution was then dried over anhydrous sodium sulfate, after which it was evaporated to dryness. The residue was purified by reverse phase chromatography (through ODS; 80% v/v aqueous acetonitrile), to afford 80 mg of the title compound.

Mass Spectrum m/z: 689 (M$^+$–86).

Nuclear Magnetic Resonance Spectrum (CDCl$_3$), δ ppm: 1.87 (3H, singlet); 2.62 (6H, singlet); 3.34 (1H, doublet, J=9.8 Hz); 3.96 (1H, doublet, J=6.4 Hz).

EXAMPLE 29

13-(2-Phenylcyclopropylmethoxy)milbemycin A$_4$

The procedure described in Example 3(a) was repeated, except that 2-phenylcyclopropylmethanol was used in place of 3-(3-nitrophenyl)propanol, and then the reaction product was worked up following the method described in Example 3(b), to give the title compound.

Mass Spectrum m/z: 688 (M$^+$, C$_{42}$H$_{56}$O$_8$).

Nuclear Magnetic Resonance Spectrum (CDCl$_3$), δ ppm: 1.87 (3H, singlet); 3.10–3.45 (2H, multiplet); 3.25 (1H, doublet, J=6.8 Hz); 3.95 (1H, doublet, J=6.4 Hz).

EXAMPLE 30

13-Phenethyloxymilbemycin A$_4$

Step A 0.333 g of 13-iodo-5-oxomilbemycin A$_4$ (III) (prepared as described in Preparation 1) was dissolved in 2.50 ml of 1,2-dichloroethane, and then 0.610 g of β-phenethyl alcohol and 1.000 g of silver oxide were added to the resulting solution. The mixture was then stirred at room temperature for 30 minutes. At the end of this time, 30 ml of ethyl acetate were added to the reaction mixture, insoluble materials were removed by filtration using a Celite (trade mark) filter aid. The filtrate was then washed with a 10% aqueous solution of sodium thiosulfate and with water, in that order, after which it was dried over anhydrous sodium sulfate, and the solvent was removed by distillation to dryness under reduced pressure. The residue was purified by column chromatography through silica gel, eluted with a 3:7 by volume mixture of ethyl acetate and cyclohexane, to afford 0.282 g of 5-oxo-13-phenethyloxymilbemycin A$_4$.

Step B 0.140 g of 5-oxo-13-phenethyloxymilbemycin A$_4$ (prepared as described in Step A) was dissolved in 6 ml of methanol, and 0.009 g of sodium borohydride was added to the resulting solution, whilst ice-cooling, and the mixture was stirred for 30 minutes. At the end of this time, 30 ml of ethyl acetate were added to the reaction mixture, and the mixture was washed twice with water and dried over anhydrous sodium sulfate. The solvent was then removed by distillation to dryness under reduced pressure. The residue was purified by column chromatography through silica gel, eluted with a 3:7 by volume mixture of ethyl acetate and cyclohexane. The isomer substituted at the 15-position was then separated by reverse phase chromatography (ODS:eluted with 85% v/v aqueous acetonitrile) to obtain 0.076 g of the title compound. "ODS" is octadecylsilane.

Mass Spectrum m/e: 662 (M$^+$, C$_{40}$H$_{54}$O$_8$).

Nuclear Magnetic Resonance Spectrum (CDCl$_3$) δ ppm: 1.87 (3H, singlet); 3.22 (1H, doublet, J=10.0 Hz); 3.95 (1H, doublet, J=6.2 Hz).

EXAMPLE 31

13-Phenethyloxymilbemycin A$_4$ 5-oxime 0.85 ml of water, 1.7 ml of dioxane and 0.150 g of hydroxylamine hydrochloride were added to a solution of 0.140 g of 5-oxo-13-phenethyloxymilbemycin A$_4$ (prepared as described in Step A of Example 1) in 1.7 ml of methanol. The mixture was then stirred at 35° C. for 3 hours. At the end of this time, the reaction mixture was diluted with 20 ml of ethyl acetate, wasted twice with water and dried over anhydrous sodium sulfate. The solvent was then removed by distillation to dryness under reduced pressure. The residue was purified by column chromatography through silica gel, eluted with a 3:7 by volume mixture of ethyl acetate and cyclohexane. The isomer substituted at the 15-position was then separated by reverse phase chromatography (ODS: eluted with 85% v/v aqueous acetonitrile) to obtain 0.080 g of the title compound.

Mass Spectrum m/e: 675 (M$^+$, C$_{40}$H$_{53}$NO$_8$).

Nuclear Magnetic Resonance Spectrum (CDCl$_3$) δ ppm: 1.94 (3H, singlet); 3.22 (1H, doublet, J=9.9 Hz); 4.66 (1H, singlet).

EXAMPLE 32

13-[2-(4-nitrophenyl)ethoxy]milbemycin-A$_4$

Step A 1.250 g of 4-nitrophenethyl alcohol, 0.300 g of anhydrous calcium carbonate and 0.815 g of mercuric iodide were added to a solution of 1.000 g of 13-iodo-5-oxomilbemcin A$_4$ (III) (prepared as described in Preparation 1) in 6.0 ml of 1,2-dichloroethane, and the mixture was stirred at room temperature for 2 hours. At the end of this time, 30 ml of ethyl acetate were added to the reaction mixture, insoluble materials were removed by filtration, and the filtrate was washed with a 20% w/v aqueous solution of potassium iodide (twice), with a 10% w/v aqueous solution of sodium thiosulfate and with water, in that order, after which it was dried over anhydrous sodium sulfate. The solvent was then removed by distillation to dryness under reduced pressure. The residue was purified by column chromatography through silica gel, eluted with a 15:85 by volume mixture of ethyl acetate and cyclohexane, to afford 0.744 g of 5-oxo-13-[2-(4-nitrophenyl)ethoxy]milbemycin A$_4$.

Step B 0.037 g of sodium borohydride was added to a solution of 0.710 g of 5-oxo-13-[2-(4-nitrophenyl)ethoxy]milbemycin A$_4$ (prepared as described in the preceding Step A) in 27 ml of methanol, whilst ice-cooling, and the mixture was stirred for 20 minutes. At the end of this time, 100 ml of ethyl acetate were added to the reaction mixture, the mixture was washed twice with water and dried over anhydrous sodium sulfate. The solvent was then removed by distillation to dryness under reduced pressure. The residue was purified by column chromatography through silica gel, eluted with a 2:8 by volume mixture of ethyl acetate and cyclohexane, to afford 0.693 g of the title compound.

Mass Spectrum m/e: 707 (M$^+$, C$_{40}$H$_{53}$NO$_{10}$).

Nuclear Magnetic Resonance Spectrum (CDCl$_3$) δ ppm: 1.87 (3H, singlet); 3.24 (1H, doublet, J=9.5 Hz); 3.95 (1H, doublet, J=6.2 Hz).

The compounds of Examples 33 to 50 were prepared by the same method as described in Example 32.

EXAMPLE 33

13-(1-Methyl-2-phenylethoxy)milbemycin A$_4$

Mass Spectrum (m/e) 676 (M$^+$, C$_{41}$H$_{56}$O$_8$).

Nuclear Magnetic Resonance Spectrum (CDCl$_3$) δ ppm: 1.87 (3H, singlet); 3.27 (0.5H, doublet, J=10.0 Hz); 3.33 (0.5H, doublet, J=9.9 Hz); 3.955 (0.5H, doublet, J=6.2 Hz); 3.950 (0.5H, doublet, J=6.2 Hz).

EXAMPLE 34

13-[2-(4-Chlorophenyl)ethoxy]milbemycin $A_4$

Mass Spectrum (m/e): 696 ($M^+$, $C_{40}H_{53}ClO_8$).

Nuclear Magnetic Resonance Spectrum ($CDCl_3$) δ ppm: 1.83 (3H, singlet); 3.19 (1H, doublet, J=9.9 Hz); 4.00 (1H, doublet, J=6.9 Hz).

EXAMPLE 35

13-[2-(4-Methoxyphenyl)ethoxy]milbemycin $A_4$

Mass Spectrum (m/e): 692 ($M^+$, $C_{41}H_{56}O_9$).

Nuclear Magnetic Resonance Spectrum ($CDCl_3$) δ ppm: 1.87 (3H, singlet); 3.21 (1H, doublet, J=9.9 Hz); 3.96 (1H, doublet, J=6.2 Hz).

EXAMPLE 36

13-(2-Phenylpropoxy)milbemycin $A_4$

Mass Spectrum (m/e): 676 ($M^+$, $C_{41}H_{56}O_8$).

Nuclear Magnetic Resonance Spectrum ($CDCl_3$) δ ppm: 1.83 (3H, singlet); 3.20 (1H, doublet, J=9.9 Hz); 3.95 (1H, doublet, J=6.2 Hz).

EXAMPLE 37

13-(2-Methoxy-2-phenylethoxy)milbemycin $A_4$

Mass Spectrum (m/e): 692 ($M^+$, $C_{41}H_{56}O_9$).

Nuclear Magnetic Resonance Spectrum ($CDCl_3$) δ ppm: 1.87 (3H, singlet); 3.28 (3H, singlet); 3.31 (1H, doublet, J=9.9 Hz); 3.96 (1H, doublet, J=6.2 Hz).

EXAMPLE 38

13-[2-(3,4-Dimethoxyphenyl)ethoxy]milbemycin $A_4$

Mass Spectrum (m/e): 722 ($M^+$, $C_{42}H_{58}O_{10}$).

Nuclear Magnetic Resonance Spectrum ($CDCl_3$) δ ppm: 1.87 (3H, singlet); 3.22 (1H, doublet, J=9.5 Hz); 3.22 (3H, singlet); 3.88 (3H, singlet); 3.95 (1H, doublet, J=6.2 Hz).

EXAMPLE 39

13-[2-(4-Methoxy-3-nitrophenyl)ethoxy]milbemycin $A_4$

Mass Spectrum (m/e): 737 ($M^+$, $C_{41}H_{55}NO_{10}$).

Nuclear Magnetic Resonance Spectrum ($CDCl_3$) δ ppm: 1.87 (3H, singlet); 3.19 (1H, doublet, J=9.9 Hz); 3.95 (1H, doublet, J=6.2 Hz); 3.94 (3H, singlet).

EXAMPLE 40

13-[2-(3-Methoxy-4-nitrophenyl)ethoxy]milbemycin $A_4$

Mass Spectrum (m/e): 737 ($M^+$, $C_{41}H_{55}NO_{10}$).

Nuclear Magnetic Resonance Spectrum ($CDCl_3$) δ ppm: 1.88 (3H, singlet); 3.20 (1H, doublet, J=9.9 Hz); 3.95 (3H, singlet).

EXAMPLE 41

13-[2-(2,4-Dimethylphenyl)ethoxy]milbemycin $A_4$

Mass Spectrum (m/e): 690 ($M^+$, $C_{42}H_{58}O_8$).

Nuclear Magnetic Resonance Spectrum ($CDCl_3$) δ ppm: 1.88 (3H, singlet); 3.95 (1H, doublet, J=6.2 Hz).

EXAMPLE 42

13-[2-(4-Fluorophenyl)ethoxy]milbemycin $A_4$

Mass Spectrum (m/e): 680 ($M^+$, $C_{40}H_{53}FO_8$).

Nuclear Magnetic Resonance Spectrum ($CDCl_3$) δ ppm: 1.87 (3H, singlet); 3.19 (1H, doublet, J=9.9 Hz); 3.95 (1H, doublet, J=6.2 Hz).

EXAMPLE 43

13-[2-(3,4-Dichlorophenyl)ethoxy]milbemycin $A_4$

Mass Spectrum (m/e): 731 ($M^+$, $C_{40}H_{52}Cl_2O_8$).

Nuclear Magnetic Resonance Spectrum ($CDCl_3$) δ ppm: 1.87 (3H, singlet); 3.19 (1H, doublet, J=9.9 Hz); 3.95 (1H, doublet, J=6.2 Hz).

EXAMPLE 44

13-[2-(2,5-Dimethoxyphenyl)ethoxy]milbemycin $A_4$

Mass Spectrum (m/e): 722 ($M^+$, $C_{40}H_{58}O_{10}$).

Nuclear Magnetic Resonance Spectrum ($CDCl_3$) δ ppm: 1.87 (3H, singlet); 3.24 (1H, doublet, J=9.5 Hz); 3.95 (1H, doublet, J=6.2 Hz).

EXAMPLE 45

13-[2-(4-Ethoxy-3-methoxyphenyl)ethoxy]milbemycin $A_4$

Mass Spectrum (m/e): 736 ($M^+$, $C_{43}H_{60}O_{10}$).

Nuclear Magnetic Resonance Spectrum ($CDCl_3$) δ ppm: 1.87 (3H, singlet); 3.22 (1H, doublet, J=9.9 Hz); 3.96 (1H, doublet, J=6.2 Hz).

EXAMPLE 46

13-[2-(2,6-Difluorophenyl)ethoxy]milbemycin $A_4$

Mass Spectrum (m/e): 698 ($M^+$, $C_{40}H_{52}F_2O_8$).

Nuclear Magnetic Resonance Spectrum ($CDCl_3$) δ ppm: 1.87 (3H, singlet); 3.21 (1H, doublet, J=9.5 Hz); 3.95 (1H, doublet, J=6.2 Hz).

EXAMPLE 47

13-[2-(2-Nitrophenyl)ethoxy]milbemycin $A_4$

Mass Spectrum (m/e): 707 ($M^+$, $C_{40}H_{53}NO_{10}$).

Nuclear Magnetic Resonance Spectrum ($CDCl_3$) δ ppm: 1.87 (3H, singlet); 3.96 (1H, doublet, J=6.2 Hz).

EXAMPLE 48

13-[2-(3-Nitrophenyl)ethoxy]milbemycin $A_4$

Mass Spectrum (m/e): 707 ($M^+$, $C_{40}H_{53}NO_{10}$).

Nuclear Magnetic Resonance Spectrum ($CDCl_3$) δ ppm: 1.87 (3H, singlet); 3.20 (1H, doublet, J=9.9 Hz); 3.95 (1H, doublet, J=6.2 Hz).

EXAMPLE 49

13-[2-(3-Methoxy-4-methoxymethoxyphenyl)ethoxy]milbemycin $A_4$

Mass Spectrum (m/e): 752 ($M^+$, $C_{43}H_{60}O_{11}$).

Nuclear Magnetic Resonance Spectrum ($CDCl_3$) δ ppm: 1.87 (3H, singlet); 3.21 (1H, doublet, J=9.9 Hz); 3.95 (1H, doublet, J=6.2 Hz).

EXAMPLE 50

13-[2-(3,4-Dimethoxyphenyl)propoxy]milbemycin $A_4$

Mass Spectrum (m/e): 736 ($M^+$, $C_{43}H_{60}O_{10}$).

Nuclear Magnetic Resonance Spectrum ($CDCl_3$) δ ppm: 1.87 (3H, singlet); 3.87 (3H, singlet); 3.88 (3H, single:); 3.97 (1H, doublet, J=6.2 Hz).

EXAMPLE 51

13-[2-(4-Nitrophenyl)ethoxy]milbemycin $A_4$ 5-oxime 0.6 ml of water, 1.2 ml of dioxane and 0.110 g of hydroxylamine hydrochloride were added to a solution of 0.106 g of 5-oxo-13-[2-(4-nitrophenyl)ethoxy]milbemycin $A_4$ (prepared as described in Step A of Example 3) in 1.2 ml of methanol, and the mixture was stirred at 40° C. for 2.5 hours. At the end of this time, 20 ml of ethyl acetate were added to the reaction mixture, and the mixture was washed twice with water. It was then dried over anhydrous sodium sulfate, and the solvent was removed by distillation to dryness under reduced pressure. The residue was purified by column chromatography through silica gel, eluted with a 2:8 by volume mixture of ethyl acetate and cyclohexane, to afford 0.090 g of the title compound.

Mass Spectrum m/e: 720 ($M^+$, $C_{40}H_{52}N_2O_{10}$).

Nuclear Magnetic Resonance Spectrum ($CDCl_3$) δ ppm: 1.94 (3H, singlet); 3.20 (1H, doublet, J=9.9 Hz); 4.66 (1H, singlet).

The compounds of Examples 52–53 were prepared by a similar procedure to that described in Step A of Example 3 and in Example 51.

EXAMPLE 52

13-(1-Methyl-2-phenylethoxy)milbemycin $A_4$ oxime

Mass Spectrum (m/e) 689 ($M^+$, $C_{41}H_{55}NO_8$).

Nuclear Magnetic Resonance Spectrum ($CDCl_3$) δ ppm: 1.94 (3H, singlet); 3.28 (0.5H, doublet, J=10.3 Hz); 3.34 (0.5H, doublet, J=9.9 Hz); 4.65 (0.5H, singlet); 4.66 (0.5H, singlet).

EXAMPLE 53

13-[2-(4-Chlorophenyl)ethoxy]milbemycin $A_4$ oxime

Mass Spectrum (m/e): 709 ($M^+$, $C_{41}H_{52}ClNO_8$).

Nuclear Magnetic Resonance Spectrum ($CDCl_3$) δ ppm: 1.94 (3H, singlet); 3.20 (1H, doublet, J=9.9 Hz); 4.66 (1H, singlet).

EXAMPLE 54

13-(2-Phenylpropoxy)milbemycin $A_4$ oxime

Mass Spectrum (m/e): 689 ($M^+$, $C_{41}H_{55}NO_8$).

Nuclear Magnetic Resonance Spectrum ($CDCl_3$) δ ppm: 1.93 (3H, singlet); 3.20 (1H, doublet, J=10.2 Hz); 4.66 (1H, singlet).

EXAMPLE 55

13-[2-(3,4-Dimethoxyphenyl)propoxy]milbemycin $A_4$ oxime

Mass Spectrum (m/e): 749 ($M^+$, $C_{43}H_{59}NO_{10}$).

Nuclear Magnetic Resonance Spectrum ($CDCl_3$) δ ppm: 1.94 (3H, singlet); 3.16 (1H, doublet, J=9.9 Hz); 4.66 (1H, singlet).

EXAMPLE 56

13-(4-Methoxyphenethyloxy)milbemycin $A_4$ oxime

Mass Spectrum (m/e): 705 ($M^+$, $C_{41}H_{55}NO_9$).

Nuclear Magnetic Resonance Spectrum ($CDCl_3$) δ ppm: 1.94 (3H, singlet); 3.21 (1H, doublet, J=9.9 Hz); 4.66 (1H, singlet).

EXAMPLE 57

13-(4-Fluorophenethyloxy)milbemycin $A_4$ oxime

Mass Spectrum (m/e): 693 ($M^+$, $C_{40}H_{52}FNO_8$).

Nuclear Magnetic Resonance Spectrum ($CDCl_3$) δ ppm: 1.94 (3H, singlet); 3.19 (1H, doublet, J=9.9 Hz); 4.66 (1H, singlet).

EXAMPLE 58

13-(3,4-Dichlorophenethyloxy)milbemycin $A_4$ oxime

Mass Spectrum (m/e): 743 ($M^+$, $C_{40}H_{52}Cl_2NO_8$).

Nuclear Magnetic Resonance Spectrum ($CDCl_3$) δ ppm: 1.94 (3H, singlet); 3.19 (1H, doublet, J=9.5 Hz); 4.66 (1H, singlet).

EXAMPLE 59

13-(2,5-Dimethoxyphenethyloxy)milbemycin $A_4$ oxime

Mass Spectrum (m/e): 735 ($M^+$, $C_{42}H_{57}NO_{10}$).

Nuclear Magnetic Resonance Spectrum ($CDCl_3$) δ ppm: 1.94 (3H, singlet); 3.24 (1H, doublet, J=9.9 Hz); 4.66 (1H, singlet).

EXAMPLE 60

13-(4-Ethoxy-3-methoxyphenethyloxy)milbemycin $A_4$ oxime

Mass Spectrum (m/e): 749 ($M^+$, $C_{43}H_{59}NO_{10}$).

Nuclear Magnetic Resonance Spectrum ($CDCl_3$) δ ppm: 1.94 (3H, singlet); 3.22 (1H, doublet, J=9.9 Hz); 4.66 (1H, singlet).

EXAMPLE 61

13-(2,6-Difluorophenethyloxy)milbemycin $A_4$ oxime

Mass Spectrum (m/e): 711 ($M^+$, $C_{40}H_{51}F_2NO_8$).

Nuclear Magnetic Resonance Spectrum ($CDCl_3$) δ ppm: 1.93 (3H, singlet); 3.22 (1H, doublet, J=9.9 Hz); 4.66 (1H, singlet).

EXAMPLE 62

13-(3-Nitrophenethyloxy)milbemycin $A_4$ oxime

Mass Spectrum (m/e): 720 ($M^+$, $C_{40}H_{52}N_2O_{10}$).

Nuclear Magnetic Resonance Spectrum ($CDCl_3$) δ ppm: 1.94 (3H, singlet); 3.20 (1H, doublet, J=9.9 Hz); 4.66 (1H, singlet).

EXAMPLE 63

13-(3-Methoxy-4-methoxymethoxyphenethyloxy) milbemycin $A_4$ oxime

Mass Spectrum (m/e): 765 ($M^+$, $C_{43}H_{59}NO_{11}$).

Nuclear Magnetic Resonance Spectrum ($CDCl_3$) δ ppm: 1.94 (3H, singlet); 3.22 (1H, doublet, J=9.5 Hz); 4.66 (1H, singlet).

EXAMPLE 64

13-[2-(4-Aminophenyl)ethoxy]milbemycin $A_4$ 0.70 g of zinc powder was added to a solution of 0.693 g of 13-[2-(4-nitrophenyl)ethoxy]milbemycin $A_4$ (prepared as described in Example 3) in 7 ml of 90% v/v aqueous acetic acid, whilst cooling with water, and the mixture was stirred for 20 minutes. At the end of this time, 50 ml of ethyl acetate were added to the reaction mixture, insoluble materials were removed by filtration, and the filtrate was washed three times with water. It was then dried over anhydrous sodium sulfate, and the solvent was removed by distillation to dryness under reduced pressure. The residue was purified by column chromatography through silica gel (ODS treated), eluted with 75% v/v aqueous acetonitrile), to afford 0.620 g of the title compound.

Mass Spectrum m/e: 677 ($M^+$, $C_{40}H_{55}NO_8$).

Nuclear Magnetic Resonance Spectrum ($CDCl_3$) δ ppm: 1.87 (3H, singlet); 3.21 (1H, doublet, J=9.9 Hz)1 3.95 (1H, doublet, J=6.2 Hz).

The compounds of Examples 65–66 were prepared by a similar procedure to that described in Example 64 above.

EXAMPLE 65

13-[2-(3-Amino-4-methoxyphenyl)ethoxy]milbemycin $A_4$

Mass Spectrum m/e: 707 ($M^+$, $C_{41}H_{57}NO_9$).

Nuclear Magnetic Resonance Spectrum ($CDCl_3$) δ ppm: 1.87 (3H, singlet); 3.21 (1H, doublet, J=9.9 Hz); 3.84 (3H, singlet); 3.95 (1H, doublet, J=6.2 Hz).

EXAMPLE 66

13-[2-(4-Amino-3-methoxyphenyl)ethoxy]milbemycin $A_4$

Mass Spectrum m/e: 707 ($M^+$, $C_{41}H_{57}NO_9$).

Nuclear Magnetic Resonance Spectrum ($CDCl_3$) δ ppm: 1.87 (3H, singlet); 3.22 (1H, doublet, J=9.9 Hz); 3.85 (3H, singlet); 3.95 (1H, doublet, J=6.2 Hz).

EXAMPLE 67

13-[2-(4-Benzoylaminophenyl)ethoxy]milbemycin $A_4$ 0.024 ml of pyridine and 0.035 ml of benzoyl chloride were added to a solution of 0.200 g of 13-[2-(4-aminophenyl)ethoxy]milbemycin $A_4$ (prepared as described in Example 35) in 3.0 ml of methylene chloride, and the mixture was stirred for 15 minutes. At the end of this time, the reaction mixture was poured into ice-water and extracted with methylene chloride. The extract was washed with 0.1N aqueous hydrochloric acid, with water, with a 4% w/v aqueous solution of sodium bicarbonate and with water, in that order. It was then dried over anhydrous sodium sulfate, and the solvent was removed by distillation to dryness under reduced pressure. The residue was purified by column chromatography through silica gel (ODS treated), eluted with 70% v/v aqueous acetonitrile), to afford 0.188 g of the title compound.

Mass Spectrum m/e: 763 ($M^+-H_2O$, $C_{47}H_{57}NO_8$).

Nuclear Magnetic Resonance Spectrum ($CDCl_3$) δ ppm: 1.87 (3H, singlet); 3.22 (1H, doublet, J=9.9 Hz): 3.95 (1H, doublet, J=5.9 Hz).

The compounds of Examples 68–76 were prepared by a similar procedure to that described in Example 67 above.

EXAMPLE 68

13-[2-(4-Acetamidophenyl)ethoxy]milbemycin $A_4$

Nuclear Magnetic Resonance Spectrum ($CDCl_3$) δ ppm: 1.87 (3H, singlet); 2.18 (3H, singlet); 3.20 (1H, doublet, J=9.9 Hz); 3.95 (1H, doublet, J=6.2 Hz).

EXAMPLE 69

13-{2-[4-(3,4-Dimethoxybenzoylamino)phenyl]ethoxy}milbemycin $A_4$

Nuclear Magnetic Resonance Spectrum ($CDCl_3$) δ ppm: 1.87 (3H, singlet): 3.22 (1H, doublet, J=9.9 Hz); 3.95 (3H, singlet); 3.96 (3H, singlet); 3.98 (1H, doublet, J=6.2 Hz).

EXAMPLE 70

13-[2-{4-Methoxycarbonylaminophenyl)ethoxy] milbemycin $A_4$

Mass Spectrum m/e: 735 ($M^+$, $C_{42}H_{57}NO_{10}$).

Nuclear Magnetic Resonance Spectrum ($CDCl_3$) δ ppm: 1.87 (3H, singlet); 3.20 (1H, doublet, J=9.5 Hz); 3.95 (1H, doublet, J=6.2 Hz).

EXAMPLE 71

13-[2-(4-Ethoxycarbonylaminophenyl)ethoxy]milbemycin $A_4$

Mass Spectrum m/e: 749 ($M^+$, $C_{43}H_{59}NO_{10}$).

Nuclear Magnetic Resonance Spectrum ($CDCl_3$) δ ppm: 1.87 (3H, singlet); 3.20 (1H, doublet, J=9.9 Hz); 3.95 (1H, doublet, J=6.2 Hz).

EXAMPLE 72

13-[2-(4-Butoxycarbonylaminophenyl)ethoxy]milbemycin $A_4$

Mass Spectrum m/e: 777 ($M^+$, $C_{45}H_{63}NO_{10}$).

Nuclear Magnetic Resonance Spectrum ($CDCl_3$) δ ppm: 1.87 (3H, singlet); 3.20 (1H, doublet, J=9.9 Hz); 3.95 (1H, doublet, J=6.2 Hz).

EXAMPLE 73

13-[2-(4-Isobutoxycarbonylaminophenyl)ethoxy] milbemycin $A_4$

Mass Spectrum m/e: 777 ($M^+$, $C_{45}H_{63}NO_{10}$).

Nuclear Magnetic Resonance Spectrum ($CDCl_3$) δ ppm: 1.87 (3H, singlet); 3.20 (1H, doublet, J=9.9 Hz); 3.95 (1H, doublet, J=6.2 Hz).

EXAMPLE 74

13-[2-(4-Benzyloxycarbonylaminophenyl)ethoxy] milbemycin $A_4$

Nuclear Magnetic Resonance Spectrum ($CDCl_3$) δ ppm: 1.87 (3H, singlet); 3.20 (1H, doublet, J=9.9 Hz); 3.95 (1H, doublet, J=6.2 Hz); 5.19 (2H, singlet).

EXAMPLE 75

13-[2-(4-Methanesulfonylaminophenyl)ethoxy]milbemycin $A_4$

Nuclear Magnetic Resonance Spectrum ($CDCl_3$) δ ppm: 1.87 (3H, singlet); 2.97 (3H, singlet); 3.20 (1H, doublet, J=9.9 Hz); 3.95 (1H, doublet, J=6.2 Hz); 6.39 (1H, singlet).

EXAMPLE 76

13-[2-(4-Benzenesulfonylaminophenyl)ethoxy]milbemycin $A_4$

Nuclear Magnetic Resonance Spectrum ($CDCl_3$) δ ppm: 1.87 (3H, singlet): 3.16 (1H, doublet, J=9.9 Hz); 3.95 (1H, doublet, J=6.2 Hz); 6.49 (1H, singlet).

EXAMPLE 77

13-{2-[4-(3-Phenylureido)phenyl]ethoxy}milbemycin $A_4$ 0.039 ml of phenylisocyanate was added to a solution of 0.200 g of 13-[2-(4-aminophenyl)ethoxy]milbemycin $A_4$ (prepared as described in Example 35) in 2.0 ml of tetrahydrofuran, and the mixture was stirred for 2 hours. At the end of this time, the reaction mixture was diluted with 20 ml of ethyl acetate, washed with water and dried over anhydrous sodium sulfate. The solvent was then removed by distillation to dryness under reduced pressure. The residue was purified by column chromatography (ODS: eluted with 80% v/v aqueous acetonitrile) to afford 0.207 g of the title compound.

Nuclear Magnetic Resonance Spectrum ($CDCl_3$, 270 MHz) δ ppm: 1.87 (3H, singlet); 3.21 (1H, doublet, J=9.9 Hz); 3.95 (1H, doublet, J=6.2 Hz); 6.56 (1H, singlet); 6.61 (1H, singlet).

The compounds of Examples 78–85 were prepared by a similar procedure to that described above.

EXAMPLE 78

13-{2-[4-(3-Methylureido)phenyl]ethoxy}milbemycin $A_4$

Nuclear Magnetic Resonance Spectrum (CDCl$_3$) δ ppm: 1.87 (3H, singlet); 2.82 (3H, doublet, J=4.8 Hz); 3.21 (1H, doublet, J=9.9 Hz); 3.95 (1H, doublet, J=6.2 Hz).

EXAMPLE 79

13-{2-[4-(3-Cyclohexylureido)phenyl]ethoxy}milbemycin $A_4$

Nuclear Magnetic Resonance Spectrum (CDCl$_3$) δ ppm: 1.87 (3H, singlet); 3.20 (1H, doublet, J=9.9 Hz); 3.95 (1H, doublet, J=6.2 Hz); 4.53 (1H, doublet, J=8.1 Hz); 6.12 (1H, singlet).

EXAMPLE 80

13-{2-[4-(3-o-Fluorophenylureido)phenyl]ethoxy}milbemycin $A_4$

Nuclear Magnetic Resonance Spectrum (CDCl$_3$) δ ppm: 1.87 (3H, singlet); 3.21 (1H, doublet, J=9.9 Hz); 3.96 (1H, doublet, J=6.2 Hz); 6.63 (1H, singlet).

EXAMPLE 81

13-{2-[4-(3-o-Methylphenylureido)phenyl]ethoxy}milbemycin $A_4$

Nuclear Magnetic Resonance Spectrum (CDCl$_3$) δ ppm: 1.87 (3H, singlet); 3.21 (1H, doublet, J=9.9 Hz); 3.95 (1H, doublet, J=6.2 Hz); 6.48 (1H, singlet); 6.52 (1H, singlet).

EXAMPLE 82

13-{2-[4-(3-α-Naphthylureido)phenyl]ethoxy}milbemycin $A_4$

Nuclear Magnetic Resonance Spectrum (CDCl$_3$) δ ppm: 1.87 (3H, singlet); 3.19 (1H, doublet, J=9.9 Hz); 3.95 (1H, doublet, J=6.2 Hz); 6.53 (1H, singlet); 6.71 (1H, singlet).

EXAMPLE 83

13-{2-[4-(3-p-Methoxyphenylureido)phenyl]ethoxy}milbemycin $A_4$

Nuclear Magnetic Resonance Spectrum (CDCl$_3$) δ ppm: 1.87 (3H, singlet); 3.21 (1H, doublet, J=9.5 Hz); 3.95 (1H, doublet, J=6.2 Hz); 6.36 (1H, singlet); 6.43 (1H, singlet).

EXAMPLE 84

13-{2-[4-(3-p-Nitrophenylureido)phenyl]ethoxy}milbemycin $A_4$

Nuclear Magnetic Resonance Spectrum (CDCl$_3$) δ ppm: 1.87 (3H, singlet); 3.21 (1H, doublet, J=9.5 Hz); 3.96 (1H, doublet, J=6.2 Hz); 6.83 (1H, singlet).

EXAMPLE 85

13-{2-[4-(3-p-Chlorophenylureido)phenyl]ethoxy}milbemycin $A_4$

Nuclear Magnetic Resonance Spectrum (CDCl$_3$) δ ppm: 1.87 (3H, singlet); 3.21 (1H, doublet, J=9.9 Hz); 3.95 (1H, doublet, J=6.2 Hz); 6.55 (1H, singlet); 6.65 (1H, singlet).

EXAMPLE 86

13-{2-[4-(3-phenylthioureido)phenyl]ethoxy}milbemycin $A_4$ 0.043 ml of phenylisothiocyanate was added to a solution of 0.200 g of 13-[2-(4-aminophenyl)ethoxy]milbemycin $A_4$ (prepared as described in Example 35) in 1.0 ml of tetrahydrofuran, and the mixture was stirred for 5 hours. At the end of this time, the reaction mixture was poured into ice-water and extracted with 20 ml of ethyl acetate. The extract was dried over anhydrous sodium sulfate and the solvent was removed by distillation to dryness under reduced pressure. The residue was purified by column chromatography-(ODS: eluted with 80% v/v aqueous acetonitrile) to afford 0.253 g of the title compound.

Nuclear Magnetic Resonance Spectrum (CDCl$_3$) δ ppm: 1.87 (3H, singlet); 3.21 (1H, doublet, J=9.5 Hz); 3.95 (1H, doublet, J=6.1 Hz); 7.67 (2H, singlet).

EXAMPLE 87

13-{2-[4-(3-m-Fluorophenylthioureido)phenyl]ethoxy}milbemycin $A_4$

The title compound was synthesized following a similar procedure to that described in Example 86, but using 3-fluorophenylisothiocyanate instead of the phenylisothiocyanate.

Nuclear Magnetic Resonance Spectrum (CDCl$_3$) δ ppm: 1.87 (3H, singlet); 3.21 (1H, doublet, J=9.5 Hz); 3.95 (1H, doublet, J=6.2 Hz); 7.60 (1H, singlet); 7.75 (1H, singlet).

EXAMPLE 88

13-[2-(4-Propionylaminophenyl)ethoxy]milbemycin $A_4$

Step 1

4.96 g of 13-[2-(4-nitrophenyl)ethoxy]milbemycin $A_4$ (prepared by the same procedure as that described in Example 32 were dissolved in 20 ml of dimethylformamide. 0.571 g of imidazole and 1.270 g of t-butyldimethylsilyl chloride were added to the resulting solution, and then the mixture was stirred at room temperature for 2.5 hours. At the end of this time, the reaction mixture was diluted with 200 ml of ethyl acetate, washed with water four times and dried over anhydrous sodium sulfate. The solvent was removed by evaporation to dryness under reduced pressure, and the residue was purified by column chromatography through silica gel, eluted with a 85:15 by volume mixture of cyclohexane and ethyl acetate, to give 5.08 g of the 5-silylated ether. The whole of this product was dissolved in 50 ml of 90% acetic acid, 5.00 g of zinc powder were added, and then the mixture was stirred for 20 minutes, whilst cooling wish water. The mixture was then diluted with 250 ml of ethyl acetate and the insoluble matter was filtered off. The filtrate was washed with water (three times), with a 4% v/v aqueous solution of sodium bicarbonate and with water, in that order, after which it was dried over anhydrous sodium sulfate. The solvent was then removed by evaporation to dryness under reduced pressure, and the residue was purified by column chromatography through silica gel (ODS treated), eluted with 90% v/v aqueous acetonitrile, to give 4.370 g of 13-[2-(4-aminophenyl)ethoxy]-5-O-t-butyldimethysilylmilbemycin $A_4$ Mass spectrum m/e: 791 ($M^+$, $C_{46}H_{69}NO_8Si$).

Nuclear Magnetic Resonance Spectrum (CDCl$_3$) δ ppm: 1.87 (3H, singlet); 3.21 (1H, doublet, J=9.9 Hz); 3.80 (1H, doublet, J=5.5 Hz); 6.61 (2H, doublet, J=8.4 Hz); 6.99 (2H, doublet, J=8.4 Hz).

Step 2

0.200 g of 13-[2-(4-aminophenyl)ethoxy]-5-O-t-butyl-dimethylsilylmilbemycin $A_4$ (prepared as described in Step 1) was dissolved in 2.0 ml of 1,2-dichloroethane. 0.024 ml of pyridine and 0.026 ml of propionyl chloride were then added, whilst ice-cooling, to the resulting solution, and then the mixture was stirred for 30 minutes. At the end of this time, the reaction mixture was diluted with 15 ml of ethyl acetate and wasted, in turn, with 0.5N aqueous hydrochloric acid, with water, with a 4% aqueous solution of sodium bicarbonate and with water. After the mixture had been dried over anhydrous sodium sulfate, the solvent was removed by evaporation to dryness under reduced pressure. The residue was dissolved in 2.0 ml of methanol and stirred at room temperature for 30 minutes in the presence of a catalytic amount of p-toluenesulfonic acid monohydrate. The reaction mixture was then diluted with 15 ml of ethyl acetate, washed, in turn, with a 4% aqueous solution of sodium bicarbonate and with water and dried over anhydrous sodium sulfate. The solvent was then removed by evaporation to dryness under reduced pressure, and the residue was purified by column chromatography through silica gel (ODS treated), eluted with 80% v/v aqueous acetonitrile, to give 0.187 g of the title compound.

Nuclear Magnetic Resonance Spectrum (CDCl$_3$) δ ppm: 1.87 (3H, singlet); 3.20 (1H, doublet, J=9.9 Hz); 3.95 (1H, doublet, J=6.2 Hz); 7.08 (1H, singlet).

Following a similar procedure to that described in Example 88, the compounds of Examples 89 to 92 were obtained.

EXAMPLE 89

13-[2-(4-Chloroacetamidophenyl)ethoxy]milbemycin $A_4$

Mass spectrum m/e: 753 (M$^+$, $C_{42}H_{56}ClNO_9$).

Nuclear Magnetic Resonance Spectrum (CDCl$_3$) δ ppm: 1.87 (3H, singlet); 3.20 (1H, doublet, J=9.9 Hz); 3.96 (1H, doublet, J=6.2 Hz); 4.19 (2H, singlet); 8.18 (1H, singlet).

EXAMPLE 90

13-[2-(4-Isonicotinoylaminophenyl)ethoxy]milbemycin $A_4$

Nuclear Magnetic Resonance Spectrum (CDCl$_3$) δ ppm: 1.79 (3H, singlet); 3.21 (1H, doublet, J=9.5 Hz); 3.80 (1H, doublet, J=5.5 Hz); 7.70 (2H, doublet, J=6.2 Hz); 7.80 (1H, singlet); 8.80 (2H, doublet, J=6.2 Hz).

EXAMPLE 91

13-[2-(4-Ethanesulfonylaminophenyl)ethoxy]milbemycin $A_4$

Mass spectrum m/e: 769 (M$^+$, $C_{42}H_{59}NO_{10}S$).

Nuclear Magnetic Resonance Spectrum (CDCl$_3$) δ ppm: 1.87 (3H, singlet); 3.10 (2H, quartet, J=7.5 Hz); 3.20 (1H, doublet, J=9.9 Hz); 3.95 (1H, doublet, J=6.2 Hz); 6.37 (1H, singlet).

EXAMPLE 92

13-[2-(4-Propanesulfonylaminophenyl)ethoxy]milbemycin $A_4$

Mass spectrum m/e: 783 (M$^+$, $C_{43}H_{61}NO_{10}S$).

Nuclear Magnetic Resonance Spectrum (CDCl$_3$) δ ppm: 1.87 (3H, singlet); 3.20 (1H, doublet, J=9.9 Hz); 3.96 (1H, doublet, J=6.2 Hz); 6.34 (1H, singlet).

EXAMPLE 93

13-[2-(4-Methoxyacetamidophenyl)ethoxy]milbemycin $A_4$ 0.130 g of 13-[2-(4-aminophenyl)ethoxy]milbemycin $A_4$ (prepared by a similar procedure to that described in Example 64) was dissolved in 1.1 ml of 1.2-dichloroethane. 0.024 ml of pyridine and 0.024 g of methoxyacetyl chloride were added, whilst ice-cooling, to the resulting solution, and then the mixture was stirred for 30 minutes. At the end of this time, the reaction mixture was diluted with 15 ml of ethyl acetate and washed, in turn, with 0.5N hydrochloric acid, with water, with a 4% aqueous solution of sodium bicarbonate and with water. After the mixture had been dried over anhydrous sodium sulfate, the solvent was removed by evaporation to dryness under reduced pressure. The residue was purified by column chromatography through silica gel (ODS treated), eluted with 80% v/v aqueous acetonitrile, to give 0.123 g of the title compound.

Mass spectrum m/e: 749 (M$^+$, $C_{43}H_{59}NO_{10}$).

Nuclear Magnetic Resonance Spectrum (CDCl$_3$) δ ppm: 1.87 (3H, singlet); 3.21 (1H, doublet, J=9.9 Hz); 3.50 (3H, singlet); 3.95 (1H, doublet, J=6.2 Hz); 4.01 (2H, singlet); 8.19 (1H, singlet).

Following a similar procedure to that described in Example 93, the compounds of Examples 94 to 112 were obtained and have the properties shown below.

EXAMPLE 94

13-[2-(4-Phenoxyacetamidophenyl)ethoxy]milbemycin $A_4$

Mass Spectrum (m/e): 811 (M$^+$, $C_{48}H_{61}NO_{10}$).

Nuclear Magnetic Resonance Spectrum (CDCl$_3$) δ ppm: 1.83 (3H, singlet); 3.21 (1H, doublet, J=9.9 Hz); 3.95 (1H, doublet, J=6.2 Hz); 4.61 (2H, singlet); 8.23 (2H, singlet).

EXAMPLE 95

13-{2-[4-(2-Furoyl)aminophenyl]ethoxy}milbemycin $A_4$

Mass Spectrum (m/e): 771 (M$^+$, $C_{45}H_{57}NO_{10}$).

Nuclear Magnetic Resonance Spectrum (CDCl$_3$) δ ppm: 1.87 (3H, singlet); 3.21 (1H, doublet, J=9.9 Hz); 3.95 (1H, doublet, J=6.2 Hz); 8.03 (1H, singlet).

EXAMPLE 96

13-{2-[4-(2-Thenoyl)aminophenyl]ethoxy}milbemycin $A_4$

Nuclear Magnetic Resonance Spectrum (CDCl$_3$) δ ppm: 1.87 (3H, singlet); 3.21 (1H, doublet, J=9.9 Hz); 3.95 (1H, doublet, J=6.2 Hz); 7.13, 7.54 & 7.61 (1H×3, multiplet); 7.62 (1H, singlet).

EXAMPLE 97

13-[2-(4-Cyclobutylcarbonylaminophenyl)ethoxy]milbemycin $A_4$

Mass Spectrum (m/e): 759 (M$^+$, $C_{45}H_{61}NO_9$).

Nuclear Magnetic Resonance Spectrum (CDCl$_3$) δ ppm: 1.87 (3H, singlet); 3.20 (1H, doublet, J=9.9 Hz); 3.95 (1H, doublet, J=6.2 Hz); 6.95 (1H, singlet).

EXAMPLE 98

13-{2-[4-(Methoxalylamino)phenyl]ethoxy}milbemycin $A_4$

Mass Spectrum (m/e): 763 (M$^+$, $C_{43}H_{57}NO_{11}$).

Nuclear Magnetic Resonance Spectrum (CDCl$_3$) δ ppm: 1.87 (3H, singlet); 3.20 (1H, doublet, J=9.9 Hz); 3.95 (1H, doublet, J=6.2 Hz); 3.97 (3H, singlet); 8.80 (1H, singlet).

EXAMPLE 99

13-{2-[4-(Ethoxycarbonylacetamido)phenyl]ethoxy}milbemycin $A_4$,

Nuclear Magnetic Resonance Spectrum ($CDCl_3$) δ ppm: 1.87 (3H, singlet); 3.20 (1H, doublet. J=9.5 Hz); 3.46 (2H, singlet); 3.95 (1H, doublet, J=6.2 Hz); 4.26 (2H, quartet, J=7.0 Hz); 9.15 (1H, singlet).

EXAMPLE 100

13-[2-(4-Cyclopropylcarbonylaminophenyl)ethoxy]milbemycin $A_4$

Mass Spectrum (m/e): 745 ($M^+$, $C_{45}H_{59}NO_9$).

Nuclear Magnetic Resonance Spectrum ($CDCl_3$) δ ppm: 1.87 (3H, singlet); 3.20 (1H, doublet, J=9.9 Hz); 3.95 (1H, doublet, J=6.2 Hz); 7.29 (1H, singlet).

EXAMPLE 101

13-[2-(4-Butyramidophenyl)ethoxy]milbemycin $A_4$

Mass Spectrum (m/e): 747 ($M^+$, $C_{44}H_{61}NO_9$).

Nuclear Magnetic Resonance Spectrum ($CDCl_3$) δ ppm: 1.87 (3H, singlet); 3.20 (1H, doublet, J=9.9 Hz); 3.95 (1H, doublet, J=6.2 Hz); 7.06 (1H, singlet).

EXAMPLE 102

13-[2-(4-Crotonoylaminophenyl)ethoxy]milbemycin $A_4$

Mass Spectrum (m/e): 745 ($M^+$, $C_{45}H_{59}NO_9$).

Nuclear Magnetic Resonance Spectrum ($CDCl_3$) δ ppm: 1.87 (3H, singlet); 3.21 (1H, doublet, J=9.5 Hz); 3.95 (1H, doublet, J=6.2 Hz); 7.05 (1H, singlet).

EXAMPLE 103

13-{2-[4-(4-Cyanobenzamido)phenyl]ethoxy}milbemycin $A_4$,

Mass Spectrum (m/e): 770 ($M^+$–36).

Nuclear Magnetic Resonance Spectrum ($CDCl_3$) δ ppm: 1.87 (3H, singlet); 3.22 (1H, doublet, J=9.5 Hz); 3.95 (1H, doublet, J=6.2 Hz); 7.79 (1H, singlet).

EXAMPLE 104

13-{2-[4-(4-Methoxycarbonylbenzamido)phenyl]ethoxy}milbemycin $A_4$,

Mass Spectrum (m/e): 803 ($M^+$–36).

Nuclear Magnetic Resonance Spectrum ($CDCl_3$) δ ppm: 1.87 (3H, singlet); 3.22 (1H, doublet, J=9.5 Hz); 3.95 (1H, doublet, J=6.2 Hz); 3.96 (3H, singlet); 7.79 (1H, singlet).

EXAMPLE 105

13-[2-(4-Trifluoroacetamidophenyl)ethoxy]milbemycin $A_4$

Mass Spectrum (m/e): 773 ($M^+$, $C_{42}H_{54}F_3NO_9$).

Nuclear Magnetic Resonance Spectrum ($CDCl_3$) δ ppm: 1.87 (3H, singlet); 3.20 (1H, doublet, J=9.8 Hz); 3.95 (1H, doublet, J=5.9 Hz); 9.86 (1H, singlet).

EXAMPLE 106

13-[2-(4-Fluoroacetamidophenyl)ethoxy]milbemycin $A_4$

Mass Spectrum (m/e): 737 ($M^+$, $C_{42}H_{56}FNO_9$).

Nuclear Magnetic Resonance Spectrum ($CDCl_3$) δ ppm: 1.87 (3H, singlet); 3.21 (1H, doublet, J=9.8 Hz); 3.95 (1H, doublet, J=5.9 Hz); 4.92 (2H, doublet, J=47.4 Hz).

EXAMPLE 107

13-[2-(4-Cyanomethanesulfonylaminophenyl)ethoxy]milbemycin $A_4$

Nuclear Magnetic Resonance Spectrum ($CDCl_3$) δ ppm: 1.87 (3H, singlet); 3.20 (1H, doublet, J=9.9 Hz); 3.96 (2H, singlet); 3.96 (1H, doublet, J=6.2 Hz).

EXAMPLE 108

13-{2-[4-(4-Methoxybenzenesulfonylamino)phenyl]ethoxy}milbemycin $A_4$,

Mass Spectrum (m/e): 847 ($M^+$, $C_{47}H_{61}NO_{11}S$).

Nuclear Magnetic Resonance Spectrum ($CDCl_3$) δ ppm: 1.87 (3H, singlet); 3.16 (1H, doublet, J=9.9 Hz); 3.83 (3H, singlet); 3.96 (1H, doublet, J=6.2 Hz); 6.39 (1H, singlet).

EXAMPLE 109

13-[2-(4-Isopropoxycarbonylaminophenyl)ethoxy]milbemycin $A_4$

Mass Spectrum (m/e): 764 ($M^+$+1).

Nuclear Magnetic Resonance Spectrum ($CDCl_3$) δ ppm: 1.87 (3H, singlet); 3.21 (1H, doublet, J=9.9 Hz); 3.96 (1H, doublet, J=6.2 Hz); 5.01 (1H, multiplet); 6.47 (1H, singlet).

EXAMPLE 110

13-[2-(4-Vinyloxycarbonylaminophenyl)ethoxy]milbemycin $A_4$

Nuclear Magnetic Resonance Spectrum ($CDCl_3$) δ ppm: 1.87 (3H, singlet); 3.20 (1H, doublet, J=9.9 Hz); 3.95 (1H, doublet, J=6.2 Hz); 4.53 (1H, doublet of doublets, J=1.8 & 6.2 Hz); 4.83 (1H, doublet of doublets, J=1.8 & 13.9 Hz); 6.65 (1H, singlet).

EXAMPLE 111

13-[2-(4-Allyloxycarbonylaminophenyl)ethoxy]milbemycin $A_4$

Nuclear Magnetic Resonance Spectrum ($CDCl_3$) δ ppm: 1.87 (3H, singlet); 3.20 (1H, doublet, J=9.9 Hz); 3.95 (1H, doublet, J=6.2 Hz); 4.66 (2H, multiplet); 5.26 (1H, multiplet); 5.36 (1H, multiplet); 5.97 (1H, multiplet); 6.57 (1H, singlet).

EXAMPLE 112

13-[2-(4-Ethoxycarbonylamino-3-methoxyphenyl)ethoxy]milbemycin $A_4$

Mass Spectrum (m/e): 779 ($M^+$, $C_{44}H_{61}NO_{11}$).

Nuclear Magnetic Resonance Spectrum ($CDCl_3$) δ ppm: 1.87 (3H, singlet); 3.21 (1H, doublet, J=9.9 Hz); 3.85 (3H, singlet); 3.96 (1H, doublet, J=6.2 Hz); 4.22 (1H, quartet, J=7.0 Hz);

EXAMPLE 113

13-[2-(4-Cyanoacetamidophenyl)ethoxy]milbemycin $A_4$ 0.050 ml of pyridine and 0.100 g of 2-chloroformyl-1,2,4-triazolo[4,3-a]pyridin-3-one were added to a solution of 0.0425 g of cyanoacetic acid in 2.5 ml of methylene chloride, and then the mixture was stirred at room temperature for 30 minutes. At the end of this time, 0.203 g of 13-[2-(4-aminophenyl)ethoxy]milbemycin $A_4$ (prepared by a similar procedure to that described in Example 64) was added to the mixture, and then the whole mixture was stirred at room temperature for a further 1 hour. At the end of this time, the reaction mixture was diluted with 15 ml of ethyl acetate and filtered. The filtrate was wasted, in turn, with 0.5N aqueous hydrochloric acid, with water, with a 4% v/v aqueous solution of sodium bicarbonate and with water, after which it was dried over anhydrous sodium sulfate. The solvent was then removed by evaporation to dryness under reduced pressure, and the residue was purified by column chromatography through silica gel (ODS treated), eluted with 80% v/v aqueous acetonitrile, to give 0.190 g of the title compound.

Nuclear Magnetic Resonance Spectrum (CDCl$_3$) δ ppm: 1.87 (3H, singlet); 3.20 (1H, doublet, J=9.9 Hz); 3.54 (2H, singlet); 3.95 (1H, doublet, J=6.2 Hz); 7.70 (1H, singlet).

Following a similar procedure to that described in Example 113, the Compounds of Examples 114 to 124 were obtained and had the properties shown below.

EXAMPLE 114

13-[2-(4-Methoxycarbonylacetamidophenyl)ethoxy]milbemycin A$_4$

Nuclear Magnetic Resonance Spectrum (CDCl$_3$) δ ppm: 1.87 (3H, singlet); 3.21 (1H, doublet, J=9.5 Hz); 3.48 (2H, singlet); 3.81 (3H, singlet); 3.95 (1H, doublet, J=6.2 Hz); 9.09 (1H, singlet).

EXAMPLE 115

13-[2-(4-Difluoroacetamidophenyl)ethoxy]milbemycin A$_4$

Mass Spectrum (m/e): 755 (M$^+$, C$_{42}$H$_{55}$F$_2$NO$_9$).

Nuclear Magnetic Resonance Spectrum (CDCl$_3$) δ ppm: 1.87 (3H, singlet); 3.20 (1H, doublet, J=9.8 Hz); 3.95 (1H, doublet, J=5.9 Hz); 6.01 (1H, triplet, J=54.4 Hz); 7.85 (1H, singlet).

EXAMPLE 116

13-{2-[4-(2-Cyanopropionamido)phenyl]ethoxy}milbemycin A$_4$

Mass Spectrum (m/e): 758 (M$^+$, C$_{44}$H$_{58}$N$_2$O$_9$).

Nuclear Magnetic Resonance Spectrum (CDCl$_3$) δ ppm: 1.87 (3H, singlet); 3.22 (1H, doublet, J=9.5 Hz); 3.95 (1H, doublet, J=5.9 Hz); 3.57 (1H, quartet, J=7.3 Hz); 7.71 (1H, singlet).

EXAMPLE 117

13-[2-(4-Cyanomethylthioacetamidophenyl)ethoxy]milbemycin A$_4$

Nuclear Magnetic Resonance Spectrum (CDCl$_3$) δ ppm: 1.87 (3H, singlet); 3.20 (1H, doublet, J=9.5 Hz); 3.50 & 3.55 (2H×2, each singlet); 3.95 (1H, doublet, J=6.2 Hz); 7.87 (1H, singlet).

EXAMPLE 118

13-[2-(4-Acetylcarbonylaminophenyl)ethoxy]milbemycin A$_4$

Mass Spectrum (m/e): 747 (M$^+$, C$_{43}$H$_{57}$NO$_{10}$).

Nuclear Magnetic Resonance Spectrum (CDCl$_3$) δ ppm: 1.87 (3H, singlet); 2.57 (3H, singlet); 3.20 (1H, doublet, J=9.9 Hz); 3.95 (1H, doublet, J=6.2 Hz); 8.68 (1H, singlet).

EXAMPLE 119

13-{2-[4-(1-t-Butoxycarbonylpiperidine-4-carbonylamino)phenyl]ethoxy}milbemycin A$_4$ Nuclear Magnetic Resonance Spectrum (CDCl$_3$) δ ppm: 1.59 (9H, singlet); 1.87 (3H, singlet); 3.20 (1H, doublet, J=9.5 Hz); 3.95 (1H, doublet, J=6.3 Hz); 7.17 (1H, singlet).

EXAMPLE 120

13-[2-4-Actyloylaminophenyl)ethoxy]milbemycin A$_4$

Mass Spectrum (m/e): 731 (M$^+$, C$_{43}$H$_{57}$NO$_9$).

Nuclear Magnetic Resonance Spectrum (CDCl$_3$) δ ppm: 1.87 (3H, singlet); 3.21 (1H, doublet, J=9.9 Hz); 3.95 (1H, doublet, J=6.2 Hz); 6.22 (1H, doublet of doublets, J=10.3 & 16.9 Hz); 6.42 (1H, doublet of doublets, J=1.5 & 16.9 Hz); 8.68 (1H, singlet).

EXAMPLE 121

13-{2-[4-(2-Butynoylamino)phenyl]ethoxy}milbemycin A$_4$

Mass Spectrum (m/e): 743 (M$^+$, C$_{44}$H$_{57}$NO$_9$).

Nuclear Magnetic Resonance Spectrum (CDCl$_3$) δ ppm: 1.87 (3H, singlet); 2.00 (3H, singlet); 3.20 (1H, doublet, J=9.9 Hz); 3.95 (1H, doublet, J=6.2 Hz); 7.32 (1H, singlet).

EXAMPLE 122

13-{2-[4-(Pyrazin-2-ylcarbonylamino)phenyl]ethoxy}milbemycin A$_4$

Mass Spectrum (m/e): 783 (M$^+$, C$_{45}$H$_{57}$N$_3$O$_9$).

Nuclear Magnetic Resonance Spectrum (CDCl$_3$) δ ppm: 1.87 (3H, singlet); 3.22 (1H, doublet, J=9.9 Hz); 3.95 (1H, doublet, J=6.2 Hz); 8.59 (1H, doublet of doublets, J=1.5 & 2.6 Hz); 8.81 (1H, doublet, J=2.6 Hz); 9.52 (1H, doublet, J=1.5 Hz); 9.63 (1H, singlet).

EXAMPLE 123

13-{2-[4-(3,4-dihydropyran-2-ylcarbonylamino)phenyl]ethoxy}milbemycin A$_4$

Mass Spectrum (m/e): 787 (M$^+$, C$_{46}$H$_{61}$NO$_{10}$).

Nuclear Magnetic Resonance Spectrum (CDCl$_3$) δ ppm: 1.87 (3H, singlet); 3.21 (1H, doublet, J=9.9 Hz); 3.95 (1H, doublet, J=6.2 Hz); 4.87 (1H, multiplet); 6.23 (1H, multiplet); 8.17 (1H, singlet).

EXAMPLE 124

13-[2-(4-Cinnamoylaminophenyl)ethoxy]milbemycin A$_4$

Mass Spectrum (m/e): 789 (M$^+$−18).

Nuclear Magnetic Resonance Spectrum (CDCl$_3$) δ ppm: 1.87 (3H, singlet); 3.22 (1H, doublet, J=9.5 Hz); 3.95 (1H, doublet, J=5.9 Hz); 6.53 (1H, doublet, J=15.6 Hz); 7.28 (1H, doublet, J=15.6 Hz).

EXAMPLE 125

13-[2-(4-Formamidophenyl)ethoxy]-5-O-formylmilbemycin A$_4$ 0.360 ml of pyridine and 0.420 ml of acetic anhydride were added, whilst ice-cooling, to a solution of 0.170 ml of formic acid in 1.0 ml of methylene chloride, and then the mixture was stirred for 15 minutes. At the end of this time, 0.150 g of 13-[2-(4-aminophenyl) ethoxy]milbemycin A$_4$ (prepared by a similar procedure to that described in Example 64) was added, and then the whole mixture was stirred at room temperature for a further 20 minutes. At the end of this time, the reaction mixture was diluted with 15 ml of ethyl acetate and washed, in turn, with 0.5N aqueous hydrochloric acid, with water, with a 4% v/v aqueous solution of sodium bicarbonate and with water, after which it was dried over anhydrous sodium sulfate. The solvent was then removed by evaporation to dryness under reduced pressure, and the resulting residue was purified by column chromatography through silica gel, eluted with a 3:1 by volume mixture of cyclohexane and ethyl acetate, to give 0.119 g of the title compound.

Mass spectrum m/e: 705 (M$^+$−28).

Nuclear Magnetic Resonance Spectrum (CDCl$_3$) δ ppm: 1.87 (3H, singlet); 3.20 (1H, doublet, J=9.9 Hz); 4.08 (1H, singlet); 5.67 (1H, doublet, J=6.2 Hz).

EXAMPLE 126

13-[2-(4-Glycylaminophenyl)ethoxy]milbemycin $A_4$ 0.420 ml of triethylamine and 0.600 g of 2-chloroformyl-1,2,4-triazolo[4,3-a]pyridin-3-one were added to a mixture of 0.751 g of N-trichloroethoxycarbonylglycine and 3.0 ml of 1,2-dichloroethane, and then the mixture was stirred at room temperature for 30 minutes. At the end of this time, 1.000 g of 13-[2-(4-aminophenyl)ethoxy]milbemycin $A_4$ (prepared by a similar procedure to that described in Example 64) was added, and then the whole mixture was stirred at room temperature for a further 1 hour. The reaction mixture was then diluted with 25 ml of ethyl acetate and filtered. The filtrate was washed, in turn, with 0.5 N aqueous hydrochloric acid, with water, with a 4% v/v aqueous solution of sodium bicarbonate and with water, after which it was dried over anhydrous sodium sulfate. The solvent was then removed by evaporation to dryness under reduced pressure, and the resulting residue was purified by column chromatography through silica gel, eluted with a 3:1 by volume mixture of cyclohexane and ethyl acetate, to give 1.530 g of 13-[2-(4-trichloroethoxycarbonylglycylaminophenyl) ethoxy] milbemycin $A_4$. The whole of this product was dissolved in 6.0 ml of 90% acetic acid, 1.53 g of zinc powder were added, and then the mixture was stirred for 20 minutes, whilst cooling with water. The mixture was then diluted with 250 ml of ethyl acetate and the insoluble matter was filtered off. The filtrate was washed with water, and the white crystals which precipitated were collected by filtration to give 0.445 g of the title compound in the form of the hydrochloride. The filtrate was then subjected to column chromatography through silica gel (ODS treated), eluded with 90% v/v aqueous acetonitrile containing 1% by volume acetic acid, to give a further 0.054 g of the title compound as the hydrochloride.

EXAMPLE 127

13-[2-(4-N-Acetylglycylaminophenyl)ethoxy]milbemycin $A_4$ 0.100 g of 13-[2-(4-glycylaminophenyl)ethoxy milbemycin $A_4$ (prepared as described in Example 126) was suspended in 1.0 ml of tetrahydrofuran. 0.042 ml of triethylamine and 0.014 ml of acetic anhydride were then added, whilst ice-cooling, to the suspension, and then the mixture was stirred for 30 minutes. The reaction mixture was then diluted with 15 ml of ethyl acetate and washed, in turn, with 0.5N aqueous hydrochloric acid, with water, with a 4% v/v aqueous solution of sodium bicarbonate and with water, after which it was dried over anhydrous sodium sulfate. The solvent was then removed by evaporation to dryness under reduced pressure, and the resulting residue was purified by column chromatography through silica gel (ODS treated), eluted with 80% v/v aqueous acetonitrile, to give 0.079 g of the title compound.

Mass spectrum m/e: 776 ($M^+$, $C_{44}H_{60}N_2O_{10}$).

Nuclear Magnetic Resonance Spectrum (CDCl$_3$) δ ppm: 1.87 (3H, singlet); 3.20 (1H, doublet, J=9.9 Hz); 3.95 (1H, doublet, J=6.2 Hz); 4.08 (2H, doublet, J=5.5 Hz); 6.44 (1H, singlet).

Following a similar procedure to that described in Example 127, the compounds of Examples 128 to 130 were obtained.

EXAMPLE 128

13-[2-(4-N-Methoxycarbonylglycylaminophenyl)ethoxy] milbemycin $A_4$

Nuclear Magnetic Resonance Spectrum (CDCl$_3$) δ ppm: 1.87 (3H, singlet); 3.20 (1H, doublet, J=9.5 Hz); 3.75 (3H, singlet); 4.00 (2H, singlet); 7.83 (1H, singlet).

EXAMPLE 129

13-{2-(4-(3-Methylureidoacetamido)phenyl] ethoxymilbemycin $A_4$

Nuclear Magnetic Resonance Spectrum (CDCl$_3$) δ ppm: 1.87 (3H, singlet); 2.78 (3H, doublet, J=4.8 Hz); 3.20 (1H, doublet, J=9.9 Hz); 3.95 (1H, doublet, J=6.2 Hz); 4.04 (2H, doublet, J=5.1 Hz); 4.83 (1H, quartet, J=4.8 Hz); 5.59 (1H, triplet, J=5.1 Hz).

EXAMPLE 130

13-{2-[4-(3-Phenylureidoacetamido)phenyl] ethoxymilbemycin $A_4$

Nuclear Magnetic Resonance Spectrum (CDCl$_3$) δ ppm: 1.86 (3H, singlet); 3.20 (1H, doublet, J=9.9 Hz); 3.95 (1H, doublet, J=5.9 Hz); 4.13 (2H, doublet, J=5.4 Hz); 6.38 (1H, triplet, J=5.4 Hz); 6.36 & 8.83 (1H×2, singlet).

EXAMPLE 131

13-{2-[4-(1,2,4-Triazolo[4,3-a]pyridin-3-on-2-ylcarbonylamino) phenyl]ethoxy milbemycin $A_4$ 0.150 ml of pyridine and 0.300 g of 2-chloroformyl-1,2, 4-triazolo[4,3-a]pyridin-3-one were added, whilst ice-cooling, to a solution of 1.020 g of 13-[2-(4-aminophenyl) ethoxy]milbemycin $A_4$ (prepared by a similar procedure to that described in Example 64) in 10.0 ml of 1,2-dichloroethane, and then the mixture was stirred at room temperature for 30 minutes. At the end of this time, the reaction mixture was diluted with 50 ml of ethyl acetate and filtered. The filtrate was washed, in turn, with 0.5N aqueous hydrochloric acid, with water, with a 4% v/v aqueous solution of sodium bicarbonate and with water, after which it was dried over anhydrous sodium sulfate. The solvent was then removed by evaporation to dryness under reduced pressure, and the resulting residue was purified by column chromatography through silica gel (ODS treated), eluted with 80% v/v aqueous acetonitrile, to give 1.136 g of the title compound.

Nuclear Magnetic Resonance Spectrum (CDCl$_3$) δ ppm: 1.87 (3H, singlet); 3.22 (1H, doublet, J=9.9 Hz); 3.96 (1H, doublet, J=6.2 Hz); 6.60 (1H, multiplet); 7.80 (1H, doublet of doublets, J=1.1 & 7.3 Hz); 10.10 (1H, singlet).

EXAMPLE 132

13-{2-[p-3-(2-Hydroxyethyl)ureidophenyl] ethoxymilbemycin $A_4$ 0.135 g of 13-{2-[4-(1,2,4-triazolo[4.3-a]pyridin-3-on-2-ylcarbonylamino)phenyl]ethoxy milbemycin $A_4$ (prepared as described in Example 131) was dissolved in 1.0 ml of dimethylformamide. 0.020 g of ethanolamine was added, and then the mixture was stirred at room temperature for 20 minutes. At the end of this time, the reaction mixture was diluted with 15 ml of ethyl acetate and washed, in turn, with 0.5N aqueous hydrochloric acid, with water, with a 4% v/v aqueous solution of sodium bicarbonate and with water, after which it was dried over anhydrous sodium sulfate. The solvent was then removed by evaporation to dryness under reduced pressure, and the resulting residue was purified by column chromatography through silica gel (ODS treated), eluted with 80% v/v aqueous acetonitrile, to give 0.106 g of the title compound.

Mass spectrum m/e: 677 (M$^+$–87).

Nuclear Magnetic Resonance Spectrum (CDCl$_3$) δ ppm: 1.87 (3H, singlet); 2.40 (1H, doublet, J=8.5 Hz); 3.20 (1H, doublet, J=9.9 Hz); 3.4 (2H, multiplet); 3.7 (2H, multiplet); 3.95 (1H, doublet, J=5.9 Hz); 6.66 (1H, singlet).

Following a similar procedure to that described in Example 132, the compounds of Examples 133 to 149 were obtained and had the properties shown below.

EXAMPLE 133

13-[2-(p-Ureidophenyl)ethoxy]milbemycin A$_4$

Mass spectrum m/e: 677 (M$^+$–43).

Nuclear Magnetic Resonance Spectrum (CDCl$_3$) δ ppm: 1.87 (3H, singlet); 2.38 (1H, doublet, J=8.1 Hz); 3.21 (1H, doublet, J=9.5 Hz); 3.96 (1H, doublet, J=6.2 Hz); 4.68 (2H, singlet); 6.45 (1H, singlet).

EXAMPLE 134

13-{2-[4-(3,3-Dimethylureido)phenyl]ethoxy}milbemycin

Mass spectrum m/e: 677 (M$^+$–71).

Nuclear Magnetic Resonance Spectrum (CDCl$_3$). δ ppm: 1.87 (3H, singlet); 3.06 (6H, singlet): 3.21 (1H, doublet, J=9.8 Hz); 3.96 (1H, doublet, J=6.3 Hz); 6.24 (1H, singlet).

EXAMPLE 135

13-{2-[p-3-(2-Thioethyl)ureidophenyl]ethoxy}milbemycin A$_4$

Mass spectrum m/e: 758 (M$^+$, C$_{44}$H$_{58}$N$_2$O$_9$).

Nuclear Magnetic Resonance Spectrum (CDCl$_3$) δ ppm: 1.87 (3H, singlet); 2.85 (2H, multiplet); 3.20 (1H, doublet, J=9.8 Hz); 3.95 (1H, doublet. J=6.3 Hz); 6.56 & 7.26 (1H×2, each singlet).

EXAMPLE 136

13-{2-[4-(3-Cyclopropylureido)phenyl]ethoxy}milbemycin A$_4$

Mass spectrum m/e: 677 (M$^+$–83).

Nuclear Magnetic Resonance Spectrum (CDCl$_3$) δ ppm: 1.87 (3H, singlet); 2.59 (1H, multiplet); 3.21 (1H, doublet, J=9.8 Hz); 3.96 (1H, doublet, J=5.9 Hz); 4.84 (1H, singlet); 6.77 (1H, singlet).

EXAMPLE 137

13-{2-[p-3-(2-Pyridyl)ureidophenyl]ethoxy}milbemycin A$_4$

Nuclear Magnetic Resonance Spectrum (CDCl$_3$) δ ppm: 1.86 (3H, singlet); 3.23 (1H, doublet, J=9.8 Hz); 3.96 (1H, doublet, J=6.3 Hz); 6.83 (1H, doublet, J=9.3 Hz); 6.94 & 7.64 (2H, multiplet); 8.26 (1H, doublet of doublets, J=1.5 & 4.9 Hz); 7.92 (1H, singlet); 11.64 (1H, singlet).

EXAMPLE 138

13-{2-[p-3-(2-Thiazolinyl)ureidophenyl]ethoxy}milbemycin A$_4$

Mass spectrum m/e: 677 (M$^+$–128).

Nuclear Magnetic Resonance Spectrum (CDCl$_3$) δ ppm: 1.87 (3H, singlet); 3.21 (1H, doublet, J=9.9 Hz); 3.3 (2H, multiplet); 3.9 (2H, multiplet); 3.96 (1H, doublet, J=6.2 Hz).

EXAMPLE 139

13-{2-[p-3-(2-Thiazolyl)ureidophenyl]ethoxy}milbemycin A$_4$

Mass spectrum m/e: 677 (M$^+$–126).

Nuclear Magnetic Resonance Spectrum (CDCl$_3$) δ ppm: 1.79 (3H, singlet); 3.23 (1H, doublet, J=9.9 Hz); 3.98 (1H, doublet, J=6.2 Hz); 6.86 & 7.34 (1H×2, each doublet, J=3.7 Hz).

EXAMPLE 140

13-{2-[4-(Morpholinocarbonylamino)phenyl]ethoxy}milbemycin A$_4$

Mass spectrum m/e: 677 (M$^+$–113).

Nuclear Magnetic Resonance Spectrum (CDCl$_3$) δ ppm: 1.79 (3H, singlet); 3.21 (1H, doublet, J=9.5 Hz); 3.47 & 3.74 (4H×2, multiplet); 3.95 (1H, doublet, J=6.2 Hz); 6.26 (1H, singlet).

EXAMPLE 141

13-[2-(4-Carbazoylaminophenyl)ethoxy]milbemycin A$_4$

Mass spectrum m/e: 703 (M$^+$–32), 677 (M$^+$–58).

Nuclear Magnetic Resonance Spectrum (CDCl$_3$) δ ppm: 1.87 (3H, singlet); 3.21 (1H, doublet, J=9.9 Hz); 3.84 (2H, broad singlet); 3.96 (1H, doublet, J=6.2 Hz); 5.96 & 8.07 (1H×2, each singlet).

EXAMPLE 142

13-{2-[4-(2-Methylcarbazoylamino)phenyl]ethoxy}milbemycin A$_4$

Mass spectrum m/e: 677 (M$^+$–72).

Nuclear Magnetic Resonance Spectrum (CDCl$_3$) δ ppm: 1.87 (3H, singlet); 3.21 (1H, doublet, J=9.5 Hz); 3.23 (3H, singlet); 3.70 (2H, singlet); 3.96 (1H, doublet, J=6.2 Hz); 8.52 (1H, singlet).

EXAMPLE 143

13-{2-[4-(3,3-Dimethylcarbazoylamino)phenyl]ethoxy}milbemycin A$_4$

Mass spectrum m/e: 677 (M$^+$–86).

Nuclear Magnetic Resonance Spectrum (CDCl$_3$) δ ppm: 1.87 (3H, singlet); 2.59 (6H, singlet); 3.21 (1H, doublet, J=9.9 Hz); 3.96 (1H, doublet, J=6.2 Hz); 5.13 & 8.06 (1H×2, each singlet).

EXAMPLE 144

13-{2-[4-(3-perhydroazepinylureido)phenyl]ethoxy}milbemycin A$_4$

Nuclear Magnetic Resonance Spectrum (CDCl$_3$) δ ppm: 1.87 (3H, singlet); 3.21 (1H, doublet, J=9.9 Hz); 3.96 (1H, doublet, J=6.2 Hz); 5.60 & 8.17 (1H×2, each singlet).

EXAMPLE 145

13-{2-[4-(3-Morpholinoureido)phenyl]ethoxy}milbemycin A$_4$

Nuclear Magnetic Resonance Spectrum (CDCl$_3$) δ ppm: 1.87 (3H, singlet); 3.21 (1H, doublet, J=9.9 Hz); 3.95 (1H, doublet, J=6.2 Hz); 5.40 & 7.97 (1H×2, each singlet).

EXAMPLE 146

13-{2-[4-(3-Phenylcarbazoylamino)phenyl]ethoxy}milbemycin A$_4$

Mass spectrum m/e: 677 (M$^+$–134).

Nuclear Magnetic Resonance Spectrum (CDCl$_3$) δ ppm: 1.87 (3H, singlet); 3.21 (1H, doublet, J=9.9 Hz); 3.95 (1H, doublet, J=5.9 Hz); 6.07 & 7.99 (1H×2, each singlet).

EXAMPLE 147

13-{2-[4-(3-Pyrid-2'-ylcarbazoylamino)phenyl]ethoxy}milbemycin $A_4$

Nuclear Magnetic Resonance Spectrum ($CDCl_3$) δ ppm: 1.87 (3H, singlet); 3.21 (1H, doublet, J=9.9 Hz); 3.96 (1H, doublet, J=6.2 Hz); 6.38, 6.53 & 7.71 (1H×3, each singlet); 7.64 & 8.21 (1H×2, each singlet).

EXAMPLE 148

13-{2-[4-(3-Acetylcarbazoylamino)phenyl]ethoxy}milbemycin $A_4$

Nuclear Magnetic Resonance Spectrum ($CDCl_3$) δ ppm: 1.87 (3H, singlet); 1.99 (3H, singlet); 2.47 (1H, doublet, J=8.1 Hz); 3.20 (1H, doublet, J=9.5 Hz); 3.95 (1H, doublet, J=6.2 Hz); 7.90, 7.98 & 8.90 (1H×3, each singlet).

EXAMPLE 149

13-{2-[4-(3-Benzoylcarbazoylamino)phenyl]ethoxy}milbemycin $A_4$

Mass spectrum m/e: 677 ($M^+$–152).

Nuclear Magnetic Resonance Spectrum ($CDCl_3$) δ ppm: 1.86 (3H, singlet); 2.44 (1H, doublet, J=8.1 Hz): 3.20 (1H, doublet, J=9.9 Hz); 3.95 (1H, doublet, J=6.2 Hz); 7.99, 8.28 & 9.30 (1H×3, each singlet).

EXAMPLE 150

13-{2-[4-(3-o-Fluorophenylureido)phenyl]ethoxy milbemycin $A_4$ 0.020 ml of 4-fluorophenylisocyanate was added to a solution of 0.100 g of 13-[2-(4-aminophenyl)ethoxy] milbemycin $A_4$ (prepared by a similar procedure to that described in Example 35) in 2.0 ml of tetrahydrofuran, and then the mixture was stirred at room temperature for 20 minutes. At the end of this time, the reaction mixture was diluted with 15 ml of ethyl acetate, washed with water and dried over anhydrous sodium sulfate. The solvent was then removed by evaporation to dryness under reduced pressure, and the resulting residue was purified by column chromatography through silica gel (ODS treated), eluted with 80% v/v aqueous acetonitrile, to give 0.118 g of the title compound.

Mass spectrum m/e: 677 ($M^+$–137).

Nuclear Magnetic Resonance Spectrum ($CDCl_3$) δ ppm: 1.87 (3H, singlet); 3.21 (1H, doublet, J=9.9 Hz); 3.96 (1H, doublet, J=6.2 Hz); 6.5 & 6.58 (1H×2, singlet).

Following a similar procedure to that described in Example 150, the compounds of Examples 151 to 59 were obtained and had the properties shown below.

EXAMPLE 151

13-{2-[4-(3-Ethylureido)phenyl]ethoxy milbemycin $A_4$

Nuclear Magnetic Resonance Spectrum ($CDCl_3$) δ ppm: 1.87 (3H, singlet); 3.21 (1H, doublet, J=9.9 Hz); 3.96 (1H, doublet, J=6.2 Hz); 4.60 (1H, triplet, J=6.0 Hz); 6.14 (1H, singlet); 7.17 (4H, multiplet).

EXAMPLE 152

13-{2-[4-(3-Propylureido)phenyl]ethoxy milbemycin $A_4$

Mass spectrum m/e: 677 ($M^+$–85).

Nuclear Magnetic Resonance Spectrum ($CDCl_3$) δ ppm: 1.87 (3H, singlet); 3.21 (1H, doublet, J=9.9 Hz); 3.96 (1H, doublet, J=6.2 Hz); 6.16 (1H, singlet); 7.17 (4H, multiplet).

EXAMPLE 153

13-{2-[4-(3-2'-Chloroethylureido)phenyl]ethoxy milbemycin $A_4$

Mass spectrum m/e: 677 ($M^+$–105).

Nuclear Magnetic Resonance Spectrum ($CDCl_3$) δ ppm: 1.87 (3H, singlet); 3.21 (1H, doublet, J=9.9 Hz); 3.96 (1H, doublet, J=6.2 Hz); 5.14 (1H, triplet, J=5.5 Hz); 6.30 (1H, singlet); 7.19 (4H, multiplet),

EXAMPLE 154

13-{2-[4-(3-Allylureido)phenyl]ethoxy milbemycin $A_4$

Nuclear Magnetic Resonance Spectrum ($CDCl_3$) δ ppm: 1.87 (3H, singlet); 3.21 (1H, doublet, J=9.9 Hz); 3.86 (2H, multiplet); 3.96 (1H, doublet, J=6.2 Hz); 4.75 (1H, triplet, J=5.9 Hz); 5.13, 5.19 & 5.80 (1H×3, multiplet); 6.26 (1H, singlet).

EXAMPLE 155

13-{2-[4-(3-Propionylureido)phenyl]ethoxy milbemycin $A_4$

Mass spectrum m/e: 677 ($M^+$–99).

Nuclear Magnetic Resonance Spectrum ($CDCl_3$) δ ppm: 1.83 (3H, singlet); 2.44 (2H, quartet, J=7.3 Hz); 3.21 (1H, doublet, J=9.8 Hz); 3.96 (1H, doublet, J=6.3 Hz); 8.49 & 10.48 (1H×2, each singlet).

EXAMPLE 156

13-{2-[4-(3-Benzoylureido)phenyl]ethoxy milbemycin $A_4$

Mass spectrum m/e: 677 ($M^+$–147).

Nuclear Magnetic Resonance Spectrum ($CDCl_3$) δ ppm: 1.87 (3H, singlet); 3.22 (1H, doublet, J=9.8 Hz); 3.96 (1H, doublet, J=6.3 Hz); 9.05 & 10.79 (1H×2, each singlet).

EXAMPLE 157

13-{2-[4-(3-Methanesulfonylureido)phenyl]ethoxy milbemycin $A_4$

Mass spectrum m/e: 677 ($M^+$–121).

Nuclear Magnetic Resonance Spectrum ($CDCl_3$) δ ppm: 1.83 (3H, singlet); 3.21 (1H, doublet, J=9.5 Hz); 3.29 (3H, singlet); 3.95 (1H, doublet, J=6.2 Hz); 8.11 (1H, singlet).

EXAMPLE 158

13-{2-[4-3'-Methyl(thioureido)phenyl]milbemycin $A_4$

Mass spectrum m/e: 677 ($M^+$–73).

Nuclear Magnetic Resonance Spectrum ($CDCl_3$) δ ppm: 1.87 (3H, singlet); 3.13 (3H, doublet, J=4.8 Hz); 3.21 (1H, doublet, J=9.9 Hz); 3.96 (1H, doublet, J=6.2 Hz); 5.94 (1H, broad singlet); 7.57 (1H, singlet).

EXAMPLE 159

13-{2-[4-3'-Ethyl(thioureido)phenyl]ethoxy milbemycin $A_4$

Mass spectrum m/e: 677 ($M^+$–87).

Nuclear Magnetic Resonance Spectrum ($CDCl_3$) δ ppm: 1.87 (3H, singlet); 3.20 (1H, doublet, J=9.9 Hz); 3.65 (2H, multiplet); 3.95 (1H, doublet, J=6.2 Hz); 5.77 (1H, multiplet); 7.50 (1H, singlet).

EXAMPLE 160

13-[2-(4-Formimidoylaminophenyl)ethoxy]milbemycin $A_4$ 0.066 g of ethyl formimidate hydrochloride was added to a solution of 0.306 g of 13-[2-(4-aminophenyl)ethoxy] milbemycin $A_4$ (prepared by a similar procedure to that described in Example 64) in 2.0 ml of methanol, and then the mixture was stirred at room temperature for 30 minutes. At the end of this time, the solvent was removed by evaporation to dryness under reduced pressure, and the resulting residue was purified by column chromatography through silica gel (ODS treated), eluted with 55% v/v aqueous acetonitrile, to give 0.076 g of the title compound.

Mass spectrum m/e: 677 ($M^+-27$).

Nuclear Magnetic Resonance Spectrum (CDCl$_3$) δ ppm: 1.86 (3H, singlet); 3.19 (1H, doublet, J=9.5 Hz); 3.95 (1H, doublet, J=5.9 Hz); 8.25 (1H, singlet).

EXAMPLE 161

13-[2-(4-Benzimidoylaminophenyl)ethoxy]milbemycin A$_4$ 0.170 g of methyl thiobenzimidate hydroiodide was added to a solution of 0.306 g of 13-[2-(4-aminophenyl)ethoxy] milbemycin A$_4$ (prepared by a similar procedure to that described in Example 64) in 2.0 ml of methanol, and then the mixture was stirred at room temperature for 40 minutes. At the end of this time, the solvent was removed by evaporation to dryness under reduced pressure. The resulting residue was diluted with ethyl acetate and was washed, in turn, with a 4% v/v aqueous solution of sodium bicarbonate and with water, after which it was dried over anhydrous sodium sulfate. The solvent was then removed by evaporation to dryness under reduced pressure, and the resulting residue was purified by column chromatography through silica gel (ODS treated), eluded with 65% v/v aqueous acetonitrile, to give 0.310 g of the title compound.

Mass spectrum m/e: 780 ($M^+$, $C_{47}H_{60}N_2O_8$).

Nuclear Magnetic Resonance Spectrum (CDCl$_3$) δ ppm: 1.87 (3H, singlet); 3.21 (1H, doublet, J=9.5 Hz); 3.96 (1H, doublet, J=6.2 Hz); 7.83 (2H, broad singlet).

EXAMPLE 162

13-[2-[4-(3-Methoxycarbonylguanidino)phenyl]ethoxy milbemycin A$_4$ 0.041 g of N-methoxycarbonyl-S-methyisothiourea and two drops of acetic acid were added to a solution of 0.204 g of 13-[2-(4-aminophenyl)ethoxy]milbemycin A$_4$ (prepared by a similar procedure to that described in Example 64) in 2.0 ml of methanol, and then the mixture was stirred at room temperature for 1.5 hours. At the end of this time, the solvent was removed by evaporation to dryness under reduced pressure, and the resulting residue was purified by column chromatography through silica gel (ODS created), eluted with 55% v/v aqueous acetonitrile, to give 0.112 g of the title compound.

Mass spectrum m/e: 751 ($M^+-16$).

Nuclear Magnetic Resonance Spectrum (CDCl$_3$) δ ppm: 1.87 (3H, singlet); 3.21 (1H, doublet, J=9.9 Hz); 3.71 (3H, singlet); 3.96 (1H, doublet, J=6.2 Hz).

Following a similar procedure to that described in Example 162, the compound of Example 163 was obtained.

EXAMPLE 163

13-{2-[p-2,3-Bis(methoxycarbonyl)quanidinophenyl] ethoxymilbemycin A$_4$

Nuclear Magnetic Resonance Spectrum (CDCl$_3$) δ ppm: 1.87 (3H, singlet); 3.21 (1H, doublet, J=9.8 Hz); 3.73 & 3.86 (3H×2, singlet); 3.96 (1H, doublet, J=5.9 Hz); 10.17 & 11.88 (1H×2, singlet).

EXAMPLE 164

13-[2-(4-Benzenesulfinylaminophenyl)ethoxy]milbemycin A$_4$ 0.049 ml of pyridine and 0.107 g of benzenesulfinyl chloride were added to a solution of 0.340 g of 13-[2-(4-aminophenyl)ethoxy]milbemycin A$_4$ (prepared by a similar procedure to that described in Example 64) in 3.5 ml of 1,2-dichloroethane, and then the mixture was stirred at room temperature for 30 minutes. At the end of this time, the reaction mixture was diluted with ethyl acetate and washed, in turn, with 0.5N aqueous hydrochloric acid, with water, with a 4% v/v aqueous solution of sodium bicarbonate and with water, after which it was dried over anhydrous sodium sulfate. The solvent was then removed by evaporation to dryness under reduced pressure, and the resulting residue was purified by column chromatography through silica gel, eluted with a 55:45 by volume mixture of cyclohexane and ethyl acetate, to give 0.105 g of the title compound.

Mass spectrum m/e: 677 ($M^+-124$).

Nuclear Magnetic Resonance Spectrum (CDCl$_3$) δ ppm: 1.87 (3H, singlet); 3.21 (1H, doublet, J=9.9 Hz); 3.96 (1H, doublet, J=6.3 Hz); 5.96 (1H, singlet). 7.0–7.9 (9H, multiplet).

EXAMPLE 165

13-Deoxy-13-[2-(4-aminophenyl)ethoxy]-22,23-dihydroavermectin B$_1$a aglycone 1.460 g of 13-deoxy-13-[2-(4-nitrophenyl)ethoxy]-22,23-dihydroavermectin B$_1$a aglycone (which had been prepared by treating 22,23-dihydroavermectin B$_1$a aglycone by a similar procedure to those described in Preparation 1 and Example 32) was dissolved in 13.0 ml of 90% v/v aqueous acetic acid. 1.30 g of zinc powder was added, and then the mixture was stirred for 20 minutes whilst cooling with water. The reaction mixture was then worked up by a similar procedure to that described in Example 35 to give 1,143 g of the title compound.

Mass spectrum m/e: 705 ($M^+$, $C_{42}H_{59}NO_8$).

Nuclear Magnetic Resonance Spectrum (CDCl$_3$) δ ppm: 1.87 (3H, singlet); 3.21 (1H, doublet, J=9.8 Hz); 3.53 (2H, broad singlet); 3.96 (1H, doublet, J=6.3 Hz);

EXAMPLE 166

13-[2-(4-Aminophenyl)ethoxy]milbemycin D 1.630 g of 13-[2-(4-nitrophenyl)ethoxy]milbemycin D (which had been prepared by treating milbemycin D by similar procedures to those described in Preparation 1 and Example 32) was dissolved in 15.0 ml of 90% v/v aqueous acetic acid. 1.50 g of zinc powder was added, and then the mixture was stirred for 20 minutes, whilst cooling with water. The reaction mixture was then worked up using similar procedures to those described in Example 64 to give 1.130 g of the title compound.

Mass spectrum m/e: 691 ($M^+$, $C_{41}H_{57}NO_8$).

Nuclear Magnetic Resonance Spectrum (CDCl$_3$) δ ppm: 1.87 (3H, singlet); 3.21 (1H, doublet, J=9.8 Hz); 3.56 (2H, broad singlet); 3.96 (1H, doublet, J=5.9 Hz);

EXAMPLE 167

13-Deoxy-13-{2-[4-(3-methylureido)phenyl]ethoxy -22,23-dihydroavermectin B$_1$a aglycone 0.212 g of 13-deoxy-13-[2-(4-aminophenyl)ethoxy]-22, 23-dihydroavermectin B$_1$a aglycone (prepared as described in Example 165) was dissolved in 2.0 ml of 1,2-dichloroethane. 2 drops of methyl isocyanate were added, and then the mixture was stirred at room temperature for 2 hours. At the end of this time, the solvent was removed by evaporation to dryness under reduced pressure, and the resulting residue was purified by column chromatography through silica gel (ODS treated), eluted with 80% v/v aqueous acetonitrile, to give 0.218 g of the title compound.

Mass spectrum m/e: 705 ($M^+$–57).

Nuclear Magnetic Resonance Spectrum ($CDCl_3$) δ ppm: 1.87 (3H, singlet); 2.82 (3H, doublet, J=3.7 Hz); 3.21 (1H, doublet, J=9.5 Hz); 3.96 (1H, doublet, J=5.9 Hz); 6.28 (1H, singlet).

EXAMPLE 168

13-{2-[4-(3-Methylureido)phenyl]ethoxy milbemycin D 0.208 g of 13-[2-(4-aminophenyl)ethoxy]milbemycin D (prepared as described in Example 166) was treated by a similar procedure so that that described in Example 167 to give 0.216 g of the title compound.

Mass spectrum m/e: 691 ($M^+$–57).

Nuclear Magnetic Resonance Spectrum ($CDCl_3$) δ ppm: 1.87 (3H, singlet); 2.82 (3H, doublet, J=4.9 Hz); 3.21 (1H, doublet, J=9.8 Hz); 3.96 (1H, doublet, J=5.9 Hz); 6.27 (1H, singlet).

EXAMPLE 169

13-Deoxy-13-[2-(4-methanesulfonylaminophenyl)ethoxy]-22,23-dihydroavermectin $B_1$a aglycone 0.212 g of 13-deoxy-13-[2-(4-aminophenyl)ethoxy]-22,23-dihydroavermectin $B_1$a aglycone (prepared as described in Example 165) was dissolved in 2.0 ml of 1,2-dichloroethane. 0.032 ml of pyridine and 0.046 g of methanesulfonyl chloride were added to the resulting solution, and then the mixture was stirred at room temperature for 2.5 hours. At the end of this time, the reaction mixture was diluted with 15 ml of ethyl acetate and washed, in turn, with 0.1N aqueous hydrochloric acid, with water, with a 4% v/v aqueous solution of sodium bicarbonate and with water, after which it was dried over anhydrous sodium sulfate. The solvent was then removed by evaporation to dryness under reduced pressure, and the resulting residue was purified by column chromatography through silica gel (ODS created), eluted with 80% v/v aqueous acetonitrile, to give 0.221 g of the title compound.

Mass spectrum m/e: 783 ($M^+$, $C_{43}H_{61}NO_{10}S$).

Nuclear Magnetic Resonance Spectrum ($CDCl_3$) δ ppm: 1.87 (3H, singlet); 2.93 (3H, singlet); 3.20 (1H, doublet, J=9.5 Hz); 3.96 (1H, doublet, J=6.3 Hz); 6.37 (1H, singlet).

EXAMPLE 170

13-[2-(4-Methanesulfonylaminophenyl)ethoxy]milbemycin D 0.208 g of 13-[2-(4-aminophenyl)ethoxy]milbemycin D (prepared as described in Example 166) was treated by a similar procedure to that described in Example 140 to give 0.219 g of the title compound.

Mass spectrum m/e: 769 ($M^+$, $C_{42}H_{59}NO_{10}S$).

Nuclear Magnetic Resonance Spectrum ($CDCl_3$) δ ppm: 1.87 (3H, singlet); 2.97 (3H, singlet); 3.21 (1H, doublet, J=9.8 Hz); 3.96 (1H, doublet, J=5.9 Hz); 6.39 (1H, singlet).

EXAMPLE 171

13-Deoxy-13-[2-(4-ethoxycarbonylaminophenyl)ethoxy]-22,23-dihydroavermectin $B_1$a aglycone 0.212 g of 13-deoxy-13-[2-(4-aminophenyl)ethoxy]-22,23-dihydroavermectin $B_1$a aglycone (prepared as described in Example 165) was dissolved in 2.0 ml of 1,2-dichloroethane. 0.032 ml of pyridine and 0.060 g of ethyl chlorocarbonate were added to the resulting solution, whilst ice-cooling, and then the mixture was stirred for 30 minutes. At the end of this time, the reaction mixture was diluted with 15 ml of ethyl acetate and washed, in turn, with 0.5N aqueous hydrochloric acid, with water, with a 4% v/v aqueous solution of sodium bicarbonate and again with water, after which it was dried over anhydrous sodium sulfate. The solvent was then removed by evaporation to dryness under reduced pressure, and the resulting residue was purified by column chromatography through silica gel (ODS treated), eluted with 80% v/v aqueous acetonitrile, to give 0.168 g of the title compound.

Mass spectrum m/e: 778 ($M^+$+1).

Nuclear Magnetic Resonance Spectrum ($CDCl_3$) δ ppm: 1.87 (3H, singlet); 3.21 (1H, doublet, J=9.5 Hz); 3.96 (1H, doublet, J=5.9 Hz); 4.22 (2H, quartet, J=7.3 Hz).

EXAMPLE 172

13-[2-(4-Ethoxycarbonylaminophenyl)ethoxy]milbemycin D 0.208 g of 13-[2-(4-aminophenyl)ethoxy]milbemycin D (prepared as described in Example 166) was treated by a similar procedure to that described in Example 171 to give 0.167 g of the title compound.

Mass spectrum m/e: 745 ($M^+$–18).

Nuclear Magnetic Resonance Spectrum ($CDCl_3$) δ ppm: 1.87 (3H, singlet); 3.21 (1H, doublet, J=9.8 Hz); 3.96 (1H, doublet, J=6.3 Hz); 4.21 (2H, quartet, J=7.0 Hz); 6.52 (1H, singlet).

EXAMPLE 173

13-[2-(N-Ethoxycarbonyl-N-methyl-4-aminophenyl)ethoxy]milbemycin $A_4$ 0.682 g of N-ethoxycarbonyl-N-methyl-4-aminophenethyl alcohol and 0.300 g of mercuric iodide were added to a solution of 0.325 g of 13-iodo-5-oxomilbemycin $A_4$ in 5 ml of 1,2-dichloroethane, and then the mixture was stirred at room temperature for 2.5 hours. At the end of this time, the reaction mixture was worked up by a similar procedure to that described in Example 32 to give 0.138 g of the title compound.

Mass spectrum m/e: 763 ($M^+$, $C_{44}H_{61}NO_{10}$).

Nuclear Magnetic Resonance Spectrum ($CDCl_3$) δ ppm: 1.87 (3H, singlet); 3.21 (1H, doublet, J=9.9 Hz); 3.27 (3H, singlet); 3.95 (1H, doublet, J=6.2 Hz); 4.15 (2H, quartet, J=7.0 Hz).

EXAMPLE 174

13-{2-[4-(3-Methylureidomethyl)phenyl]ethoxy milbemycin $A_4$

Step 1

4.900 g of 4-(2,2,2-trichloroethoxycarbonylaminomethyl) phenethyl alcohol and 2.060 g of mercuric iodide were added to a solution of 2.000 g of 13-iodo-5-oxomilbemycin $A_4$ in 10 ml of 1,2-dichloroethane, and then the mixture was stirred at room temperature for 2.5 hours. At the end of this time, the reaction mixture was worked up by a similar procedure to that described in Example 32 to give 1.610 g of 13-{2-[4-(2,2,2-trichloroethoxycarobonylaminomethyl) phenyl]ethoxy}milbemycin $A_4$ Step 2

All of the product obtained in Step 1 was dissolved in 15.0 ml of 90% v/v aqueous acetic acid, 2.0 g of zinc powder were added, and then the mixture was stirred for 60 minutes whilst cooling with water. The mixture was then diluted with 50 ml of ethyl acetate and the insoluble matter was filtered off. The filtrate was washed with a saturated aqueous solution of sodium chloride and dried over anhydrous sodium sulfate. The solvent was removed by evaporation under reduced pressured, and the resulting residue was purified by column chromatography through silica gel (ODS treated), eluted with 65% v/v aqueous acetonitrile. The eluate was concentrated by evaporation under reduced pressure, and dissolved in 20 ml of ethyl acetate. The resulting solution was then washed, in turn, with a 4% v/v aqueous solution of sodium bicarbonate and with water, after which the solvent was removed by evaporation under reduced pressure to give 0.738 g of 13-{2-[4-(aminomethyl)phenyl]ethoxy milbemycin $A_4$.

Step 3

0.138 g of the product obtained in Step 2 was dissolved in 1.5 ml of 1,2-dichloroethane. 2 drops of methyl isocyanate were added, and then the mixture was stirred at room temperature for 30 minutes. The solvent was then removed by evaporation to dryness under reduced pressure, and the resulting residue was purified by column chromatography through silica gel (ODS treated), eluted with 80% v/v aqueous acetonitrile, to give 0.143 g of the title compound.

Mass spectrum m/e: 731 ($M^+$−17).

Nuclear Magnetic Resonance Spectrum (CDCl$_3$) δ ppm: 1.87 (3H, singlet); 2.77 (3H, doublet, J=4.8 Hz); 3.21 (1H, doublet, J=9.9 Hz); 3.95 (1H, doublet, J=6.2 Hz); 4.33 (2H, doublet, J=4.9 Hz); 4.68 (1H, doublet, J=4.9 Hz).

EXAMPLE 175

13-{2-[4-(Ethoxycarbonylaminomethyl)phenyl] ethoxymilbemycin $A_4$ 0.138 g of 13-{2-[4-(aminomethyl)phenyl] ethoxymilbemycin $A_4$ (obtained as described in Step 2 of Example 145) was treated by a similar procedure to that described in Example 171 to give 0.082 g of the title compound.

Mass spectrum m/e: 763 ($M^+$, $C_{44}H_{61}NO_{10}$).

Nuclear Magnetic Resonance Spectrum (CDCl$_3$) δ ppm: 1.87 (3H, singlet); 3.21 (1H, doublet, J=9.9 Hz); 3.95 (1H, doublet, J=6.2 Hz); 4.15 (2H, quartet, J=7.0 Hz); 4.33 (2H, doublet, J=5.9 Hz); 4.89 (1H, broad singlet).

EXAMPLE 176

13-{2-[4-(Methanesulfonylaminomethyl)phenyl] ethoxymilbemycin $A_4$ 0.138 g of 13-{2-[4-(aminomethyl)phenyl] ethoxymilbemycin $A_4$ (obtained as described in Step 2 of Example 174) was treated by a similar procedure to that described in Example 169 to give 0.105 g of the title compound.

Mass spectrum m/e: 769 ($M^+$, $C_{42}H_{59}NO_{10}S$).

Nuclear Magnetic Resonance Spectrum (CDCl$_3$) δ ppm: 1.87 (3H, singlet); 2.87 (3H, singlet); 3.21 (1H, doublet, J=9.9 Hz); 3.95 (1H, doublet, J=6.2 Hz); 4.29 (2H, doublet, J=5.9 Hz); 4.54 (1H, triplet, J=5.9 Hz).

EXAMPLE 177

13-{2-[4-(N-p-methylphenylcarbamoyl)phenyl] ethoxymilbemycin $A_4$ 0.510 g of 4-[N-(4-methylphenyl)carbamoyl]phenethyl alcohol, 0.300 g of mercuric iodide and 0.120 ml of 2,6-lutidine were added to a solution of 0.335 g of 13-iodo-5-oxomilbemycin $A_4$ in 5.0 ml of 1,2-dichloroethane, and then the mixture was stirred at 30° C. for 3.5 hours. At the end of this time, the reaction mixture was worked up by a similar procedure to that described in Example 32 to give 0.115 g of the title compound.

Mass spectrum m/e: 777 ($M^+$−18).

Nuclear Magnetic Resonance Spectrum (CDCl$_3$) δ ppm: 1.87 (3H, singlet); 2.34 (3H, singlet); 3.21 (1H, doublet, J=9.5 Hz); 3.95 (1H, doublet, J=6.2 Hz); 7.72 (1H, singlet).

EXAMPLE 178

13-[2-(4-Methanesulfonylaminophenyl)ethoxy]milbemycin $A_4$ 5-oxime

Step 1

0.714 g of 13-[2-(4-methanesulfonylaminophenyl) ethoxy]milbemycin $A_4$ (prepared as described in Example 75) was dissolved in 5.0 ml of methylene chloride. 1.90 g of manganese dioxide was added to the resulting solution, whilst ice-cooling, and then the mixture was stirred for 3.5 hours. At the end of this time, the reaction mixture was filtered using a Celite (trade name) filter aid, and then the filtrate was concentrated under reduced pressure to dryness, to give 0.672 g of 5-oxo-13-[2-(4-methanesulfonylaminophenyl)ethoxy]milbemycin $A_4$.

Step 2

0.226 g of the product obtained in Step 1 was dissolved in 2.4 ml of methanol. 1.2 ml of water, 2.4 ml of dioxane and 0.220 g of hydroxylamine hydrochloride were added to the resulting solution, and then the mixture was stirred at 40° C. for 2.5 hours. The reaction mixture was then diluted with 20 ml of ethyl acetate, washed twice with water and dried over anhydrous sodium sulfate. The solvent was then removed by evaporation under reduced pressure, and the resulting residue was purified by column chromatography through silica gel (ODS treated), eluted with 80% v/v aqueous acetonitrile, to give 0.196 g of the title compound.

Mass spectrum m/e: 735 ($M^+$−33).

Nuclear Magnetic Resonance Spectrum (CDCl$_3$) δ ppm: 1.93 (3H, singlet); 2.97 (3H, singlet); 3.21 (1H, doublet, J=9.9 Hz); 4.66 (1H, singlet); 6.35 (1H, singlet); 8.05 (1H, singlet).

PREPARATION 1

5-Oxo-13-iodomilbemycin $A_4$ (III)

6.00 g of 2-chloroformyl-1,2,4-triazolo[4,3a]pyridin-3-one and 2.42 ml of pyridine were added, whilst ice-cooling, to a solution of 16.60 g of 5-oxo-13-hydroxymilbemycin $A_4$ in 75 ml of methylene chloride, and the mixture was stirred for 30 minutes. At the end of this time, the reaction mixture was filtered and the filtrate was washed with a 0.5M aqueous solution of citric acid, with water, with a 4% v/v aqueous solution of sodium bicarbonate and again with water, in that order. The solution was then dried over anhydrous sodium sulfate, after which the solvent was removed by distillation to dryness under reduced pressure. The residue was dissolved in 300 ml of 1,2-dichloroethane, and 51.4 g of zinc iodide were added to the solution. The mixture was then stirred at room temperature for 25 minutes. At the end of this time, the excess of zinc iodide was removed by filtration and the filtrate was washed with a 10% v/v aqueous solution of sodium thiosulfate and with water, in that order. The solution was then dried over anhydrous sodium sulfate and the solvent was removed by distillation to dryness under reduced pressure. The residue was purified by column chromatography through 300 g of silica gel, eluded with a 9:1 by volume mixture of methylene chloride and hexane, and the eluate was crystallized with a mixture of diethyl ether and hexane to afford 15.3 g of the title compound.

Nuclear Magnetic Resonance Spectrum (CDCl$_3$) δ ppm: 3.85 (1H, singlet); 3.99 (1H, singlet); 4.58 (1H, doublet, J=11.0 Hz).

TEST EXAMPLES

The anthelmintic activity against *Nippostongylus brasiliensis*, a nematode parasitic to rats, was examined with groups each containing 3 Wistar strain rats of body weight in the range from 40 to 60 g.

The rats were infested percutaneously with about 100 larvae of the nematode for each rat. Solutions containing the test compound at various concentrations were administered orally 3 days after infection. Each solution was prepared by dissolving 1.0 mg of the test compound in 0.1 ml of dimethylformamide, and then adding 10 ml of polyethylene glycol (PEG 400) to the solution. The solution was then adjusted by the addition of PEG 400 to achieve a concentration of 0.250 or 0.125 mg/kg.

The rats were killed 4 days after infection, and the number of parasites in the small intestine was counted. The results obtained are summarized in Tables 1 and 2.

In Tables 1 and 2, the anthelmintic activity was calculated by the following formula:

Anthelmintic activity (%) =

$$100 \times \frac{\text{Number of parasites in untreated group} - \text{Number of parasites in treated group}}{\text{Number of parasites in untreated infected group}}$$

TABLE 1

Effect of the compounds administered orally

| | | Anthelmintic activity (%)* | |
|---|---|---|---|
| | | 0.250** | 0.125** |
| 1) | Compound of Example 7 | — | 87.8 |
| 2) | Compound of Example 8 | — | 69.1 |
| 3) | Compound of Example 13 | — | 76.1 |
| 4) | Compound of Example 14 | — | 91.6 |
| 5) | Compound of Example 15 | — | 88.1 |
| 6) | Compound of Example 18 | — | 88.7 |
| 7) | Compound of Example 20 | — | 76.9 |
| 8) | Compound of Example 21 | — | 83.2 |
| 9) | Compound of Example 22 | — | 98.3 |
| 10) | Compound of Example 23 | — | 83.1 |
| 11) | Compound of Example 25 | — | 99.3 |
| 12) | Compound of Example 26 | — | 99.8 |
| 13) | Compound of Example 27 | — | 100.0 |
| 14) | Compound of Example 28 | — | 99.0 |
| 15) | 13-Methoxy-milbemycin A$_4$*** | 44.0 | 49.5 |
| 16) | Milbemycin A$_4$ | 24.8 | — |

**Dose: mg/kg
Compound disclosed in U.S. Pat. No. 4,696,945.

$$\text{Mortality rate (\%)} = \frac{\text{Number of parasites in untreated group} - \text{Number of parasites in treated group}}{\text{Number of parasites in untreated group}}$$

TABLE 2

Activity on Oral Administration

| Cpd. of Example | Mortality rate (%) | |
|---|---|---|
| No. | 0.250 mg/kg | 0.125 mg/kg |
| 30 | 73.5 | 44.3 |
| 36 | 98.4 | 81.6 |
| 38 | 98.6 | 98.1 |
| 64 | 98.5 | 92.3 |
| 67 | 99.8 | 99.8 |
| 68 | 96.7 | 68.1 |
| 71 | 99.6 | 99.6 |
| 75 | 99.7 | 100 |
| 76 | 100 | 50.7 |
| 77 | 99.5 | 100 |
| 78 | 100 | 98.6 |
| 79 | 99.5 | 98.2 |
| 86 | 99.8 | 99.4 |
| 90 | — | 99.1 |
| 93 | — | 92.8 |
| 100 | — | 100 |
| 110 | — | 99.7 |
| 113 | — | 100 |
| 115 | 99.5 | 94.4 |
| 116 | — | 100 |
| 117 | — | 97.4 |
| 138 | — | 98.9 |
| 140 | — | 93.5 |
| 143 | — | 100 |
| 146 | — | 97.9 |
| 155 | — | 95.9 |
| 158 | — | 100 |
| 160 | — | 97.6 |
| 161 | 89.5 | 77.0 |
| 163 | 98.6 | 92.7 |
| 169 | — | 93.2 |
| 170 | 99.8 | 98.7 |
| 174 | — | 99.2 |
| 13-Methoxymilbemycin A$_4$* | 44.0 | 49.5 |
| Milbemycin A$_4$ | 24.8 | — |

*Compound disclosed in U.S. Pat. No. 4,696,945.

In the above Tables 1 and 2, a dash means that the compound was not tested at the particular concentration.

We claim:

1. A compound of formula (I):

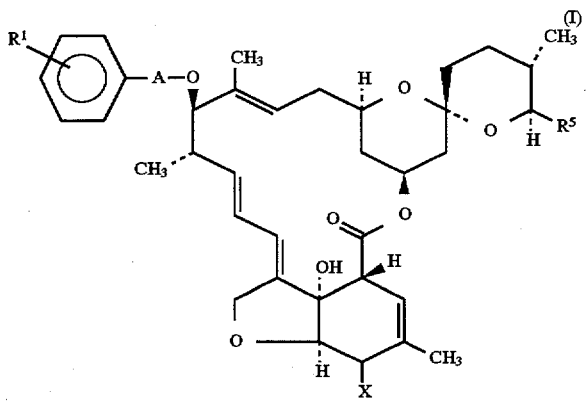

in which:

R$^1$ represents: a hydrogen atom; a halogen atom; a cyano group; a nitro group; an alkyl group which has from 1 to 4 carbon atoms and which is unsubstituted or has at least one substituent selected from the group consisting of substituents (a); an alkoxy group having from 1 to 4 carbon atoms; an alkoxyalkoxy group having a total of from 2 to 6 carbon atoms; or a group having one of the following formulae:

—(CH$_2$)$_n$NHR$^9$

—(CH$_2$)$_n$NR$^9$COR$^6$

—(CH$_2$)$_n$NR$^9$COCOR$^6$

—(CH$_2$)$_n$NR$^9$COCOR$^7$

—(CH$_2$)$_n$NR$^9$CHR$^6$NHCOR$^6$

—(CH$_2$)$_n$NR$^9$CHR$^6$NHCONHR$^6$

—(CH$_2$)$_n$NR$^9$CHR$^6$NHCOOR$^7$

—(CH$_2$)$_n$NR$^9$C(=Y)YR$^6$

—(CH$_2$)$_n$NR$^9$C(=Y)NR$^6$R$^6$

—(CH$_2$)$_n$NR$^9$C(=Y)NR$^6$NR$^6$R$^6$

—(CH$_2$)$_n$NR$^9$C(=Y)NR$^6$NHZ

—(CH$_2$)$_n$NR$^9$C(=NR$^{11}$)NHR$^{11}$

—(CH$_2$)$_n$NR$^9$C(=NR$^{11}$)R$^6$

—(CH$_2$)$_n$NR$^9$SO$_m$R$^6$

—CONHR$^6$ or

—COOR$^7$ wherein:

m is 1 or 2;

n is 0, 1 or 2;

R$^6$ represents a hydrogen atom; an alkyl group having from 1 to 8 carbon atoms; a substituted alkyl group having from 1 to 8 carbon atoms and having at least one substituent selected from the group consisting of substituents (b); an aliphatic hydrocarbon group having from 2 to 8 carbon atoms and having one or two carbon-carbon double or triple bonds; a cycloalkyl group having from 2 to 8 carbon atoms; a substituted cycloalkyl group having from 2 to 8 carbon atoms and having at least one substituent selected from the group consisting of substituents (c); an aryl group which has from 6 to 14 ring carbon atoms and which is unsubstituted or which has at least one substituent selected from the group consisting of substituents (c); an aryloxy group which has from 6 to 14 ring carbon atoms and which is unsubstituted or which has at least one substituent selected from the group consisting of substituents (c); an arylthio group which has from 6 to 14 ring carbon atoms and which is unsubstituted or which has at least one substituent selected from the group consisting of substituents (c); or a heterocyclic group selected from the group consisting of oxiranyl, oxetanyl, aziridinyl, azetidinyl, thiranyl, thietanyl, furyl, thienyl, pyrrolyl, pyridyl, thiazolyl, isothiazolyl, oxazolyl, isoxazolyl, imidazolyl, pyrazolyl, pyranyl, pyrazinyl, piperidinyl, pyridazinyl, pyrimidinyl, benzofuranyl, isobenzofuranyl, benzothienyl, isobenzothienyl, indolyl, quinolyl, isoquinolyl, quinazolinyl, quinoxalinyl, naphthyridynyl, xanthenyl, tetrahydrofuranyl, tetrahydrothienyl, pyrrolidinyl, thiazolidinyl, imidazolidinyl, imidazolinyl, oxazolinyl, oxazolidinyl, pyrazolidinyl, piperazyl, tetrahydropyrimidinyl, dihydropyridazinyl, morpholinyl, thiomorpholinyl, indolinyl, tetrahydroquinolyl, pyrrolidonyl, piperidonyl, pyridonyl, thianthrenyl, chromenyl, phenoxathiinyl, 2H-pyrrolyl, isoindolyl, 3H-indolyl, indazolyl, phthalazinyl, quinoxalinyl, quinazolinyl, cinnolinyl, carbazolyl, phenanthridinyl, acridinyl, perimidinyl, phenazinylphenothiazinyl, furazanyl, phenoxazinyl, isochromanyl, chromanyl, pyrazolinyl, indolinyl and isoindolinyl, said heterocyclic group being unsubstituted or having at least one substituent selected from the group consisting of substituents (c); and, where there are two or more groups or atoms represented by R$^6$, the R$^6$ groups are the same or different from each other; or, where two groups represented by R$^6$ are attached to a single nitrogen atom, the R$^6$ groups, together with aa nitrogen atom to which they are attached, may be fused to form a heterocyclic ring selected from the group consisting of aziridinyl, azetidinyl, pyrrolyl, imidazolyl, pyrazolyl, pyrrolidinyl, thiazolidinyl, imidazolidinyl, imidazolonyl, oxazolinyl, oxazolidinyl, pyrazolidinyl, piperazyl, tetrahydropyrimidinyl, dihydropyridazinyl, pyrrolidonyl, piperidonyl, pyridonyl, pyrazolinyl, azepinyl, perhydroazepinyl, oxazepinyl and thiazepinyl; or, where two groups represented by R$^6$ are attached to an adjacent nitrogen atom, the R$^6$ groups, together with a nitrogen atom to which they are attached, may be fused to form a heterocyclic ring selected from the group consisting of diaziridine, diazete, diazetidine, pyrazolidine, pyrazoline, 1,2-dihydropyridazine, 1,2,3,4-tetrahydropyridazine, 1,2,5,6-tetrahydropyridazine, perhydropyridazine, 1,2-dihydro-1,2-diazepine and perhydro-1,2-diazepine which additionally contains 0 or 1 further hetero-atom selected from the group consisting of oxygen, nitrogen and sulfur atoms, in addition to said nitrogen atom;

R$^7$ represents an alkyl group having from 1 to 4 carbon atoms, a cycloalkyl group having from 3 to 7 carbon atoms, or an aralkyl group in which an alkyl group having from 1 to 4 carbon atoms is substituted by from 1 to 3 aryl groups which have from 6 to 10 ring carbon atoms and which have at least one substituent selected from the group consisting of substituents (c);

R$^9$ represents a hydrogen atom or an alkyl group having from 1 to 4 carbon atoms;

R$^{11}$ represents any of the groups or atoms defined above for R$^6$, or it represents a cyano group, a nitro group, a group of formula —COOR$^7$ wherein R$^7$ is as defined above, or a group of formula —COR$^6$ wherein R$^6$ is as defined above;

Y represents an oxygen atom or a sulfur atom; and, where there are two or more groups represented by Y, these are the same or different from each other;

Z represents a group of formula —COOR$^7$ wherein R$^7$ is as defined above, a group of formula —COR$^6$ wherein R$^6$ is as defined above or a group of formula —SO$_2$R$^6$ wherein R$^6$ is as defined above;

A represents a group having one of the following formulae:

—CHR$^2$—CHR$^3$—CHR$^4$—

—CR$^2$=CR$^3$—CHR$^4$— or

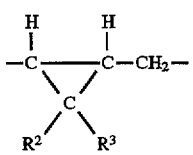

wherein $R^2$, and $R^3$ and $R^4$ are independently selected from the group consisting of hydrogen atoms, halogen atoms, alkyl groups having from 1 to 4 carbon atoms, and alkoxy groups having from 1 to 4 carbon atoms;

$R^5$ represents a methyl group, an ethyl group, an isopropyl group or a sec-butyl group; and X represents: a hydroxy group; an alkanoyloxy group which has from 1 to 5 carbon atoms, and which is unsubstituted or has at least one substituent selected from the group consisting of substituents (d); or a hydroxyimino group;

substituents (a):

halogen atoms, alkoxy groups having from 1 to 4 carbon atoms, alkythio groups having from 1 to 4 carbon atoms, and alkanoyloxy groups having from 1 to 5 carbon atoms;

substituents (b):

cycloalkyl groups having from 3 to 8 carbon atoms; alkoxy groups having from 1 to 4 carbon atoms; alkylthio groups having from 1 to 4 carbon atoms; cyanoalkylthio groups having from 2 to 5 carbon atoms; alkoxycarbonyl groups having from 2 to 5 carbon atoms; halogen atoms; cyano groups; nitro groups; amino groups; aryl groups which have from 6 to 14 ring carbon atoms and which are unsubstituted or have at least one substituent selected from the group consisting of substituents (c); aromatic heterocyclic groups which have 5 or 6 ring atoms and which are unsubstituted or which have at least one substituent selected from the group consisting of substituents (c) and such heterocyclic groups which are fused to one or two benzene or monocyclic aromatic heterocylic rings, said monocylic aromatic heterocyclic ring having 5 or 6 ring atoms of which from 1 to 3 are hetero-atoms selected from the group consisting of nitrogen, oxygen and sulfur hetero-atoms, to form a bicyclic or tricyclic group; aryloxy groups which have from 6 to 14 ring carbon atoms and which are unsubstituted or have at least one substituent selected from the group consisting of substituents (c); and arylthio groups which have from 6 to 14 ring carbon atoms and which are unsubstituted or have at least one substituent selected from the group consisting of substituents (c);

substituents (c):

alkyl groups having from 1 to 4 carbon atoms, alkoxy groups having from 1 to 4 carbon atoms, alkythio groups having from 1 to 4 carbon atoms, alkanoyloxy groups having from 1 to 5 carbon atoms, alkoxycarbonyl groups having from 2 to 5 carbon atoms, halogen atoms, cyano groups, nitro groups, amino groups, alkylamino groups in which the alkyl part has from 1 to 4 carbon atoms, dialkylamino groups in which each alkyl part is independently selected from the group consisting of alkyl groups having from 1 to 4 carbon atoms, carbamoyl groups, alkylcarbamoyl groups in which the alkyl part has from 1 to 4 carbon atoms, dialkylcarbamoyl groups in which each alkyl part is independently selected from the group consisting of alkyl groups having from 1 to 4 carbon atoms, and alkanoylamino groups having from 1 to 5 carbon atoms;

substituents (d):

halogen atoms, alkoxy groups having from 1 to 4 carbon atoms, alkoxycarbonyl groups having from 2 to 5 carbon atoms, and carboxy groups;

and salts and esters thereof.

2. The compound of claim 1, wherein $R^1$ represents: a hydrogen atom, an alkyl group having from 1 to 3 carbon atoms; an alkoxy group having from 1 to 3 carbon atoms; the fluorine or chlorine atoms; or the nitro or amino groups.

3. The compound of claim 1, wherein $R^1$ represents a group of formula $-NR^{9a}COR^{6a}$ wherein:

$R^{9a}$ represents a hydrogen atom or a methyl group; and $R^{6a}$ represents: a hydrogen atom; an alkyl group having from 1 to 4 carbon atoms; a cycloalkyl group having from 3 to 5 carbon atoms; an alkyl group having from 1 to 3 carbon atoms, and substituted with a halogen atom, a cyano group, an alkoxy group having from 1 to 3 carbon atoms, an alkylthio group having from 1 to 3 carbon atoms, a cyanomethylthio group or a phenoxy group; an alkenyl group having from 2 to 4 carbon atoms; a phenyl group; a phenyl group substituted with an alkyl group having from 1 to 3 carbon atoms, an alkoxy group having from 1 to 3 carbon atoms, a halogen atom or a nitro group; a pyridyl group; a pyrimidyl group; a pyrazinyl group; a furyl group; or a thienyl group.

4. The compound of claim 1, wherein $R^1$ represents a group of formula $-NR^{9a}COCOR^{6b}$ wherein:

$R^{9a}$ represents a hydrogen atom or a methyl group; and $R^{6b}$ represents: a hydrogen atom; an alkyl group having from 1 to 4 carbon atoms; a cycloalkyl group having from 3 to 5 carbon atoms; an alkenyl group having from 2 to 4 carbon atoms; a phenyl group; or a phenyl group substituted with an alkyl group having from 1 to 3 carbon atoms, an alkoxy group having from 1 to 3 carbon atoms, a halogen atom or a nitro group.

5. The compound of claim 1, wherein $R^1$ represents a group of formula $-NR^{9a}C(=Y)YR^{6c}$ wherein:

$R^{9a}$ represents a hydrogen atom or a methyl group;

Y represents an oxygen atom; and $R^{6c}$ represents: an alkyl group having from 1 to 4 carbon atoms; an alkyl group having from 1 to 4 carbon atoms, and substituted with a halogen atom or an alkoxy group having from 1 to 3 carbon atoms; a vinyl group; an allyl group; a benzyl group; a methoxybenzyl group; nitrobenzyl group; a furfuryl group; a thenyl group; or a phenyl group.

6. The compound of claim 1, wherein $R^1$ represents a group of formula $-NR^{9a}C(=Y)NR^{6d}R^{6e}$ wherein:

$R^{9a}$ represents a hydrogen atom or a methyl group;

Y represents an oxygen atom or a sulfur atom; and $R^{6d}$ and $R^{6e}$ are independently selected from the group consisting of: hydrogen atoms; alkyl groups having from 1 to 4 carbon atoms; cycloalkyl groups having from 3 to 6 carbon atoms; phenyl groups; and phenyl groups substituted with an alkyl group having from 1 to 3 carbon atoms, an alkoxy group having from 1 to 3 carbon atoms, a halogen atom or a nitro group; or $R^{6d}$ and $R^{6e}$, together with the nitrogen atom to which they are attached, form a piperidine, piperazine, morpholine, pyrrolidine, or aziridine ring.

7. The compound of claim 1, wherein $R^1$ represents a group of formula —$NR^{9a}C(=Y)NR^{6f}NR^{6g}R^{6h}$
wherein:

$R^{9a}$ represents a hydrogen atom or a methyl group;

Y represents an oxygen atom or a sulfur atom; and $R^{6f}$, $R^{6g}$ and $R^{6h}$ are independently selected from the group consisting of: hydrogen atoms; alkyl groups having from 1 to 4 carbon atoms; cycloalkyl groups having from 3 to 6 carbon atoms; phenyl groups; and phenyl groups substituted with an alkyl group having from 1 to 3 carbon atoms, an alkoxy group having from 1 to 3 carbon atoms, a halogen atom or a nitro group; or $R^{6g}$ and $R^{6h}$, together with the nitrogen atom to which they are attached, form a piperidine, piperazine, morpholine, pyrrolidine or aziridine ring; or $R^{6f}$ and $R^{6g}$, together with the nitrogen atoms to which they are attached, form a pyrazolidine or tetrahydropyridazine ring.

8. The compound of claim 1, wherein $R^1$ represents a group of formula —$NR^{9a}C(=Y)NR^{6j}NHZ$
wherein:

$R^{9a}$ represents a hydrogen atom or a methyl group;

Y represents an oxygen atom or a sulfur atom;

$R^{6j}$ represents an alkyl group having from 1 to 4 carbon atoms; or a cycloalkyl group having from 3 to 6 carbon atoms;

Z represents a group of formula —$COOR^{7a}$ wherein: R7a represents an alkyl group having from 1 to 4 carbon atoms, a cycloalkyl group having from 3 to 6 carbon atoms or a benzyl group; a group of formula —$COR^{6k}$ wherein $R^{6k}$ represents: an alkyl group having from 1 to 4 carbon atoms; a cycloalkyl group having from 3 to 6 carbon atoms a phenyl group; or a phenyl group substituted with an alkyl group having from 1 to 3 carbon atoms, an alkoxy group having from 1 to 3 carbon atoms, a halogen atom or a nitro group, or a group of formula —$SO_2R^{6m}$ wherein $R^{6m}$ represents: an alkyl group having from 1 to 4 carbon atoms; a phenyl group; or a phenyl group substituted with an alkyl group having from 1 to 3 carbon atoms, an alkoxy group having from 1 to 3 carbon atoms, a halogen atom or a nitro group.

9. The compound of claim 1, wherein $R^1$ represents a group of formula —$NR^{9a}C(=NR^{11a})NHR^{11b}$
wherein:

$R^{9a}$ represents a hydrogen atom or a methyl group;

$R^{11a}$ and $R^{11b}$ are independently selected from the group consisting of: hydrogen atoms; alkyl groups having from 1 to 4 carbon atoms; phenyl groups; phenyl groups substituted with an alkyl group having from 1 to 3 carbon atoms, an alkoxy group having from 1 to 3 carbon atoms, a halogen atom or a nitro group; groups of formula —$COOR^{7b}$ wherein $R^{7b}$ represents: an alkyl group having from 1 to 4 carbon atoms; a cycloalkyl group having from 3 to 6 carbon atoms; or a benzyl group; groups of formula —$COR^{6n}$ wherein $R^{6n}$ represents: an alkyl group having from 1 to 4 carbon atoms; a cycloalkyl group having from 3 to 6 carbon atoms; a phenyl group; or a phenyl group substituted with an alkyl group having from 1 to 3 carbon atoms, an alkoxy group having from 1 to 3 carbon atoms, a halogen atom or a nitro group.

10. The compound of claim 1, wherein $R^1$ represents a group of formula —$NR^{9a}C(=NR^{11c})R^{6p}$ wherein:

$R^{9a}$ represents a hydrogen atom or a methyl group;

$R^{11c}$ represents: a hydrogen atom; an alkyl group having from 1 to 4 carbon atoms; a phenyl group; a phenyl group substituted with an alkyl group having from 1 to 3 carbon atoms, an alkoxy group having from 1 to 3 carbon atoms, a halogen atom or a nitro group; a group of formula —$COOR^{7c}$ wherein $R^{7c}$ represents: an alkyl group having from 1 to 4 carbon atoms; a cycloalkyl group having from 3 to 6 carbon atoms; or a benzyl group; a group of formula —$COR^{6q}$ wherein $R^{6q}$ represents: an alkyl group having from 1 to 4 carbon atoms; a cycloalkyl group having from 3 to 6 carbon atoms; a phenyl group; or a phenyl group substituted with an alkyl group having from 1 to 3 carbon atoms, an alkoxy group having from 1 to 3 carbon atoms, a halogen atom or a nitro group;

$R^{6p}$ represents: an alkyl group having from 1 to 4 carbon atoms; a cycloalkyl group having from 3 to 6 carbon atoms; a phenyl group; or a phenyl group substituted with an alkyl group having from 1 to 3 carbon atoms, an alkoxy group having from 1 to 3 carbon atoms, a halogen atom or a nitro group.

11. The compound of claim 1, wherein $R^1$ represents a group of formula —$NR^{9a}SO_mR^{6r}$
wherein:

$R^{9a}$ represents a hydrogen atom or a methyl group;

$R^{6r}$ represents: an alkyl group having from 1 to 4 carbon atoms; an alkyl group substituted with a cyano group; a phenyl group; or a phenyl group substituted with an alkyl group having from 1 to 3 carbon atoms, an alkoxy group having from 1 to 3 carbon atoms, a halogen atom or a nitro group; and m is 1 or 2.

12. The compound of claim 1, wherein A represents a group of formula:

—$CHR^2$—$CHR^3$—$CHR^4$— wherein $R^2$, $R^3$ and $R^4$ are independently selected from the group consisting of hydrogen atoms and methyl groups.

13. The compound of claim 1, wherein the substituent $R^1$ is at the meta or the ortho position.

14. The compound of claim 1, wherein A represents a group of formula:

—$CH^2$=$CR^3$—$CHR^4$— wherein $R^2$, $R^3$ and $R^4$ are independently selected from the group consisting of hydrogen atoms and methyl groups.

15. The compound of claim 1, wherein the substituent $R^1$ is at the meta or the ortho position.

16. The compound of claim 1, wherein A represents a group of formula:

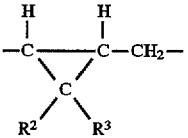

wherein $R^2$ and $R^3$ are independently selected from the group consisting of hydrogen atoms, chlorine atoms and methyl groups.

17. The compound of claim 1, wherein $R^5$ represents an ethyl group.

18. The compound of claim 1, which is a mixture of a compound wherein $R^5$ represents an ethyl group and the corresponding compound wherein $R^5$ represents a methyl group.

19. The compound of claim 1, wherein $R^3$ and $R^4$ each represent hydrogen atoms.

20. The compound of claim 1, wherein X represents a hydroxy group.

21. The compound of claim 1, selected from the group consisting of 13-(3-cyanoacetamidocinnamyloxy) milbemycin $A_4$ and pharmaceutically acceptable salts thereof.

22. The compound of claim 1, selected from the group consisting of 13-(3-methanesulfonylaminocinnamyloxy) milbemycin $A_4$ and pharmaceutically acceptable salts thereof.

23. The compound of claim 1, selected from the group consisting of 13-(3-N-(methanesulfonyl) methylaminocinnamyloxy) milbemycin $A_4$ and pharmaceutically acceptable salts thereof.

24. An anthelmintic, acaricidal and insecticidal composition comprising an anthelmintic, acaricidal and insecticidal compound in admixture with a pharmaceutically, agriculturally, veterinarily or horticulturally acceptable carrier or diluent, wherein said compound is selected from the group consisting of compounds of formula (I) and salts and esters thereof, as defined in claim 1.

25. The composition of claim 24, wherein said compound is selected from the group consisting of:

13-(3-aminocinnamyloxy)milbemycin $A_4$ 13-(2-aminocinnamyloxy)milbemycin $A_4$ 13-(3-acetamidocinnamyloxy)milbemycin $A_4$ 13-(3-(3-methylthioureido)cinnamyloxy)milbemycin $A_4$ 13-(3-cyanoacetamidocinnamyloxy)milbemycin $A_4$ 13-(3-methanesulfonylaminocinnamyloxy)milbemycin $A_4$ 13-(3-N-(methanesulfonyl)methylaminocinnamyloxy) milbemycin $A_4$ 13-(3-methylaminocinnamyloxy)milbemycin $A_4$ and 13-(3-(3,3-dimethylcarbazoylamino)cinnamyloxy) milbemycin $A_4$, and pharmaceutically acceptable salts thereof.

26. A method of treating an animal parasitized by a parasite selected from the group consisting of helminths, acarids and insects by administering thereto an effective parasiticidal amount of at least one compound selected from the group consisting of compounds of formula (I) as defined in claim 1 and salts and esters thereof.

27. The method of claim 26, wherein said compound is selected from the group consisting of:

13-(3-aminocinnamyloxy)milbemycin $A_4$ 13-(2-aminocinnamyloxy)milbemycin $A_4$ 13-(3-acetamidocinnamyloxy)milbemycin $A_4$ 13-(3-(3-methylthioureido)cinnamyloxy)milbemycin $A_4$ 13-(3-cyanoacetamidocinnamyloxy)milbemycin $A_4$ 13-(3-methanesulfonylaminocinnamyloxy)milbemycin $A_4$ 13-(3-$\underline{N}$-(methanesulfonyl)methylaminocinnamyloxy) milbemycin $A_4$ 13-(3-methylaminocinnamyloxy)milbemycin $A_4$ and 13-(3-(3,3-dimethylcarbazoylamino)cinnamyloxy) milbemycin $A_4$, and pharmaceutically acceptable salts thereof.

28. A method of protecting animal or plants from damage by parasites selected from the group consisting of acarids, helminths and insects, which comprises applying an effective parasiticidal amount of active compound to said animals, to said plants or to seeds of said plants or to a locus including said animals, plants or seeds, wherein the active compound is selected from the group consisting of at least one compound of formula (I) as defined in claim 1 and salts and esters thereof.

29. The method of claim 28, wherein said compound is selected from the group consisting of:

13-(3-aminocinnamyloxy)milbemycin $A_4$ 13-(2-aminocinnamyloxy)milbemycin $A_4$ 13-(3-acetamidocinnamyloxy)milbemycin $A_4$ 13-(3-(3-methylthioureido)cinnamyloxy)milbemycin $A_4$ 13-(3-cyanoacetamidocinnamyloxy)milbemycin $A_4$ 13-(3-methanesulfonylaminocinnamyloxy)milbemycin $A_4$ 13-(3-N-(methanesulfonyl)methylaminocinnamyloxy) milbemycin $A_4$ 13-(3-methylaminocinnamyloxy)milbemycin $A_4$ and 13-(3-(3,3-dimethylcarbazoylamino)cinnamyloxy) milbemycin $A_4$, and pharmaceutically acceptable salts thereof.

30. A method of protecting animals or plants from damage by parasites selected from the group consisting of acarids, helminths and insects, which comprises applying an effective parasiticidal amount of an active compound to said animals, to said plants or to seeds of said plants or to a locus including said animals, plants or seeds, wherein the active compound is selected from the group consisting of at least one compound of formula $(I)_w$ or a salt thereof

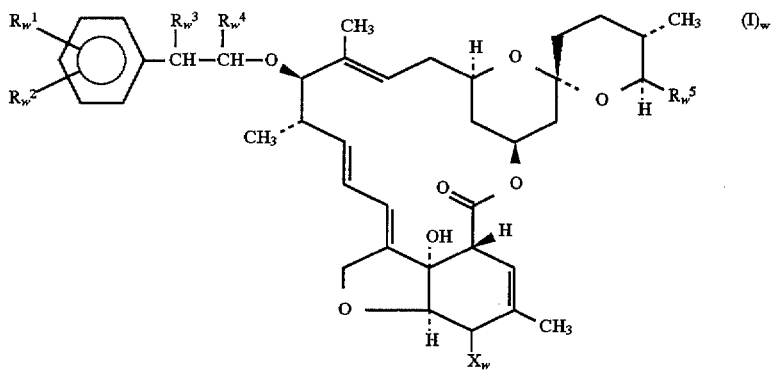

in which:

$R_w^1$ and $R_w^2$ are independently selected from the group consisting of: hydrogen atoms; halogen atoms; cyano groups; nitro groups; $C_1$–$C_4$ alkyl groups; substituted $C_1$–$C_4$ alkyl groups having at least one substituent selected from the group consisting of substituents (a), defined below; $C_1$–$C_4$ alkoxy groups; $C_2$–$C_6$ alkoxyalkoxy groups; groups of formula —$(CH_2)_{n_w}NHR_w^9$, in which:

$n_w$ represents 0 or the integer 1 or 2, and $R_w^9$ represents a hydrogen atom or a $C_1$–$C_4$ alkyl group;

groups of formula —$(CH_2)_{n_w}NR_w^9C(=O)R_w^6$, in which:

$n_w$ and $R_w^9$ are as defined above, and $R_w^6$ represents: a hydrogen atom: a $C_1$–$C_4$ alkyl group; a substituted $C_1$–$C_4$ alkyl group having at least one substituent selected from the group consisting of substituents (b), defined below; a $C_2$–$C_8$ aliphatic hydrocarbon group having one or two ethylenically unsaturated carbon-carbon double bonds, said group being unsubstituted or having at least one substituent selected from the group consisting of substituents (b)$_w$, defined below; a $C_2$–$C_8$ alkynyl group; a substituted $C_2$–$C_8$ alkynyl group having at least one substituent selected from the group consisting of substituents (b)$_w$, defined below; a $C_3$–$C_8$ cycloalkyl group; a substituted $C_3$–$C_8$ cycloalkyl group having at least one substituent selected from the group consisting of substituents (c)$_w$, defined below; a carbocyclic aryl group having from 6 to 14 ring carbon atoms and being unsubstituted or having at least one substituent selected from the group consisting of substituents (c)$_w$, defined below; or a heterocyclic group selected from the group consisting of oxiranyl, oxetanyl, aziridinyl, azetidinyl, thiranyl, thietanyl, furyl, thienyl, pyrrolyl, pyridyl, thiazolyl, isothiazolyl, oxazolyl, isoxazolyl, imidazolyl, pyrazolyl, pyranyl, pyrazinyl, piperidinyl, pyridazinyl, pyrimidinyl, benzofuranyl, isobenzofuranyl, benzothienyl, isobenzothienyl, indolyl, quinolyl, isoquinolyl, quinazolinyl, quinoxalinyl, naphthyridynyl, xanthenyl, tetrahydrofuranyl, tetrahydrothienyl, pyrrolidinyl, thiazolidinyl, imidazolidinyl, imidazolinyl, oxazolinyl, oxazolidinyl, pyrazolidinyl, piperazyl, tetrahydropyrimidinyl, dihydropyridazinyl, morpholinyl, thiomorpholinyl, indolinyl, tetrahydroquinolyl, pyrrolidonyl, piperidonyl, pyridonyl, thianthrenyl, chromenyl, phenoxathiinyl, 2H-pyrrolyl, isoindolyl, 3H-indolyl, indazolyl, phthalazinyl, quinoxalinyl, quinazolinyl, cinnolinyl, carbazolyl, phenanthridinyl, acridinyl, perimidinyl, phenazinylphenothiazinyl, furazanyl, phenoxazinyl, isochromanyl, chromanyl, pyrazolinyl, indolinyl and isoindolinyl said heterocyclic group being unsubstituted or having at least one substituent selected from the group consisting of substituents (c)$_w$, defined below;

groups of formula —$(CH_2)_{n_w}NR_w^9COCOR_w^6$ in which $n_w$, $R_w^6$ and $R_w^9$ are as defined above;

groups of formula —$(CH_2)_{n_w}R_w^9COCOOR_w^7$ in which $n_w$ and $R_w^9$ are as defined above and $R_w^7$ represents a $C_1$–$C_4$ alkyl group, a $C_3$–$C_8$ cycloalkyl group or an aralkyl group as defined below;

groups of formula —$(CH_2)_{n_w}NR_w^9CHR_w^6NHCOR_w^6$ in which $n_w$, $R_w^6$ and $R_w^9$ are as defined above;

groups of formula —$(CH_2)_{n_w}NR_w^9CHR_w^6NHCONHR_w^6$ in which $n_w$, $R_w^6$ and $R_w^9$ are as defined above;

groups of formula —$(CH_2)_{n_w}NR_w^9CHR_w^6NHCOOR_w^7$ in which $n_w$, $R^6$, $R_w^7$ and $R_w^9$ are as defined above;

groups of formula —$(CH_2)_{n_w}NR_w^9C(=Y_w)Y_wR_w^6$ in which $n_w$, $R_w^6$ and $R_w^9$ are as defined above and the two symbols Y are independently selected from the group consisting of oxygen and sulfur atoms;

groups of formula —$(CH_2)_{n_w}NR_w^9C(=Y)NR_w^{6'}R_w^{6'}$ in which $n_w$, $Y_w$ and $R_w^9$ are as defined above, and the two symbols $R_w^{6'}$ are independently selected from the group consisting of $R_w^6$, or the two, together with the nitrogen atom to which they are attached, form a heterocyclic group selected from the group consisting of aziridinyl, azetidinyl, pyrrolyl, imidazolyl, pyrazolyl, pyrrolidinyl, thiazolidinyl, imidazolidinyl, imidazolonyl, oxazolinyl, oxazolidinyl, pyrazolidinyl, piperazyl, tetrahydropyrimidinyl, dihydropyridazinyl, pyrrolidonyl, piperidonyl, pyridonyl, pyrazolinyl, azepinyl, perhydroazepinyl, oxazepinyl and thiazepinyl;

groups of formula —$(CH_2)_{n_w}NR_w^9C(=Y_w)NR_w^{6''}NR_w^{6''}R_w^{6''}$ in which $n_w$, $Y_w$ and $R_w^9$ are as defined above, and each of the symbols $R_w^{6''}$ is independently selected from the group consisting of $R_w^6$, or any two of the symbols $R_w^{6''}$, together with the nitrogen atom to which each is attached, forms a heterocyclic group selected from the group consisting of diaziridine, diazete, diazetidine, pyrazolidine, pyrazoline, 1,2-dihydropyridazine, 1,2,3,4-tetrahydropyridazine, 1,2,5,6-tetrahydropyridazine, perhydropyridazine, 1,2-dihydro-1,2-diazepine and perhydro-1,2-diazepine;

groups of formula —$(CH_2)_{n_w}NR_w^9C(=Y_w)NR_w^6NHZ_w$
in which
$n_w$, $Y_w$, $R_w^6$ and $R_w^9$ are as defined above and Z represents
a group of formula —$COOR_w^7$, in which $R_w^7$ is as defined above,
a group of formula —$COR_w^6$, in which $R_w^6$ is as defined above, or
a group of formula —$SO_2R_w^6$, in which $R_w^6$ is as defined above;

groups of formula —$(CH_2)_{n_w}NR_w^9C(=NR_w^{10})NHR_w^{10}$
in which
n and $R_w^9$ are as defined above and the two symbols $R_w^{10}$ are independently selected from the group consisting of $R_w^6$, cyano groups, nitro groups, groups of formula —$COOR_w^7$, in which $R_w^7$ is as defined above, and groups of formula —$COR_w^6$, in which $R_w^6$ is as defined above;

groups of formula —$(CH_2)_{n_w}NR_w^9C(=NR_w^{10})R_w^6$
in which
$n_w$, $R_w^6$, $R_w^9$ and $R_w^{10}$ are as defined above;

groups of formula —$(CH_2)_{n_w}NR_w^9SO_mR_w^6$
in which
$n_w$, $R_w^6$ and $R_w^9$ are as defined above and m is 1 or 2;

groups of formula —$CONHR_w^6$
in which
$R_w^6$ is as defined above; and groups of formula —$COOR_w^7$
in which
$R_w^7$ is as defined above;

$R_w^3$ and $R_w^4$ are independently selected from the group consisting of hydrogen atoms, $C_1$–$C_4$ alkyl groups and $C_1$–$C_4$ alkoxy groups;

$R_w^5$ represents a methyl group, an ethyl group, an isopropyl group or a sec-butyl group; and $X_w$ represents a hydroxy group, a $C_1$–$C_5$ alkanoyloxy group, a substituted $C_1$–$C_5$ alkanoyloxy group having at least one substituent selected from the group consisting of substituents (d), defined below, or a hydroxyimino group;

said aralkyl groups have from 1 to 4 carbon atoms in the alkyl part from 6 to 10 ring atoms in the aryl part, which is a carbocyclic aryl group which is unsubstituted or has at least one substituent selected from the group consisting of substituents (c), defined below;

substituents (a)w:
halogen atoms, $C_1$–$C_4$ alkoxy groups, $C_1$–$C_4$ alkylthio groups and $C_1$–$C_5$ alkanoyloxy groups;

substituents (b)w:
$C_3$–$C_8$ cycloalkyl groups; $C_1$–$C_4$ alkoxy groups; $C_1$–$C_4$ alkylthio groups: $C_2$–$C_5$ cyanoalkylthio groups: $C_2$–$C_5$ alkoxycarbonyl groups; halogen atoms; cyano groups; nitro groups; amino groups; carbocyclic aryl groups having from 6 to 10 carbon atoms and being unsubstituted or having at least one substituent selected from the group consisting of substituents (c)$_w$, defined below; aromatic heterocyclic groups having from 5 to 8 ring atoms of which from 1 to 4 are hetero-atoms selected from the group consisting of nitrogen, oxygen and sulfur hetero-atoms, said heterocyclic group being monocyclic or fused either to a benzene ring or to a heterocyclic group which has 5 or 6 ring atoms of which from 1 to 3 are nitrogen hetero-atoms and being unsubstituted or having at least one substituent selected from the group consisting of substituents (c)$_w$, defined below; and aryloxy and arylthio groups in which the aryl part has from 6 to 10 carbon atoms and is unsubstituted or has at least one substituent selected from the group consisting of substituents (c)$_w$, defined below;

substituents (c)w:
$C_1$–$C_4$ alkyl groups, $C_1$–$C_4$ alkoxy groups, $C_1$–$C_4$ alkylthio groups, $C_1$–$C_5$ alkanoyloxy groups, $C_2$–$C_5$ alkoxycarbonyl groups, halogen atoms, cyano groups, nitro groups, amino groups, mono- and di- alkylamino groups in which the or each alkyl part is $C_1$–$C_4$, carbamoyl groups, mono- and di- alkylcarbamoyl groups in which the or each alkyl part is $C_1$–$C_4$, and $C_1$–$C_5$ alkanoylamino groups;

substituents (d)w:
halogen atoms, $C_1$–$C_4$ alkoxy groups, $C_2$–$C_5$ alkoxycarbonyl groups and carboxy groups.

31. The method of claim 30, wherein:
$R_w^1$ represents a hydrogen atom; and
$R_w^2$ represents, at the p-position of the benzene ring:
a hydrogen atom; a $C_1$–$C_3$ alkyl group; a $C_1$–$C_3$ alkoxy group; a fluorine or chlorine atom; a nitro group: an amino group; a group of formula —$(CH_2)_{n_w}NR_w^{9a}COR_w^{6a}$
in which $n_w$ is 0, $R_w^{9a}$ represents a hydrogen atom or a methyl group, and $R_w^{6a}$ represents a $C_1$–$C_4$ alkyl group, a $C_3$–$C_5$ cycloalkyl group, a $C_1$–$C_3$ alkyl group substituted with a halogen, cyano, $C_1$–$C_3$ alkoxy, $C_1$–$C_3$ alkylthio, cyanomethylthio or phenoxy substituent; an alkenyl group, an unsubstituted phenyl group, a phenyl group substituted with a $C_1$–$C_3$ alkyl, $C_1$–$C_3$ alkoxy, halogen or nitro substituent, a pyridyl group, a pyrimidyl group, a pyrazyl group, a furyl group or a thienyl group;

a group of formula —$(CH_2)_{n_w}NR_w^{9a}COCOR_w^{6b}$
in which $n_w$ and $R_w^{9a}$ are as defined above, and $R_w^{6b}$ represents a hydrogen atom, a $C_1$–$C_4$ alkyl group, a $C_3$–$C_5$ cycloalkyl group, an alkenyl group, an unsubstituted phenyl group, a phenyl group substituted with a $C_1$–$C_3$ alkyl, $C_1$–$C_3$ alkoxy, halogen or nitro substituent;

a group of formula —$(CH_2)_{n_w}NR_w^{9a}C(=Y_w)Y_wR_w^{6c}$
in which $n_w$ and $R_w^{9a}$ are as defined above, both Y are oxygen atoms and $R_w^{6c}$ represents a $C_1$–$C_4$ alkyl group, a $C_1$–$C_4$ alkyl group substituted with a halogen or $C_1$–$C_3$ alkoxy substituent, an alkenyl group, a benzyl group, a methoxybenzyl group, a nitrobenzyl group, a furfuryl group, a thienye group or a phenyl group;

a group of formula —$(CH_2)_{n_w}NR_w^{9a}C(=Y_w)NR_w^{6d}R_w^{6e}$
in which $n_w$, $R_w^{9a}$ and $Y_w$ are as defined above, and $R_w^{6d}$ and $R_w^{6e}$ are the same or different and each represents a $C_1$–$C_4$ alkyl group, a $C_3$–$C_6$ cycloalkyl group, an unsubstituted phenyl group, a phenyl group substituted with a $C_1$–$C_3$ alkyl, $C_1$–$C_3$ alkoxy, halogen or nitro substituent, or $R_w^{6d}$ and $R_w^{6e}$, together with the nitrogen atom to which they are attached, represent a piperidino, piperazino, morpholino, pyrrolidino or aziridino group;

a group of formula $-(CH_2)_{n_w}NR_w^{9a}C(=Y_w)NR_w^{6f}NR_w^{6g}R_w^{6h}$ in which $n_w$, $R_w^{9a}$ and Y are as defined above, and $R_w^{6f}$, $R_w^{6g}$ and $R_w^{6h}$ are the same or different and each represents a hydrogen atom, a $C_1-C_4$ alkyl group, a $C_3-C_6$ cycloalkyl group, an unsubstituted phenyl group; a phenyl group substituted with a $C_1-C_3$ alkyl, $C_1-C_3$ alkoxy, halogen or nitro substituent, or $R_w^{6g}$ and $R_w^{6h}$, together with the nitrogen atom to which they are attached, represent a piperidino, piperazino, morpholino, pyrrolidino or aziridino group, or $R_w^{6f}$ and $R_w^{6g}$, together with the nitrogen atoms to which they are attached, represent a pyrazolidinyl or tetrahydropyridazinyl group;

a group of formula $-(CH_2)_{n_w}NR_w^{9a}C(=Y_w)NR_w^{6f}NHZ_w$ in which $n_w$, $R_w^{9a}$ and $Y_w$ are as defined above, $R_w^{6f}$ represents a hydrogen atom, a $C_1-C_4$ alkyl group or a $C_3-C_6$ cycloalkyl group; and Z represents a group of formula $-COOR_w^{7a}$ wherein $R_w^{7a}$ represents a $C_1-C_4$ alkyl group, a $C_3-C_6$ cycloalkyl group or a benzyl group, a group of formula $-COR_w^{6k}$ wherein $R_w^{6k}$ represents a $C_1-C_4$ alkyl group, a $C_3-C_6$ cycloalkyl group, an unsubstituted phenyl group or a phenyl group substituted with a $C_1-C_3$ alkyl, $C_1-C_3$ alkoxy, halogen or nitro substituent or a group of formula $-SO_2R_w^{6m}$ wherein $R_w^{6m}$ represents a $C_1-C_4$ alkyl group, an unsubstituted phenyl group or a phenyl group substituted with a $C_1-C_3$ alkyl, $C_1-C_3$ alkoxy, halogen or nitro substituent;

a group of formula $-(CH_2)_{n_w}NR_w^{9a}C(=NR_w^{10a})NHR_w^{10b}$ in which $n_w$ and $R^{9a}$ are as defined above, and $R_w^{10a}$ and $R_w^{10b}$ are the same or different and each represents a hydrogen atom, a $C_1-C_4$ alkyl group, an unsubstituted phenyl group, a phenyl group substituted with a $C_1-C_3$ alkyl, $C_1-C_3$ alkoxy, halogen or nitro substituent, a group of formula $-COOR_w^{7b}$ wherein $R_w^{7b}$ represents a $C_1-C_4$ alkyl group, a $C_3-C_6$ cycloalkyl group or a benzyl group or a group of formula $-COR_w^{6n}$ wherein $R_w^{6n}$ represents a $C_1-C_4$ alkyl group, a $C_3-C_6$ cycloalkyl group, an unsubstituted phenyl group or a phenyl group substituted with a $C_1-C_3$ alkyl, $C_1-C_3$ alkoxy, halogen or nitro substituent;

a group of formula $-(CH_2)_{n_w}NR_w^{9a}C(=NR_w^{10c})R_w^{6p}$ in which $n_w$ and $R_w^{9a}$ are as defined above; $R_w^{10c}$ represents a hydrogen atom, a $C_1-C_4$ alkyl group, an unsubstituted phenyl group, a phenyl group substituted with a $C_1-C_3$ alkyl, $C_1-C_3$ alkoxy, halogen or nitro substituent, a group of formula $-COOR_w^{7c}$ wherein $R_w^{7c}$ represents a $C_1-C_4$ alkyl group, a $C_3-C_6$ cycloalkyl group or a benzyl group;

or a group of formula $-COR_w^{6q}$ wherein $R_w^{6q}$ represents a $C_1-C_4$ alkyl group, a $C_3-C_6$ cycloalkyl group, an unsubstituted phenyl group; or a phenyl group substituted with a $C_1-C_3$ alkyl, $C_1-C_3$ alkoxy, halogen or nitro substituent and $R_w^{6p}$ represents a $C_1-C_4$ alkyl group, a $C_3-C_6$ cycloalkyl group, an unsubstituted phenyl group or a phenyl group substituted with a $C_1-C_3$ alkyl, $C_1-C_3$ alkoxy, halogen or nitro substituent;

a group of formula $-(CH_2)_{n_w}NR_w^{9a}SO_{m_w}R_w^{6r}$ in which $n_w$ and $R_w^{9a}$ are as defined above, $m_w$ is 1 or 2, and $R_w^{6r}$ represents a $C_1-C_4$ alkyl group, a $C_2-C_4$ cyanoalkyl group, an unsubstituted phenyl group, a phenyl group substituted with a $C_1-C_3$ alkyl, $C_1-C_3$ alkoxy, halogen or nitro substituent;

or a group of formula $-CONHR_w^{6s}$ in which $R_w^{6s}$ represents a $C_1-C_4$ alkyl group, a $C_3-C_6$ cycloalkyl group, an unsubstituted phenyl group or a phenyl group substituted with a $C_1-C_3$ alkyl;

$C_1-C_3$ alkoxy, halogen or nitro substituent;

$R_w^5$ represents an ethyl group or said compound of formula $(I)_w$ is a mixture of compounds wherein in one of said compounds $R_w^5$ represents an ethyl group and in the other of said compounds $R_w^5$ represents a methyl group;

$R_w^3$ and $R_w^4$ are hydrogen atoms; and $x_w$ represents a hydroxy group.

32. The method of claim 30, wherein said compound is selected from the group consisting of:

13-(2-(4-acetamidophenyl)ethoxy)milbemycin $A_4$;

13-(2-(4-cyanoacetamidophenyl)ethoxy)milbemycin $A_4$;

13-{2-(4-(2-cyanopropionamido)phenyl)ethoxy}milbemycin $A_4$;

13-(2-(4-methoxyacetamidophenyl)ethoxy)milbemycin $A_4$;

13-{2-[4-(cyclopropylcarbonylamino)phenyl)ethoxy}milbemycin $A_4$;

13-{2-(4-(cyclobutylcarbonylamino)phenyl)ethoxy}milbemycin $A_4$;

13-{2-(4-(4-cyanobenzamido)phenyl)ethoxy}milbemycin $A_4$;

13-(2-(4-methoxycarbonylaminophenyl)ethoxy) milbemycin $A_4$;

13-(2-(4-vinyloxycarbonylaminophenyl)ethoxy milbemycin $A_4$;

13-{2-(4-(3-methylureido)phenyl)ethoxy}milbemycin $A_4$;

13-{2-(4-(3-phenylureido)phenyl)ethoxy}milbemycin $A_4$;

13-{2-(4-(3-cyclohexylureido)phenyl)ethoxy}milbemycin $A_4$;

13-(2-(4-methanesulfonylaminophenyl)ethoxy) milbemycin $A_4$;

13-(2-(4-ethanesulfonylaminophenyl)ethoxy)milbemycin $A_4$;

13-{2-(4-(3,3-dimethylcarbazoylamino)phenyl)ethoxy}milbemycin $A_4$;

13-{2-(4-(3-o-fluorophenylureido)phenyl)ethoxy}milbemycin $A_4$;

13-{2-(4-(3-p-fluorophenylureido)phenyl)ethoxy}milbemycin $A_4$;

13-{2-(4-(3-p-methoxyphenylureido)phenyl)ethoxy}milbemycin $A_4$ and salts thereof.

33. The method of claim 30, wherein said compound is selected from the group consisting of 13-(2-(4-methoxyphenyl)ethoxy)milbemycin $A_4$,
13-(2-(3,4-dimethoxyphenyl)ethoxy)milbemycin $A_4$,
13-(2-(4-aminophenyl)ethoxy)milbemycin $A_4$ and
13-(2-(4-ethoxycarbonylaminophenyl)ethoxy) milbemycin $A_4$.

34. The method of claim 31, wherein $R_w^6$, is an alkenyl group selected from the group consisting of a vinyl group and allyl group.

35. The method of claim 30, wherein:
$R_w^1$ represents a hydrogen atom; and
$R_w^2$ represents a hydrogen atom, a $C_1$–$C_3$ alkyl group, a $C_1$–$C_3$ alkoxy group, a fluorine or chlorine atom, a nitro group or an amino group.

36. The method of claim 30, wherein:
$R_w^1$ represents a hydrogen atom; and
$R_w^2$ represents a group of formula —$(CH_2)_{n_w}NR_w^9COR_w^6$
in which $n_w$ is 0, $R_w^9$ represents a hydrogen atom or a methyl group, and $R^6$ represents a $C_1$–$C_4$ alkyl group, a $C_3$–$C_5$ cycloalkyl group, a $C_1$–$C_3$ alkyl group substituted with a halogen, cyano, $C_1$–$C_3$ alkoxy, $C_1$–$C_3$ alkylthio, cyanomethylthio or phenoxy substituent; an alkenyl group, an unsubstituted phenyl group, a phenyl group substituted with a $C_1$–$C_3$ alkyl, $C_1$–$C_3$ alkoxy, halogen or nitro substituent, a pyridyl group, a pyrimidyl group, a pyrazyl group, a furyl group or a thienyl group.

37. The method of claim 30, wherein:
$R_w^1$ represents a hydrogen atom; and
$R_w^2$ represents a group of formula —$(CH_2)_{n_w}NR_w^9COCOR_w^6$
in which $n_w$ is 0, $R_w^9$ represents a hydrogen atom or a methyl group, and $R_w^6$ represents a hydrogen atom, a $C_1$–$C_4$ alkyl group, a $C_3$–$C_5$ cycloalkyl group, an alkenyl group, an unsubstituted phenyl group, a phenyl group, substituted with a $C_1$–$C_3$ alkyl, $C_1$–$C_3$ alkoxy, halogen or nitro substituent.

38. The method of claim 30, wherein:
$R_w^1$ represents a hydrogen atom; and
$R_w^2$ represents a group of formula —$(CH_2)_{n_w}NR_w^9C(=Y_w)YR_w^6$
in which $n_w$ is 0, $R_w^9$ represents a hydrogen atom or a methyl group, both $Y_w$ are oxygen atoms and $R_w^6$ represents a $C_1$–$C_4$ alkyl group, a $C_1$–$C_4$ alkyl group substituted with a halogen or $C_1$–$C_3$ alkoxy substituent, an alkenyl group, a benzyl group, a methoxybenzyl group, a nitrobenzyl group, a furfuryl group, a thenyl group or a phenyl group.

39. The method of claim 30, wherein:
$R_w^1$ represents a hydrogen atom; and
$R_w^2$ represents a group of formula —$(CH_2)_{n_w}NR_w^9C(=Y_w)NR_w^{6'}R_w^{6'}$ in which $n_w$ is 0, $R_w^9$ represents a hydrogen atom or a methyl group, $y_w$ represents an oxygen atom or a sulfur atom, and each $R_w^{6'}$ is the same or different and each represents a
$C_1$–$C_4$ alkyl group, a $C_3$–$C_6$ cycloalkyl group, an unsubstituted phenyl group, a phenyl group substituted with a $C_1$–$C_3$ alkyl, $C_1$–$C_3$ alkoxy, halogen or nitro substituent, or $R_w^{6'}R_w^{6'}$, together with the nitrogen atom to which they are attached, represent a piperidino, piperazino, morpholino, pyrrolidino or aziridino group.

40. The method of claim 20, wherein:
$R_w^1$ represents a hydrogen atom; and
$R_w^2$ represents a group of formula —$(CH_2)_{n_w}NR_w^9C(=Y_w)NR_w^{6''}NR_w^{6''}R_w^{6''}$ in which $n_w$ is 0, $R_w^9$ represents a hydrogen atom or a methyl group, $Y_w$ represents an oxygen atom or a sulfur atom, and each $R_w^{6''}$ is the same or different and each represents a hydrogen atom, a $C_1$–$C_4$ alkyl group, a $C_3$–$C_6$ cycloalkyl group, an unsubstituted phenyl group; a phenyl group substituted with a $C_1$–$C_3$ alkyl, $C_1$–$C_3$ alkoxy, halogen or nitro substituent, or $NR_w^{6''}R_w^{6''}$ represents a piperidino, piperazino, morpholino, pyrrolidino or aziridino group, or $NR_w^{6''}NR_w^{6''}$ represent a pyrazolidinyl or tetrahydropyridazinyl group.

41. The method of claim 30, wherein:
$R_w^1$ represents a hydrogen atom; and
$R_w^2$ represents a group of formula —$(CH_2)_{n_w}NR_w^9C(=Y_w)NR_w^6NHZ_w$ in which $n_w$ is 0, $R_w^9$ represents a hydrogen atom or a methyl group, $y_w$ represent an oxygen atom or a sulfur atom, $R_w^6$ represents a hydrogen atom, a $C_1$–$C_4$ alkyl group or a $C_3$–$C_6$ cycloalkyl group; $z_w$ represents a group of formula —$COOR_w^7$
wherein $R_w^7$ represents a $C_1$–$C_4$ alkyl group, a $C_3$–$C_6$ cycloalkyl group or a benzyl group,
a group of formula —$COR_w^6$
wherein $R_w^6$ represents a $C_1$–$C_4$ alkyl group, a $C_3$–$C_6$ cycloalkyl group, an unsubstituted phenyl group or a phenyl group substituted with a $C_1$–$C_3$ alkyl, $C_1$–$C_3$ alkoxy, halogen or nitro substituent or
a group of formula —$SO_2R_w^6$
wherein $R_w^6$ represents a $C_1$–$C_4$ alkyl group, an unsubstituted phenyl group or a phenyl group substituted with a $C_1$–$C_3$ alkyl, $C_1$–$C_3$ alkoxy, halogen or nitro substituent.

42. The method of claim 30, wherein:
$R_w^1$ represents a hydrogen atom; and
$R_w^2$ represents a group of formula —$(CH_2)_{n_w}NR_w^9C(=NR_w^{10})NHR_w^{10}$ in which $n_w$ is 0, $R_w^9$ represents a hydrogen atom or a methyl group, and each $R_w^{10}$ is the same or different and each represents a hydrogen atom, a $C_1$–$C_4$ alkyl group, an unsubstituted phenyl group, a phenyl group substituted with a $C_1$–$C_3$ alkyl, $C_1$–$C_3$ alkoxy, halogen or nitro substituent, a group of formula —$COOR_w^7$
wherein $R_w^7$ represents a $C_1$–$C_4$ alkyl group, a $C_3$–$C_6$ cycloalkyl group or a benzyl group or
a group of formula —$COR_w^6$
wherein $R_w^6$ represents a $C_1$–$C_4$ alkyl group, a $C_3$–$C_6$ cycloalkyl group, an unsubstituted phenyl group or a phenyl group substituted with a $C_1$–$C_3$ alkyl, $C_1$–$C_3$ alkoxy, halogen or nitro substituent.

43. The method of claim 30, wherein:
$R_w^1$ represents a hydrogen atom; and
$R_w^2$ represents a group of formula —$(CH_2)_{n_w}NR_w^9C(=NR_w^{10})R_w^6$ in which $n_w$ is 0; $R_w^9$ represents a hydrogen atom or a methyl group; $R_w^{10}$ represents a hydrogen atom, a $C_1$–$C_4$ alkyl group, an unsubstituted phenyl group, a phenyl group substituted with a $C_1$–$C_3$ alkyl, $C_1$–$C_3$ alkoxy, halogen or nitro substituent, a group of formula —$COOR_w^7$ wherein $R_w^7$ represents a $C_1$–$C_4$ alkyl group, a $C_3$–$C_6$ cycloalkyl group or a benzyl group;

or a group of formula —$COR_w^6$ wherein $R_w^6$ represents a $C_1$–$C_4$ alkyl group, a $C_3$–$C_6$ cycloalkyl group, an unsubstituted phenyl group; or a phenyl group substituted with a $C_1$–$C_3$ alkyl, $C_1$–$C_3$ alkoxy, halogen or nitro substituent and $R_w^6$ represents a $C_1$–$C_4$ alkyl group, a $C_3$–$C_6$ cycloalkyl group, an unsubstituted phenyl group or a phenyl group substituted with a $C_1$–$C_3$ alkyl, $C_1$–$C_3$ alkoxy, halogen or nitro substituent.

44. The method of claim 30, wherein:

$R_w^1$ represents a hydrogen atom; and $R_w^2$ represents a group of formula —$(CH_2)_{n_w}NR_w^9SO_{m_w}R_w^6$ in which n is 0, $R_w^9$ represents a hydrogen atom or a methyl group, m is 1 or 2, and $R^6$ represents a $C_1$–$C_4$ alkyl group, a $C_2$–$C_4$ cyanoalkyl group, an unsubstituted phenyl group, a phenyl group, an unsubstituted phenyl group, a phenyl group substituted with a $C_1$–$C_3$ alkyl, $C_1$–$C_3$ alkoxy, halogen or nitro substituent.

45. The method of claim 30, wherein:

$R_w^1$ represents a hydrogen atom, and $R_w^2$ represents a group of formula —$CONHR_w^6$ in which $R_w^6$ represents a $C_1$–$C_4$ alkyl group, a $C_3$–$C_6$ cycloalkyl group, an unsubstituted phenyl group or a phenyl group substituted with a $C_1$–$C_3$ alkyl, $C_1$–$C_3$ alkoxy, halogen or nitro substituent.

46. The method of claim 36, wherein $R^2$ is an alkenyl group selected from the group consisting of a vinyl group and an allyl group.

47. The method of claim 30, wherein the substituent $(b)_w$ is selected from the group consisting of pyridyl, thienyl, furyl, pyrrolyl, imidazolyl, triazolyl, tetrazolyl, thiazolyl, oxazolyl, indolyl, benzofuryl, isobenzofuryl, chromenyl, 2H-pyrrolyl, pyrazolyl, isothiazolyl, isoxazolyl, pyrazinyl, pyrimidinyl, pyridazinyl, isoindolyl, 3H-indolyl, 1H-indazolyl, isoquinolyl, quinolyl, phthalazinyl, quinoxalinyl, quinazolinyl and cinnolinyl.

\* \* \* \* \*

UNITED STATES PATENT AND TRADEMARK OFFICE
CERTIFICATE OF CORRECTION

PATENT NO.  : 5,686,484
DATED       : November 11, 1997
INVENTOR(S) : Morisawa et al It is certified that error appears in the above-identified patent and that said Letters Patent is hereby corrected as shown below:

Column 1, line 8: after "of" insert --both (i)--.

Column 1, lines 10 and 11: delete "said Ser. No. 08/071,765, filed Jun. 9, 1993 which is a CIP of".

Column 1, line 11: before "Ser." insert --(ii)--.

Column 40, line 35: delete "(I)" and insert --(I)$_w$--.

Column 41, line 48: delete "(5)" and insert --(6)--.

Column 82, line 51: delete "wish" and insert --with--.

Column 104, line 15 (Claim 1): delete "aa" and insert --a--.

Column 114, line 57 (Claim 31): delete "thienye" and insert --thienyl--.

Signed and Sealed this

Twenty-sixth Day of October, 1999

Attest:

Q. TODD DICKINSON

*Attesting Officer*          *Acting Commissioner of Patents and Trademarks*